United States Patent
Ahmed et al.

(10) Patent No.: US 9,802,995 B2
(45) Date of Patent: Oct. 31, 2017

(54) ANTIBODY MULTIMERIZATION TECHNOLOGIES

(71) Applicant: Memorial Sloan-Kettering Cancer Center, New York, NY (US)

(72) Inventors: Mahiuddin Ahmed, New York, NY (US); Nai-Kong V. Cheung, Purchase, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 11 days.

(21) Appl. No.: 14/776,267

(22) PCT Filed: Mar. 14, 2014

(86) PCT No.: PCT/US2014/029041
§ 371 (c)(1),
(2) Date: Sep. 14, 2015

(87) PCT Pub. No.: WO2014/144573
PCT Pub. Date: Sep. 18, 2014

(65) Prior Publication Data
US 2016/0168211 A1  Jun. 16, 2016

Related U.S. Application Data

(60) Provisional application No. 61/791,600, filed on Mar. 15, 2013.

(51) Int. Cl.
| | | |
|---|---|---|
| *A61K 39/00* | (2006.01) | |
| *A61K 39/395* | (2006.01) | |
| *A61K 38/17* | (2006.01) | |
| *C07K 16/18* | (2006.01) | |
| *C07K 16/28* | (2006.01) | |
| *C07K 16/30* | (2006.01) | |
| *C07K 16/46* | (2006.01) | |
| *C07K 14/47* | (2006.01) | |

(52) U.S. Cl.
CPC .......... *C07K 14/47* (2013.01); *A61K 38/1709* (2013.01); *A61K 39/3955* (2013.01); *C07K 16/18* (2013.01); *C07K 16/2809* (2013.01); *C07K 16/30* (2013.01); *C07K 16/3053* (2013.01); *C07K 16/3084* (2013.01); *C07K 16/468* (2013.01); *A61K 2039/505* (2013.01); *C07K 2317/14* (2013.01); *C07K 2317/24* (2013.01); *C07K 2317/31* (2013.01); *C07K 2317/622* (2013.01); *C07K 2317/73* (2013.01); *C07K 2317/92* (2013.01); *C07K 2319/74* (2013.01)

(58) Field of Classification Search
CPC ............... C07K 2319/00; C07K 16/18; C07K 2317/31; C07K 2317/622; C07K 2317/569; C07K 2317/92; C07K 16/468; C07K 16/30; C07K 14/47; C07K 2317/73; C07K 2317/24; C07K 2319/33; C07K 16/2809; A61K 2039/505; A61K 39/3955

See application file for complete search history.

(56) References Cited

U.S. PATENT DOCUMENTS

| | | | |
|---|---|---|---|
| 7,521,056 | B2 | 4/2009 | Chang et al. |
| 2003/0109678 | A1 | 6/2003 | Cortese et al. |
| 2005/0079170 | A1 | 4/2005 | Le Gall et al. |
| 2006/0228300 | A1* | 10/2006 | Chang .................. A61K 39/395 424/1.49 |
| 2007/0298041 | A1 | 12/2007 | Tomlinson |

FOREIGN PATENT DOCUMENTS

| | | |
|---|---|---|
| EP | 2050764 A1 | 4/2009 |
| WO | WO-2014/144573 A2 | 9/2014 |

OTHER PUBLICATIONS

Baeuerle, P.A. and Reinhardt, C., Bispecific T-cell engaging antibodies for cancer therapy, Cancer Res., 69(12):4941-4 (2009).
Bargou, R. et al., Tumor regression in cancer patients by very low doses of a T cell-engaging antibody, Science, 321(5891):974-7 (2008).
Borsi, L. et al., Selective targeted delivery of TNFalpha to tumor blood vessels, Blood, 102(13):4384-92 (2003).
Brischwein, K., et al. MT110: a novel bispecific single-chain antibody construct with high efficacy in eradicating established tumors, Mol. Immunol., 43(8):1129-43 (2006).
Cheng, M. et al., Structrual design of disialoganglioside GD2 and CD3-bispecific antibodies to redirect T cells for tumor therapy, International Journal of Cancer, 00:00-00, 11 pages (2014).
Cheung, N.K. et al., Single-chain Fv-streptavidin substantially improved therapeutic index in multistep targeting directed at disialoganglioside GD2, J. Nucl. Med., 45(5):867-77 (2004).
Cheung, N.V. et al., Humanizing murine IgG3 anti-GD2 antibody m3F8 substantially improves antibody-dependent cell-mediated cytotoxicity while retaining targeting in vivo, OncoImmunology, 1(4):477-489 (2012).
Choi, B.D. et al., Bispecific antibodies engage T cells for antitumor immunotherapy, Expert. Opin. Biol. Ther., 11(7):843-53 (2011).
Cuesta, A.M. et al., Multivalent antibodies: when design surpasses evolution, Trends Biotechnol., 28(7):355-62 (2010).
Dreier, T. et al., T cell costimulus-independent and very efficacious inhibition of tumor growth in mice bearing subcutaneous or leukemic human B cell lymphoma xenografts by a CD19–/CD3– bispecific single-chain antibody construct, J. Immunol., 170(8):4397-402 (2003).

(Continued)

Primary Examiner — Robert Landsman
Assistant Examiner — Bruce D Hissong
(74) *Attorney, Agent, or Firm* — Choate, Hall & Stewart LLP; Brenda Herschbach Jarrell; Tracy L. Vrablik

(57) ABSTRACT

The present invention provides, among other things, dimeric multispecific binding agents (e.g., fusion proteins comprising antibody components) that have improved properties over multispecific binding agents without the capability of dimerization.

40 Claims, 11 Drawing Sheets

(56) References Cited

OTHER PUBLICATIONS

Goldenberg, D.M. et al., Multifunctional antibodies by the Dock-and-Lock method for improved cancer imaging and therapy by pretargeting, J. Nucl. Med., 49(1):158-63 (2008).

Halin, C. et al., Synergistic therapeutic effects of a tumor targeting antibody fragment, fused to interleukin 12 and to tumor necrosis factor alpha, Cancer Res., 63(12):3202-10 (2003).

Hu, J. et al., Reducing epitope spread during affinity maturation of an anti-ganglioside GD2 antibody, J. Immunol., 183(9):5748-55 (2009).

International Search Report for PCT/US2014/029041, 6 pages (Jul. 24, 2014).

Manzke et al., Immunotherapeutic Strategies in Neuroblastoma; Antitumoral activity of deglycosylated ricin a conjugated anti-GD2 antibodies and anti-CD3xanti-GD2 bispecific antibodies, Medical and Pediatric Oncology 36:185-189 (2001).

Modak, S. and Cheung, N.K., Disialoganglioside directed immunotherapy of neuroblastoma, Cancer Invest., 25(1):67-77 (2007).

Narayana, N. et al., The dimerization domain of HNF-1alpha: structure and plasticity of an intertwined four-helix bundle with application to diabetes mellitus, J. Mol. Biol., 310(3):635-58 (2001).

Ohta, S. et al., Antitumor effects of a novel monoclonal antibody with high binding affinity to ganglioside GD3, Cancer Immunol. Immunother., 36(4):260-6 (1993).

Plückthun, A. and Pack, P., New protein engineering approaches to multivalent and bispecific antibody fragments, Immunotechnology, 3(2):83-105 (1997).

Rossi, D.L. et al., A new class of bispecific antibodies to redirect T cells for cancer immunotherapy, MAbs., 6(2):381-91 (2014).

Ruf, P. et al., Ganglioside GD2-specific trifunctional surrogate antibody Surek demonstrates therapeutic activity in a mouse melanoma model, Journal of Translational Medicine, 10:219, 10 pages (2012).

Schwarzkopf, M., Sutro biopharma to collaborate with Memorial Sloan-Kettering Cancer Center to produce bispecific antibodies for the treatment of neuroblastoma, Press Release 1-3 (2014) retrieved from the internet on Jun. 30, 2014 <http://www.sutrobio.com/news/Sutro_News-Release_MSKCC-Final%20Clean_2_1.pdf>.

Wolf, E. et al., BiTEs: bispecific antibody constructs with unique anti-tumor activity, Drug Discov. Today, 10(18):1237-44 (2005).

Woodle, E.S. et al., Humanized OKT3 antibodies: successful transfer of immune modulating properties and idiotype expression, J. Immunol., 148(9):2756-63 (1992).

Written Opinion for PCT/US2014/029041, 8 pages (Jul. 24, 2014).

Yang, R.K. and Sondel, P.M., Anti-GD2 Strategy in the Treatment of Neuroblastoma, Drugs Future, 35(8):665 (2010).

Yankelevich, M. et al., Anti-CD3 T anti-GD2 bispecific antibody redirects T-cell cytolytic activity to neuroblastoma targets, Pediatric Blood Cancer 59: 1198-1205 (2012).

Extended European Search Report for EP 14765530.2, 9 pages, dated Oct. 7, 2016.

* cited by examiner

ANTIBODY MULTIMERIZATION TECHNOLOGIES

CROSS REFERENCE TO RELATED APPLICATIONS

This application is a national stage entry under 35 USC §371 of International Patent Application No. PCT/US2014/029041, filed Mar. 14, 2014 (the '041 application). The present application claims the benefit of priority thereto. The present application and the '041 application each claim the benefit of the filing date under 35 USC §119(e) of U.S. Provisional Patent Application Ser. No. 61/791,600, filed Mar. 15, 2013 (the '600 application). The entire contents of each of the '041 and '600 applications are incorporated herein by reference.

SEQUENCE LISTING

The present specification makes reference to a sequence listing submitted in electronic Form as an ASCII text file named "2003080-0636_ST25" on Jan. 28, 2016. The .txt file was generated on Mar. 7, 2014 and updated on Jan. 28, 2016 and is 102 kb in size. This sequence listing is herein incorporated by reference in its entirety.

BACKGROUND

Bi- and multi-specific binding agents are currently being developed for a variety of therapeutic, diagnostic, and research applications. Many such agents are generated by associating antibody components that target different antigens to one another, for example as fusion proteins or by cross-linking of antibody components. Such approaches, among others, have included generating multispecific antibodies by fusion of cells (e.g., hybridomas) that each express a monospecific antibody, chemical conjugation of two or more monospecific antibodies, and/or recombinant DNA technology. However, such methods have not been without limitation.

In particular, recombinant DNA technology has yielded several engineered antibodies that are multispecific and multifunctional. With the advent of single chain Fv molecules, many advances in engineered antibodies have been made. Such engineered antibodies have exhibited improved properties over traditional antibodies due, at least in part, to unique formats that have resulted. Although several strategies exist for engineering multispecific antibody agents, most efforts have focused on improving only certain functional aspects. As a result, most engineered proteins made from antibody components do not possess all the desired functional properties that would confer the most pharmacological significance.

SUMMARY

The present invention provides, among other things, improved multi-specific binding agents that include a multimerization component. Such provided agents have improved functional characteristics as compared to parental binding agents that lack such multimerization components.

In certain embodiments, provided agents are comprised of individual polypeptides, each of which includes at least one, and more commonly at least two or more binding moieties that specifically interact with a particular target. In many embodiments, such binding moieties are or comprise antibody components. Among other things, in some embodiments, the present invention provides polypeptides comprising an antibody component having an amino acid sequence comprising at least binding elements of antibody 5F11. In accordance with the present invention, such individual polypeptides within provided agents are engineered to include a multimerization component. In many embodiments, such polypeptides include a dimerization component. In many embodiments, the dimerization component is an element of human hepatocyte nuclear factor-1 alpha.

In certain particular embodiments described herein, provided agents are comprised of bispecific antibody polypeptides engineered to contain a multimerization component.

In some embodiments, the present invention provides bispecific binding agents comprised of two fusion proteins, each of which comprises a first antibody component that binds a first antigen; a second antibody component that binds a second antigen, and a dimerization component comprising a human hepatocyte nuclear factor-1 alpha (HNF-1α) element.

In some embodiments, first and second antigens of the present invention are not the same. In some embodiments, a first antigen of the present invention is a tumor antigen. In some embodiments, a tumor antigen is associated with a B cell or a T cell. In some embodiments, a tumor antigen of the present invention is GD2. In some embodiments, a tumor antigen of the present invention is GD3.

In some embodiments, a second antigen of the present invention is present on T cells. In some embodiments, a second antigen of the present invention is CD3.

In some embodiments, a dimerization component of the present invention has a sequence at least about 50% (e.g., at least about 55%, 60%, 65%, 70%, 75%, 80%, 85%, 90%, 95%, 96%, 97%, 98%, or 99%) identical to amino acid residues 1-32 of human HNF-1α (SEQ ID NO:1). In some embodiments, a dimerization domain of the present invention has a sequence that is substantially identical to amino acid residues 1-32 of human HNF-1α (SEQ ID NO:1). In some embodiments, a dimerization domain of the present invention comprises amino acid residues 1-32 of human HNF-1α (SEQ ID NO:1). In some embodiments, a dimerization domain of the present invention is amino acid residues 1-32 of human HNF-1α (SEQ ID NO:1).

In some embodiments, a bispecific binding agent of the present invention has a sequence at least about 50% (e.g., at least about 55%, 60%, 65%, 70%, 75%, 80%, 85%, 90%, 95%, 96%, 97%, 98%, or 99%) identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a bispecific binding agent of the present invention has a sequence that is substantially identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a bispecific binding agent of the present invention has a sequence that is identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a bispecific binding agent of the present invention comprises a sequence that is selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23.

In some embodiments, a pharmaceutical composition comprising a bispecific binding agent of the present invention and a pharmaceutically acceptable carrier is provided.

In some embodiments, a fusion protein is provided, comprising, from 5'-3', a first antibody component, a second antibody component, and a dimerization component comprising a human hepatocyte nuclear factor-1 alpha (HNF-1α) element. In some embodiments, a human HNF-1α element comprises amino acid residues 1-32 of human HNF-1α.

In some embodiments, first and second antibody components of a fusion protein of the present invention are single chain variable fragments (scFvs).

In some embodiments, a first scFv of a fusion protein of the present invention binds to a tumor antigen. In some embodiments, a first scFv of a fusion protein of the present invention binds to a tumor antigen that is GD2. In some embodiments, a first scFv of a fusion protein of the present invention binds to a tumor antigen that is GD3.

In some embodiments, a second scFv of a fusion protein of the present invention binds to an antigen present on T cells. In some embodiments, a second scFv of a fusion protein of the present invention binds to an antigen present on T cells that is CD3.

In some embodiments, a fusion protein of the present invention has a sequence at least about 50% (e.g., at least about 55%, 60%, 65%, 70%, 75%, 80%, 85%, 90%, 95%, 96%, 97%, 98%, or 99%) identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a fusion protein of the present invention has a sequence that is substantially identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a fusion protein of the present invention has a sequence that is identical to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

In some embodiments, a fusion protein of the present invention comprises a sequence that is selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23.

In some embodiments, a dimeric bispecific binding agent comprised of two fusion proteins of the present invention is provided.

In some embodiments, a pharmaceutical composition comprising a dimeric bispecific binding agent that is comprised of two fusion proteins of the present invention and a pharmaceutically acceptable carrier is provided.

In some embodiments, a nucleic acid sequence encoding a fusion protein of the present invention is provided.

In some embodiments, a vector comprising a nucleic acid sequence of the present invention is provided.

In some embodiments, a host cell comprising a vector of the present invention is provided. In some embodiments, a host cell of the present invention is selected from the group consisting of a bacterial, yeast, insect, or mammalian cell. In some embodiments, a host cell of the present invention is selected from the group consisting of *E. coli, Pichia pastoris*, Sf9, COS, HEK293 and a CHO cell.

In some embodiments, a method of producing a dimeric bispecific binding agent of the present invention is provided, the method comprising culturing a host cell containing a vector comprising a nucleic acid sequence that encodes a fusion protein of the present invention under conditions suitable for expression of the dimeric bispecific binding agent, and recovering the dimeric bispecific binding agent.

In some embodiments, in method of providing a high affinity bispecific antibody composition comprising a bispecific antibody agent that includes first and second antibody components, an improvement is provided, said improvement comprises providing at least one of such first and second antibody components as a fusion with a dimerization component comprised of a human HNF-1α dimerization element, so that the antibody component-dimerization component fusion is capable of forming a homodimer. In some embodiments, a dimerization component of the present invention comprises amino acid residues 1-32 of human HNF-1α.

In some embodiments, a method of killing tumor cells is provided, the method comprising steps of contacting the tumor cells with a bispecific binding agent, comprised of two fusion proteins that each comprise, from 5' to 3', a first antibody component that binds to a tumor antigen, a second antibody component that binds to CD3 on T cells, and a dimerization component comprising a human HNF-1α element, such that the bispecific binding agent is capable of dimerization to form a homodimer, the contacting being performed under conditions and for a time sufficient that T cells to which the homodimer has bound mediate killing of the tumor cells. In some embodiments, a dimerization component of the present invention comprises amino acid residues 1-32 of human HNF-1α. In some embodiments, a first and second antibody component of a bispecific binding agent of the present invention are single chain variable fragments (scFvs). In some embodiments, a tumor antigen of the present invention is GD2. In some embodiments, a tumor antigen of the present invention is GD3.

In some embodiments, a method of inhibiting tumor growth is provided, the method comprising steps of contacting a tumor with a bispecific binding agent, comprised of two fusion proteins that each comprise, from 5' to 3', a first antibody component that binds to a tumor antigen, a second antibody component that binds to CD3 on T cells, and a dimerization component comprising a human HNF-1α element, such that the bispecific antibody is capable of dimerization to form a homodimer, the contacting being performed under conditions and for a time sufficient that T cells to which the homodimer has bound inhibit growth of a tumor. In some embodiments, a dimerization domain of the present comprises amino acid residues 1-32 of human HNF-1α. In some embodiments, a first and second antibody component of a bispecific binding agent of the present invention are single chain variable fragments (scFvs). In some embodiments, a tumor antigen of the present invention is GD2. In some embodiments, a tumor antigen of the present invention is GD3.

In some embodiments, a bispecific binding agent is provided, comprised of two fusion proteins that each comprise, from 5' to 3', a first antibody component that binds to a tumor antigen, a second antibody component that binds to CD3 on T cells, and a dimerization component comprising a human HNF-1α element, such that the bispecific binding agent is capable of dimerization to form a homodimer; wherein the homodimer is characterized by a longer half-life as compared to an otherwise comparable bispecific binding agent that does not comprise the dimerization component. In some embodiments, a dimerization component of the present invention comprises amino acid residues 1-32 of human HNF-1α. In some embodiments, a first and second antibody component of a bispecific binding agent of the present invention are single chain variable fragments (scFvs). In some embodiments, a tumor antigen of the present invention is GD2. In some embodiments, a tumor antigen of the present invention is GD3.

BRIEF DESCRIPTION OF THE DRAWING

The Drawing included herein, which is comprised of the following Figures, is for illustration purposes only not for limitation.

DETAILED DESCRIPTION OF CERTAIN EMBODIMENTS

Figure 1:
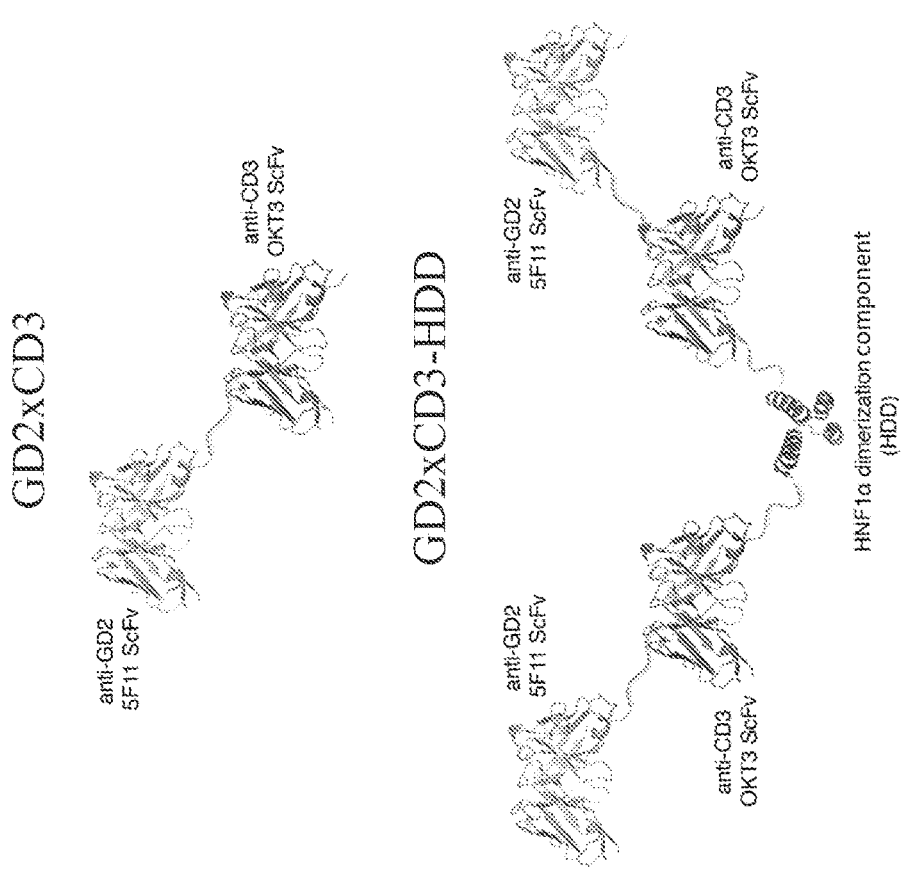
FIG. 1 shows schematic illustrations, not to scale, of scFv$_{5F11}$-scFv$_{OKT3}$ (GD2×CD3) and dimeric scFv$_{5F11}$-scFv$_{OKT3}$-HDD bispecific binding agents.

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art. Although any methods and materials similar or equivalent to those described herein can be used in the practice or testing of the present invention, the preferred methods and materials are now described. All publications mentioned herein are incorporated herein by reference.

Definitions

In order for the present invention to be more readily understood, certain terms are first defined below. Additional definitions for the following terms and other terms are set forth through the specification.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

"Affinity matured" (or "affinity matured antibody"), as used herein, refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al. Bio-Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7): 3310-9 (1995); and Hawkins et al, J. Mol. Biol. 226:889-896 (1992).

"Antibody", as used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., $IgG_1$, $IgG_2$, $IgG_3$, $IgG_4$, $IgA_1$ and $IgA_2$) or subclass.

"Antibody component", as used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody binding region (e.g., an antibody light chain or variable region or one or more complementarity determining regions ("CDRs") thereof, or an antibody heavy chain or variable region or one more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain which is homologous or largely homologous to an immunoglobulin-binding domain. In particular embodiments, an included "antibody component" encompasses polypeptides having a binding domain that shows at least 99% identity with an immunoglobulin binding domain. In some embodiments, an included "antibody component" is any polypeptide having a binding domain that shows at least 70%, 75%, 80%, 85%, 90%, 95% or 98% identity with an immunoglobulin binding domain, for example a reference immunoglobulin binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and $C_L$ domains; (ii) a $F(ab')_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5). In some embodiments, an antibody component is or comprises a single chain "linear antibody" comprising a pair of tandem Fv segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870). In some embodiments, an antibody component may have structural elements characteristic of chimeric or humanized antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

"Biological activity", as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

"Bispecific antibody", as used herein, refers to a bispecific binding agent in which at least one, and typically both, of the binding moieties is or comprises an antibody component. A variety of different bi-specific antibody structures is known in the art. In some embodiments, each binding moiety in a bispecific antibody that is or comprises an antibody component includes $V_H$ and/or $V_L$ regions; in some such embodiments, the $V_H$ and/or $V_L$ regions are those found in a particular monoclonal antibody. In some embodiments, where the bispecific antibody contains two antibody component binding moieties, each includes $V_H$ and/or $V_L$ regions from different monoclonal antibodies.

"Bispecific binding agent", as used herein, refers to a polypeptide agent with two discrete binding moieties, each of which binds with a distinct target. In some embodiments, a bispecific binding agent is a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) the same target (e.g., antigen); in some embodiments, they recognize different targets. In some embodiments, a bispecific binding agent is capable of binding simultaneously to two targets which are of different structure.

"Carrier", as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

"CDR", as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Boundaries of CDRs have been defined differently depending on the system, of which several are known in the art (e.g., Kabat, Chothia, etc.).

"CDR-grafted antibody", as used herein, refers to an antibody whose amino acid sequence comprises heavy and light chain variable region sequences from one species but in which the sequences of one or more of the CDR regions of $V_H$ and/or $V_L$ are replaced with CDR sequences of another species, such as antibodies having murine $V_H$ and $V_L$ regions in which one or more of the murine CDRs (e.g., CDR3) has been replaced with human CDR sequences. Likewise, a "CDR-grafted antibody" may also refer to antibodies having human $V_H$ and $V_L$ regions in which one or more of the human CDRs (e.g., CDR3) has been replaced with mouse CDR sequences.

"Chimeric antibody", as used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody".

"Comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Dimerization component", as used herein, refers to a polypeptide element that, when included in a polypeptide chain, mediates non-covalent association of that chain with one or more other polypeptides also containing the dimerization component into a higher-order complex. Where the interacting polypeptide chains have identical sequences, the resulting associated higher order complex is referred to as a "homodimer" (or "homomultimer" if more than two chains are involved); where the interacting polypeptide chains have different sequences, the resulting associated complex is referred to as a "heterodimer" (or "heteromultimer"). In some embodiments, a dimerization component is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length.

As described herein, a number of potential dimerization components are known in the art. In some embodiments, a dimerization component may include a site for covalent association, for example, by disulfide bond formation. In certain embodiments, a dimerization component for use in accordance with the present invention is or comprises an element found in human HNF-1α that mediates dimerization when introduced into a polypeptide other than HNF-1α.

"Epitope", as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

"Excipient", as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

"Framework" or "framework region", as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

"Host cell", as used herein, refers to a cell into which exogenous DNA (recombinant or otherwise) has been introduced. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

"Human antibody", as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

"Humanized", as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

"Isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

"$K_D$", as used herein, refers to the dissociation constant of a binding agent (e.g., an antibody or binding component thereof) from a complex with its partner (e.g., the epitope to which the antibody or binding component thereof binds).

"$K_{off}$", as used herein, refers to the off rate constant for dissociation of a binding agent (e.g., an antibody or binding component thereof) from a complex with its partner (e.g., the epitope to which the antibody or binding component thereof binds).

"$K_{on}$", as used herein, refers to the on rate constant for association of a binding agent (e.g., an antibody or binding component thereof) with its partner (e.g., the epitope to which the antibody or binding component thereof binds).

"Linker", as used herein, is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2:1121-1123).

"Multivalent binding agent", as used herein, refers a binding agent capable of binding to two or more antigens, which can be on the same molecule or on different molecules. Multivalent binding agents as described herein are, in some embodiments, engineered to have the three or more antigen binding sites, and are typically not naturally occurring proteins. Multivalent binding agents as described herein refer to binding agents capable of binding two or more related or unrelated targets. Multivalent binding agents may be composed of multiple copies of a single antibody component or multiple copies of different antibody components. Such binding agents are capable of binding to two or more antigens and are tetravalent or multivalent binding agents. Multivalent binding agents may additionally comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, or a hapten and/or an antigen or epitope. In many embodiments, multivalent binding agents of the present invention are proteins engineered to have characteristics of multivalent binding agents as described herein. Multivalent binding agents of the present invention may be monospecific (capable of binding one antigen) or multispecific (capable of binding two or more antigens), and may be composed of two heavy chain polypeptides and two light chain polypeptides. Each binding site, in some embodiments, is composed of a heavy chain variable domain and a light chain variable domain with a total of six CDRs involved in antigen binding per antigen binding site.

"Nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

"Operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

"Physiological conditions", as used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

"Recombinant", as used herein, is intended to refer to polypeptides (e.g., antibodies or antibody components, or multi-specific binding agents as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

"Recovering", as used herein, refers to the process of rendering an agent or entity substantially free of other previously-associated components, for example by isolation, e.g., using purification techniques known in the art. In some embodiments, an agent or entity is recovered from a natural source and/or a source comprising cells.

"Specific binding", as used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

"Subject", as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial sequence homology": The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution. Typical amino acid categorizations are summarized in Table 1 and 2.

TABLE 1

| Alanine | Ala | A | nonpolar | neutral | 1.8 |
|---|---|---|---|---|---|
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |

TABLE 1-continued

| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

"Substantial identity": The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

"Surface plasmon resonance", as used herein, refers to an optical phenomenon that allows for the analysis of specific binding interactions in real-time, for example through detection of alterations in protein concentrations within a biosensor matrix, such as by using a BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

"Therapeutically effective amount", as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

"Transformation", as used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

"Vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Multivalent Binding Agents

As those skilled in the art are aware, a multivalent binding agent is a molecular entity or complex that includes binding components that bind specifically to two or more targets (e.g., epitopes). Such multivalent binding agents find a variety of uses in the art, including therapeutic uses. To give but one example, as those skilled in the art are aware, multivalent binding agents have been engineered to facilitate killing of tumor cells by directing (or recruiting) cytotoxic T cells to a tumor site. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

The potential efficacy of multispecific binding agents that engage T cells lies in the ability of these agents to direct T cells to a tumor site for T-cell mediated killing. T cells are the most potent effector cells in the immune system at killing aberrant cells and are not capable of Fc-mediated antibody dependent cellular cytotoxicity (ADCC). The mechanism by which such multivalent binding agents direct T cells to a tumor site is through binding of a tumor antigen on the surface of a tumor and a co-receptor on the surface of T cells, CD3. CD3 is a complex of three chains ($\gamma$, $\delta$, and $\epsilon$) expressed on the surface of all mature T cells. Expression of CD3 is almost exclusively restricted to T cells. The anti-CD3 component of a bispecific binding agent can transform a previously unstimulated and uncommitted nonclonal T cell to become potent serial killer of tumor cells (Wolf et al., 2005, Drug Discov Today 10: 1237-1244). Binding agents of this type have demonstrated efficacy in animal xenograft studies of solid tumors expressing the epithelial cell adhesion molecule (EpCAM) antigens in addition to other targets (Bargou et al., supra; Brischwein et al., 2006, Mol Immunol 43: 1129-1143; Baeuerle and Reinhardt, 2009, Cancer Res 69: 4941-4944).

In some embodiments, multivalent binding agents for use in accordance with the present invention are bispecific binding agents. In many embodiments, such bispecific binding agents are capable of binding to T cells. In many embodiments, such bispecific binding agents are capable of binding to CD3 on T cells.

In some embodiments, multivalent or bispecific binding agents for use in accordance with the present invention are or comprise antibody components. A variety of technologies are known in the art for designing, constructing, and/or producing multispecific or bispecific binding agents comprising antibody components.

For example, bispecific binding agents have been constructed that either utilize the full immunoglobulin framework (e.g., IgG), single chain variable fragment (scFv), or combinations thereof. Bispecific binding agents composed of two scFv units in tandem has been shown to be one of the most clinically successful bispecific antibody formats. In the case of anti-tumor immunotherapy, bispecific binding agents that comprise two single chain variable fragments (scFvs) in tandem have been designed such that an scFv that binds a tumor antigen is linked with an scFv that engages T cells by binding CD3. In this way, T cells are recruited to a tumor site in the hope that they can mediate killing of the tumor cells making up the tumor by the cytotoxic properties that certain T cells have. An example of such a bispecific binding agent has been made that targets CD19 and CD3 for lymphoma (termed Bispecific T cell Engaging, or BiTE; e.g., see Dreier et al., 2003, J Immunol 170: 4397-4402; Bargou et al., 2008, Science 321: 974-977), which has been successful in preventing tumor growth in animal xenograft studies. In human studies, this bispecific binding agent demonstrated objective tumor response, including five partial and two complete remissions.

Exemplary bispecific binding agents include those with a first antibody component specific for a tumor antigen and a second antibody component specific for a cytotoxic marker, e.g., an Fc receptor (e.g., Fc$\gamma$RI, Fc$\gamma$RII, Fc$\gamma$RIII, etc.) or a T cell marker (e.g., CD3, CD28, etc.). Further, the second antibody component can be substituted with an antibody component having a different desired specificity. For example, a bispecific binding agent with a first antibody component specific for a tumor antigen and a second antibody component specific for a toxin can be paired so as to deliver a toxin (e.g., saporin, vinca alkaloid, etc.) to a tumor cell. Other exemplary bispecific binding agents include those with a first antibody component specific for an activating receptor (e.g., B cell receptor, Fc$\gamma$RI, Fc$\gamma$RIIA, Fc$\gamma$RIIIA, Fc$\gamma$RI, T cell receptor, etc.) and a second antibody component specific for an inhibitory receptor (e.g., Fc$\gamma$RIIB, CD5, CD22, CD72, CD300a, etc.). Yet another example includes a second antibody component specific to a different antigen on the same cell type for which a first antibody component is specific, for example, CD20, CD19, CD21, CD23, CD46, CD80, HLA-DR, CD74, MUC1, and CD22 on B-cells. Such bispecific binding agents can be constructed for therapeutic conditions associated with cell activation (e.g. allergy and asthma). Bispecific binding agents can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is mono-valent for each antigen to which it binds.

In some embodiments, bispecific binding agents of the present invention are characterized by the ability to can bind simultaneously to two targets which are of different structure. In some embodiments, bispecific binding agents of the present invention have at least one component that specifically binds to, for example, a B-cell, T-cell, myeloid, plasma, or a mast cell antigen or epitope and at least one other component that specifically binds to a targetable conjugate that bears a therapeutic or diagnostic agent.

Typically, antibodies that bind to carbohydrate antigens, such as GD2, are generally of low affinity. Thus, the use of stable non-immunogenic peptide sequences as described herein to induce homodimerization presents a unique approach to enhance T cell targeting for cancer immunotherapy. Additionally, dimerization of bispecific binding proteins of the present invention, which are composed of tandem antibody components (e.g., scFvs) that are about 50-55 kDa in monomeric form, substantially increases serum half-life and potential therapeutic efficacy regardless of tumor affinity.

The tumor antigen GD2 is highly expressed in several metastatic cancer types, and there are currently no effective treatments. Anti-GD2 antibodies have proven safe and effective in randomized trials, however, complement mediated acute pain during antibody infusion has been reported as a major drawback (Yang et al., 2010, Drugs Future 35(8):665). Bispecific binding proteins as described herein are capable of bivalent binding without the presence of an Fc, a component of traditional antibodies. Such bivalency results from the use of a dimerization component that does not induce complement activation. As such, the strategy for dimerization of the bispecific binding proteins as described represents a unique approach for enhanced tumor killing, reduced adverse effects, and demonstrates a for a potent therapeutic for the treatment of several GD2-positive cancers.

Dimerization Components

The present invention provides the insight that exemplary properties of multispecific binding agents (and particularly of bispecific binding agents such as bispecific antibodies) as described herein are particularly useful in, and/or provide particular advantages in certain in vivo applications when coupled with a dimerization component. For example, among other things, the present invention encompasses the recognition that multispecific binding agents that are constructed to be capable of dimerization as described herein provide an increase in the functional affinity of the multispecific binding agent to its target(s). In particular, the various Examples presented herein demonstrate improved properties of a bispecific antibody dimer (comprised of two fusion polypeptides, each of which includes first and second antibody components and a dimerization component) as compared with its corresponding monomer polypeptides lacking the dimerization component. The particular exemplified bispecific antibody dimer targeted disialoganglioside GD2 and CD3; in some embodiments, as demonstrated, the dimer is characterized by an enhanced potency to elicit tumor cell destruction by T cells.

In some embodiments, the present invention encompasses the recognition, among other things, that use of a dimerization component in the context of a bispecific binding agent can induce bivalent binding of a bispecific binding agent to at least one of its targets. Full-length IgG antibodies utilize bivalent binding, which can enhance the avidity for antigens by orders of magnitude as compared to the monovalent binding characteristic of scFv fragments (Pluckthun and Pack, 1997, Immunotechnol. 3:83-105). The present invention encompasses the recognition that similar, or even greater, avidity improvements can be achieved through introduction of a dimerization component into a bivalent binding agent polypeptide.

In some embodiments, the present invention encompasses the recognition, among other things, that a dimerization component as described herein is suitable to dimerize any engineered protein to which it is attached. In some certain embodiments, an engineered protein includes antibody components, bispecific binding agents or multivalent binding agents. In some embodiments, the present invention provides, among other things, a bispecific binding agent operably linked to a dimerization component, wherein such a dimeric bispecific binding agent is characterized by a greater avidity for at least one target as compared to a bispecific binding agent lacking the dimerization component. In some embodiments, greater avidity is achieved for a therapeutic target, e.g., a tumor antigen. In some embodiments, greater avidity is achieved for an antibody component of a bispecific binding agent as described herein. In some embodiments, a dimerization component as described herein is particularly useful in, and/or provide particular advantages in binding improvements in bispecific binding agents comprising an antibody component that binds disialoganglioside GD2. Exemplary antibody components include those assembled from previously characterized antibodies, such as, for example, 5F11 and 3F8.

A variety of dimerization component sequences that can be used in accordance with the present invention are known in the art (see, for example, Pluckthun and Pack, supra; Cuesta et al., 2010, Trends Biotechnol. 28: 355-362). Some particular examples of such components include synthetic or yeast peptides that helix bundles or coiled-coils (Table 3).

TABLE 3

| Type | Examples |
| --- | --- |
| Helix self-associating peptides | single or helix-turn-helix |
| Coiled coils (leucine zippers) | GCN4, ZIP, TETRAZIP, Jun/Fos |
| Human proteins | p53, human collagen XVIII NC1 |
| Cytokines | TNFα, IL-12 |
| Bacterial proteins | Streptavidin, alkaline phosphatase, barnase-barstar |
| Immunoglobulin constant regions | Fc, $C_L$-$C_H1$, $C_H3$-$C_H3$, hinge |
| Protein-protein interactions | Protein kinase A-A kinase anchoring protein ("Dock and Lock") |
| Amino acid substitution | Substitution of corresponding amino acids in Fc of antibody based on size ("knobs-into-holes") |

The present invention specifically encompasses the finding that a particularly useful dimerization component for incorporation into multivalent binding agents, and particularly into bivalent antibodies, is or comprises a dimerization element of human hepatocyte nuclear factor-1 alpha (HNF-1α).

HNF-1α is composed of four regions: an amino-terminal dimerization component, a flexible linker, a bipartite DNA-binding motif, and a carboxy-terminal transactivation component. The flexible linker connects the DNA-binding motif and the dimerization component. HNF-1α is an important regulator of both renal and hepatic gene expression. An exemplary amino acid sequence of residues 1-32 of human HNF-1α shown in SEQ ID NO:1 below.

Human HNF-1α$_{1-32}$
(SEQ ID NO: 1)
MVSKLSQLQTELLAALLESGLSKEALIQALGE

Typically, a dimerization component may be designed or selected with reference to amino acid sequences proteins that are known to self-associate. Examples of such dimerization components known in the art include helix bundles, coiled-coils (e.g., leucine zippers), synthetic peptides, and yeast proteins. The present invention provides the insight of bispecific binding agents that employ a dimerization component comprising an element of human hepatocyte nuclear factor-1α, which has been reported to form a tightly wound four helix bundle (Narayana et al, 2001, J. Mol. Biol. 310:635-658). For example, a dimerization component comprising an element of human HNF-1α may have a sequence that is substantially identical to amino acid residues 1-32 of human HNF-1α (SEQ ID NO: 1). In some embodiments, a dimerization component according to the present invention has a sequence at least about 50% (e.g., at least about 55%, 60%, 65%, 70%, 75%, 80%, 85%, 90%, 95%, 96%, 97%, 98%, or 99%) to amino acid residues 1-32 of human HNF-1α (SEQ ID NO: 1).

Exemplary bispecific binding agents of the present invention are shown in Table 4. Exemplary antibody variable regions of the present invention are underlined. An exemplary dimerization component of the present invention is shown in italics.

TABLE 4

| | |
|---|---|
| 5HLBT (SEQ ID NO: 2) | QVQLQQSGPELVKPGASVKISCKTSGYKFTEYTM HWVKQSHGKSLEWIGGINPNNGGTNYNQKFKGK ATLTVDKSSSTAYMELRSLTSEDSAVYYCARDTT VPFAYWGQGTTVTVSSGGGGSGGGGSGGGGSDIE LTQSPAIMSASPGEKVTMTCSASSSISYMHWYQQ KPGTSPKRWIYDTSKLASGVPARFSGSGSGTSYSL TISSMEAEDAATYYCHQRSSYPLTFGAGTKLEIKR ASTKGPGGGGSGGGGSGGGGS*QVQLVQSGGGVV QPGRSLRLSCKASGYTFTRYTMHWVRQAPGKGL EWIGYINPSRGYTNYNQKFKDRFTISRDNSKNTAF LQMDSLRPEDTGVYFCARYYDDHYCLDYWGQG TPVTVSS*GGGGSGGGGSGGGGSDIQMTQSPSSLSA SVGDRVTITCSASSSVSYMNWYQQTPGKAPKRWI YDTSKLASGVPSRFSGSGSGTDYTFTISSLQPEDIA TYYCQQWSSNPFTFGQGTKLQITR |
| 5LHBT (SEQ ID NO: 3) | DIELTQSPAIMSASPGEKVTMTCSASSSISYMHWY QQKPGTSPKRWIYDTSKLASGVPARFSGSGSGTSY SLTISSMEAEDAATYYCHQRSSYPLTFGAGTKLEI KRGGGGSGGGGSGGGGSQVQLQQSGPELVKPGA SVKISCKTSGYKFTEYTMHWVKQSHGKSLEWIGG INPNNGGTNYNQKFKGKATLTVDKSSSTAYMELR SLTSEDSAVYYCARDTTVPFAYWGQGTTVTVSSA *STKGPGGGGSGGGGSGGGGSQVQLVQSGGGVVQ PGRSLRLSCKASGYTFTRYTMHWVRQAPGKGLE WIGYINPSRGYTNYNQKFKDRFTISRDNSKNTAFL QMDSLRPEDTGVYFCARYYDDHYCLDYWGQGTP VTVSS*GGGGSGGGGSGGGGSDIQMTQSPSSLSAS VGDRVTITCSASSSVSYMNWYQQTPGKAPKRWIY DTSKLASGVPSRFSGSGSGTDYTFTISSLQPEDIAT YYCQQWSSNPFTFGQGTKLQITR |
| 5HLDS$_{15}$BT (SEQ ID NO: 4) | QVQLQQSGPELVKPGASVKISCKTSGYKFTEYTM HWVKQSHGKCLEWIGGINPNNGGTNYNQKFKGK ATLTVDKSSSTAYMELRSLTSEDSAVYYCARDTT VPFAYWGQGTTVTVSSGGGGSGGGGSGGGGSDIE LTQSPAIMSASPGEKVTMTCSASSSISYMHWYQQ KPGTSPKRWIYDTSKLASGVPARFSGSGSGTSYSL TISSMEAEDAATYYCHQRSSYPLTFGCGTKLEIKR ASTKGPGGGGSGGGGSGGGGS*QVQLVQSGGGVV QPGRSLRLSCKASGYTFTRYTMHWVRQAPGKGL EWIGYINPSRGYTNYNQKFKDRFTISRDNSKNTAF LQMDSLRPEDTGVYFCARYYDDHYCLDYWGQG TPVTVSS*GGGGSGGGGSGGGGSDIQMTQSPSSLSA SVGDRVTITCSASSSVSYMNWYQQTPGKAPKRWI YDTSKLASGVPSRFSGSGSGTDYTFTISSLQPEDIA TYYCQQWSSNPFTFGQGTKLQITR |
| 5LHDS$_{15}$BT (SEQ ID NO: 5) | DIELTQSPAIMSASPGEKVTMTCSASSSISYMHWY QQKPGTSPKRWIYDTSKLASGVPARFSGSGSGTSY SLTISSMEAEDAATYYCHQRSSYPLTFGCGTKLEI KRGGGGSGGGGSGGGGSQVQLQQSGPELVKPGA |

TABLE 4-continued

| | |
|---|---|
| | SVKISCKTSGYKFTEYTMHWVKQSHGKCLEWIGG<br>INPNNGGTNYNQKFKGKATLTVDKSSSTAYMELR<br>SLTSEDSAVYYCARDTTVPFAYWGQGTTVTVSSA<br>STKGPGGGSGGGGSGGGGSQVQLVQSGGGVVQ<br>PGRSLRLSCKASGYTFTRYTMHWVRQAPGKGLE<br>WIGYINPSRGYTNYNQKFKDRFTISRDNSKNTAFL<br>QMDSLRPEDTGVYFCARYYDDHYCLDYWGQGTP<br>VTVSSGGGGSGGGGSGGGGSDIQMTQSPSSLSAS<br>VGDRVTITCSASSSVSYMNWYQQTPGKAPKRWIY<br>DTSKLASGVPSRFSGSGSGTDYTFTISSLQPEDIAT<br>YYCQQWSSNPFTFGQGTKLQITR |
| 5HLDS₅BT<br>(SEQ ID NO: 6) | QVQLQQSGPELVKPGASVKISCKTSGYKFTEYTM<br>HWVKQSHGKCLEWIGGINPNNGGTNYNQKFKGK<br>ATLTVDKSSSTAYMELRSLTSEDSAVYYCARDTT<br>VPFAYWGQGTTVTVSSGGGGSDIELTQSPAIMSAS<br>PGEKVTMTCSASSSISYMHWYQQKPGTSPKRWIY<br>DTSKLASGVPARFSGSGSGTSYSLTISSMEAEDAA<br>TYYCHQRSSYPLTFGCGTKLEIKRASTKGPGGGGS<br>GGGGSGGGGSQVQLVQSGGGVVQPGRSLRLSCK<br>ASGYTFTRYTMHWVRQAPGKGLEWIGYINPSRG<br>YTNYNQKFKDRFTISRDNSKNTAFLQMDSLRPED<br>TGVYFCARYYDDHYCLDYWGQGTPVTVSSGGGG<br>SGGGGSGGGGSDIQMTQSPSSLSASVGDRVTITCS<br>ASSSVSYMNWYQQTPGKAPKRWIYDTSKLASGV<br>PSRFSGSGSGTDYTFTISSLQPEDIATYYCQQWSSN<br>PFTFGQGTKLQITR |
| 5LHDS₅BT<br>(SEQ ID NO: 7) | DIELTQSPAIMSASPGEKVTMTCSASSSISYMHWY<br>QQKPGTSPKRWIYDTSKLASGVPARFSGSGSGTSY<br>SLTISSMEAEDAATYYCHQRSSYPLTFGCGTKLEI<br>KRGGGGSQVQLQQSGPELVKPGASVKISCKTSGY<br>KFTEYTMHWVKQSHGKCLEWIGGINPNNGGTNY<br>NQKFKGKATLTVDKSSSTAYMELRSLTSEDSAVY<br>YCARDTTVPFAYWGQGTTVTVSSASTKGPGGGG<br>SGGGGSGGGGSQVQLVQSGGGVVQPGRSLRLSC<br>KASGYTFTRYTMHWVRQAPGKGLEWIGYINPSR<br>GYTNYNQKFKDRFTISRDNSKNTAFLQMDSLRPE<br>DTGVYFCARYYDDHYCLDYWGQGTPVTVSSGGG<br>GSGGGGSGGGGSDIQMTQSPSSLSASVGDRVTITC<br>SASSSVSYMNWYQQTPGKAPKRWIYDTSKLASG<br>VPSRFSGSGSGTDYTFTISSLQPEDIATYYCQQWSS<br>NPFTFGQGTKLQITR |
| Y-BT<br>(SEQ ID NO: 8) | QVQLQQSGPELVKPGASVKISCKTSGYKFTEYTM<br>HWVKQSHGKCLEWIGGINPNNGGTNYNQKFKGK<br>ATLTVDKSSSTAYMELRSLTSEDSAVYYCARDTT<br>VPYAYWGQGTTVTVSSGGGGSGGGGSGGGGSDI<br>ELTQSPAIMSASPGEKVTMTCSASSSISYMHWYQ<br>QKPGTSPKRWIYDTSKLASGVPARFSGSGSGTSYS<br>LTISSMEAEDAATYYCHQRSSYPLTFGCGTKLEIK<br>RASTKGPGGGGSGGGGSGGGGSQVQLVQSGGGV<br>VQPGRSLRLSCKASGYTFTRYTMHWVRQAPGKG<br>LEWIGYINPSRGYTNYNQKFKDRFTISRDNSKNTA<br>FLQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITR |
| Q-BT<br>(SEQ ID NO: 9) | QVQLQQSGPELVKPGASVKISCKTSGYKFTQYTM<br>HWVKQSHGKSLEWIGGINPNNGGTNYNQKFKGK<br>ATLTVDKSSSTAYMELRSLTSEDSAVYYCARDTT<br>VPFAYWGQGTTVTVSSGGGGSGGGGSGGGGSDIE<br>LTQSPAIMSASPGEKVTMTCSASSSISYMHWYQQ<br>KPGTSPKRWIYDTSKLASGVPARFSGSGSGTSYSL<br>TISSMEAEDAATYYCHQRSSYPLTFGAGTKLEIKR<br>ASTKGPGGGSGGGGSGGGGSQVQLVQSGGGVV<br>QPGRSLRLSCKASGYTFTRYTMHWVRQAPGKGL<br>EWIGYINPSRGYTNYNQKFKDRFTISRDNSKNTAF<br>LQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITR |
| Y-BT-HDD<br>(SEQ ID NO: 10) | QVQLQQSGPELVKPGASVKISCKTSGYKFTEYTM<br>HWVKQSHGKCLEWIGGINPNNGGTNYNQKFKGK<br>ATLTVDKSSSTAYMELRSLTSEDSAVYYCARDTT<br>VPYAYWGQGTTVTVSSGGGGSGGGGSGGGGSDI |

TABLE 4-continued

| | |
|---|---|
| | ELTQSPAIMSASPGEKVTMTCSASSSISYMHWYQ<br>QKPGTSPKRWIYDTSKLASGVPARFSGSGSTSYS<br>LTISSMEAEDAATYYCHQRSSYPLTFGCGTKLEIK<br>RASTKGPGGGSGGGGSGGGGSQVQLVQSGGGV<br>VQPGRSLRLSCKASGYTFTRYTMHWVRQAPGKG<br>LEWIGYINPSRGYTNYNQKFKDRFTISRDNSKNTA<br>FLQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITRTPLGDTTHTSG<br>*MVSKLSQLQTELLAALLESGLSKEALIQALGE*GSGGA<br>P |
| 3LHBT-HDD<br>(SEQ ID NO: 11) | EIVMTQTPATLSVSAGERVTITCKASQSVSNDVTW<br>YQQKPGQAPRLLIYSASNRYSGVPARFSGSGYGTE<br>FTFTISSVQSEDFAVYFCQQDYSSFGQGTKLEIKRG<br>GGGSGGGGSGGGGSQVQLVESGPGVVQPGRSLRI<br>SCAVSGFSVTNYGVHWVRQPPGKGLEWLGVIWA<br>GGITNYNSAFMSRLTISKDNSKNTVYLQMNSLRA<br>EDTAMYYCASRGGHYGYALDYWGQGTLVTVSS<br>ASTKGPGGGSGGGGSGGGGSQVQLVQSGGGVV<br>QPGRSLRLSCKASGYTFTRYTMHWVRQAPGKGL<br>EWIGYINPSRGYTNYNQKFKDRFTISRDNSKNTAF<br>LQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITRTPLGDTTHTSG<br>*MVSKLSQLQTELLAALLESGLSKEALIQALGE*GSGGA<br>P |
| 3LHBT$_{(D32H)}$-HDD<br>(SEQ ID NO: 12) | EIVMTQTPATLSVSAGERVTITCKASQSVSNHVTW<br>YQQKPGQAPRLLIYSASNRYSGVPARFSGSGYGTE<br>FTFTISSVQSEDFAVYFCQQDYSSFGQGTKLEIKRG<br>GGGSGGGGSGGGGSQVQLVESGPGVVQPGRSLRI<br>SCAVSGFSVTNYGVHWVRQPPGKGLEWLGVIWA<br>GGITNYNSAFMSRLTISKDNSKNTVYLQMNSLRA<br>EDTAMYYCASRGGHYGYALDYWGQGTLVTVSS<br>ASTKGPGGGSGGGGSGGGGSQVQLVQSGGGVV<br>QPGRSLRLSCKASGYTFTRYTMHWVRQAPGKGL<br>EWIGYINPSRGYTNYNQKFKDRFTISRDNSKNTAF<br>LQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITRTPLGDTTHTSG<br>*MVSKLSQLQTELLAALLESGLSKEALIQALGE*GSGGA<br>P |
| 3LHBT$_{(E1K, D32H)}$-HDD<br>(SEQ ID NO: 13) | KIVMTQTPATLSVSAGERVTITCKASQSVSNHVT<br>WYQQKPGQAPRLLIYSASNRYSGVPARFSGSGYG<br>TEFTFTISSVQSEDFAVYFCQQDYSSFGQGTKLEIK<br>RGGGGSGGGGSGGGGSQVQLVESGPGVVQPGRS<br>LRISCAVSGFSVTNYGVHWVRQPPGKGLEWLGVI<br>WAGGITNYNSAFMSRLTISKDNSKNTVYLQMNSL<br>RAEDTAMYYCASRGGHYGYALDYWGQGTLVTV<br>SSASTKGPGGGSGGGGSGGGGSQVQLVQSGGG<br>VVQPGRSLRLSCKASGYTFTRYTMHWVRQAPGK<br>GLEWIGYINPSRGYTNYNQKFKDRFTISRDNSKNT<br>AFLQMDSLRPEDTGVYFCARYYDDHYCLDYWGQ<br>GTPVTVSSGGGGSGGGGSGGGGSDIQMTQSPSSLS<br>ASVGDRVTITCSASSSVSYMNWYQQTPGKAPKR<br>WIYDTSKLASGVPSRFSGSGSGTDYTFTISSLQPED<br>IATYYCQQWSSNPFTFGQGTKLQITRTPLGDTTHT<br>SG*MVSKLSQLQTELLAALLESGLSKEALIQALGE*GSG<br>GAP |
| 3LHBT$_{(E1K, D32H, G54I)}$-HDD<br>(SEQ ID NO: 14) | KIVMTQTPATLSVSAGERVTITCKASQSVSNHVT<br>WYQQKPGQAPRLLIYSASNRYSGVPARFSGSGYG<br>TEFTFTISSVQSEDFAVYFCQQDYSSFGQGTKLEIK<br>RGGGGSGGGGSGGGGSQVQLVESGPGVVQPGRS<br>LRISCAVSGFSVTNYGVHWVRQPPGKGLEWLGVI<br>WAIGITNYNSAFMSRLTISKDNSKNTVYLQMNSL<br>RAEDTAMYYCASRGGHYGYALDYWGQGTLVTV<br>SSASTKGPGGGSGGGGSGGGGSQVQLVQSGGG<br>VVQPGRSLRLSCKASGYTFTRYTMHWVRQAPGK<br>GLEWIGYINPSRGYTNYNQKFKDRFTISRDNSKNT<br>AFLQMDSLRPEDTGVYFCARYYDDHYCLDYWGQ<br>GTPVTVSSGGGGSGGGGSGGGGSDIQMTQSPSSLS |

TABLE 4-continued

| | |
|---|---|
| | ASVGDRVTITCSASSSVSYMNWYQQTPGKAPKR<br>WIYDTSKLASGVPSRFSGSGSGTDYTFTISSLQPED<br>IATYYCQQWSSNPFTFGQGTKLQITRTPLGDTTHT<br>SGMVSKLSQLQTELLAALLESGLSKEALIQALGEGSG<br>GAP |
| 3LHBT$_{v5}$-HDD<br>(SEQ ID NO: 15) | EIVMTQTPATLSVSAGERVTITCRASQSVSNDVTW<br>YQQKPGQAPRLLIYSASNRYTGIPARFSGSGYGTE<br>FTFTISSVQSEDFAVYFCQQDYSSFGQGTKLEIKRG<br>GGGSGGGGSGGGGSQVQLVESGPGVVQPGRSLR<br>LSCAVSGFSVTNYGVHWVRQPPGKGLEWLGVIW<br>AGGITNYNSSVKGRLTISKDNSKNTVYLQMNSLR<br>AEDTAVYYCASRGGHYGYALDYWGQGTLVTVSS<br>ASTKGPGGGSGGGGSGGGGSQVQLVQSGGGVV<br>QPGRSLRLSCKASGYTFTRYTMHWVRQAPGKGL<br>EWIGYINPSRGYTNYNQKFKDRFTISRDNSKNTAF<br>LQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITRTPLGDTTHTSG<br>MVSKLSQLQTELLAALLESGLSKEALIQALGEGSGGA<br>P |
| 3LHBT$_{v5(D32H)}$-HDD<br>(SEQ ID NO: 16) | EIVMTQTPATLSVSAGERVTITCRASQSVSNHVTW<br>YQQKPGQAPRLLIYSASNRYTGIPARFSGSGYGTE<br>FTFTISSVQSEDFAVYFCQQDYSSFGQGTKLEIKRG<br>GGGSGGGGSGGGGSQVQLVESGPGVVQPGRSLR<br>LSCAVSGFSVTNYGVHWVRQPPGKGLEWLGVIW<br>AGGITNYNSSVKGRLTISKDNSKNTVYLQMNSLR<br>AEDTAVYYCASRGGHYGYALDYWGQGTLVTVSS<br>ASTKGPGGGSGGGGSGGGGSQVQLVQSGGGVV<br>QPGRSLRLSCKASGYTFTRYTMHWVRQAPGKGL<br>EWIGYINPSRGYTNYNQKFKDRFTISRDNSKNTAF<br>LQMDSLRPEDTGVYFCARYYDDHYCLDYWGQG<br>TPVTVSSGGGGSGGGGSGGGGSDIQMTQSPSSLSA<br>SVGDRVTITCSASSSVSYMNWYQQTPGKAPKRWI<br>YDTSKLASGVPSRFSGSGSGTDYTFTISSLQPEDIA<br>TYYCQQWSSNPFTFGQGTKLQITRTPLGDTTHTSG<br>MVSKLSQLQTELLAALLESGLSKEALIQALGEGSGGA<br>P |
| 3LHBT$_{v5(E1K, D32H)}$-HDD<br>(SEQ ID NO: 17) | KIVMTQTPATLSVSAGERVTITCRASQSVSNHVT<br>WYQQKPGQAPRLLIYSASNRYTGIPARFSGSGYGT<br>EFTFTISSVQSEDFAVYFCQQDYSSFGQGTKLEIKR<br>GGGGSGGGGSGGGGSQVQLVESGPGVVQPGRSL<br>RLSCAVSGFSVTNYGVHWVRQPPGKGLEWLGVI<br>WAGGITNYNSSVKGRLTISKDNSKNTVYLQMNSL<br>RAEDTAVYYCASRGGHYGYALDYWGQGTLVTV<br>SSASTKGPGGGSGGGGSGGGGSQVQLVQSGGG<br>VVQPGRSLRLSCKASGYTFTRYTMHWVRQAPGK<br>GLEWIGYINPSRGYTNYNQKFKDRFTISRDNSKNT<br>AFLQMDSLRPEDTGVYFCARYYDDHYCLDYWGQ<br>GTPVTVSSGGGGSGGGGSGGGGSDIQMTQSPSSLS<br>ASVGDRVTITCSASSSVSYMNWYQQTPGKAPKR<br>WIYDTSKLASGVPSRFSGSGSGTDYTFTISSLQPED<br>IATYYCQQWSSNPFTFGQGTKLQITRTPLGDTTHT<br>SGMVSKLSQLQTELLAALLESGLSKEALIQALGEGSG<br>GAP |
| 3LHBT$_{v5(E1K, D32H, G54I)}$-HDD<br>(SEQ ID NO: 18) | KIVMTQTPATLSVSAGERVTITCRASQSVSNHVT<br>WYQQKPGQAPRLLIYSASNRYTGIPARFSGSGYGT<br>EFTFTISSVQSEDFAVYFCQQDYSSFGQGTKLEIKR<br>GGGGSGGGGSGGGGSQVQLVESGPGVVQPGRSL<br>RLSCAVSGFSVTNYGVHWVRQPPGKGLEWLGVI<br>WAIGITNYNSSVKGRLTISKDNSKNTVYLQMNSL<br>RAEDTAVYYCASRGGHYGYALDYWGQGTLVTV<br>SSASTKGPGGGSGGGGSGGGGSQVQLVQSGGG<br>VVQPGRSLRLSCKASGYTFTRYTMHWVRQAPGK<br>GLEWIGYINPSRGYTNYNQKFKDRFTISRDNSKNT<br>AFLQMDSLRPEDTGVYFCARYYDDHYCLDYWGQ<br>GTPVTVSSGGGGSGGGGSGGGGSDIQMTQSPSSLS<br>ASVGDRVTITCSASSSVSYMNWYQQTPGKAPKR<br>WIYDTSKLASGVPSRFSGSGSGTDYTFTISSLQPED<br>IATYYCQQWSSNPFTFGQGTKLQITRTPLGDTTHT<br>SGMVSKLSQLQTELLAALLESGLSKEALIQALGEGSG<br>GAP |

TABLE 4-continued

641HLBT-HDD
(SEQ ID NO: 19)

EVTLVESGGDFVKPGGSLKVSCAASGFAFSHYAM
SWVRQTPAKRLEWVAYISSGGSGTYYSDSVKGRF
TISRDNAKNTLYLQMRSLRSEDSAMYFCTRVKLG
TYYFDSWGQGTTLTVSSGGGGSGGGGSGGGGSDI
QMTQTASSLPASLGDRVTISCSASQDISNYLNWYQ
QKPDGTVKLLIFYSSNLHSGVPSRFSGGGSGTDYS
LTISNLEPEDIATYFCHQYSKLPWTFGGGTKLEIKR
ASTKGPGGGGSGGGGSGGGGSQVQLVQSGGGVV
QPGRSLRLSCKASGYTFTRYTMHWVRQAPGKGL
EWIGYINPSRGYTNYNQKFKDRFTISRDNSKNTAF
LQMDSLRPEDTGVYFCARYYDDHYCLDYWGQG
TPVTVSSGGGGSGGGGSGGGGSDIQMTQSPSSLSA
SVGDRVTITCSASSSVSYMNWYQQTPGKAPKRWI
YDTSKLASGVPSRFSGSGSGTDYTFTISSLQPEDIA
TYYCQQWSSNPFTFGQGTKLQITRTPLGDTTHTSG
*MVSKLSQLQTELLAALLESGLSKEALIQALGE*GSGGA
P

3LHBT(D32H, G54I)-HDD
(SEQ ID NO: 20)

EIVMTQTPATLSVSAGERVTITCKASQSVSNHVTW
YQQKPGQAPRLLIYSASNRYSGVPARFSGSGYGTE
FTFTISSVQSEDFAVYFCQQDYSSFGQGTKLEIKRG
GGGSGGGGSGGGGSQVQLVESGPGVVQPGRSLRI
SCAVSGFSVTNYGVHWVRQPPGKGLEWLGVIWA
IGITNYNSAFMSRLTISKDNSKNTVYLQMNSLRAE
DTAMYYCASRGGHYGYALDYWGQGTLVTVSSA
STKGPGGGGSGGGGSGGGGSQVQLVQSGGGVVQ
PGRSLRLSCKASGYTFTRYTMHWVRQAPGKGLE
WIGYINPSRGYTNYNQKFKDRFTISRDNSKNTAFL
QMDSLRPEDTGVYFCARYYDDHYCLDYWGQTP
VTVSSGGGGSGGGGSGGGGSDIQMTQSPSSLSAS
VGDRVTITCSASSSVSYMNWYQQTPGKAPKRWIY
DTSKLASGVPSRFSGSGSGTDYTFTISSLQPEDIAT
YYCQQWSSNPFTFGQGTKLQITRTPLGDTTHTSG
*MVSKLSQLQTELLAALLESGLSKEALIQALGE*GSGGA
P

3LHBT(E1K, G54I)-HDD
(SEQ ID NO: 21)

KIVMTQTPATLSVSAGERVTITCKASQSVSNDVT
WYQQKPGQAPRLLIYSASNRYSGVPARFSGSGYG
TEFTFTISSVQSEDFAVYFCQQDYSSFGQGTKLEIK
RGGGGSGGGGSGGGGSQVQLVESGPGVVQPGRS
LRISCAVSGFSVTNYGVHWVRQPPGKGLEWLGVI
WAIGITNYNSAFMSRLTISKDNSKNTVYLQMNSL
RAEDTAMYYCASRGGHYGYALDYWGQGTLVTV
SSASTKGPGGGGSGGGGSGGGGSQVQLVQSGGG
VVQPGRSLRLSCKASGYTFTRYTMHWVRQAPGK
GLEWIGYINPSRGYTNYNQKFKDRFTISRDNSKNT
AFLQMDSLRPEDTGVYFCARYYDDHYCLDYWGQ
GTPVTVSSGGGGSGGGGSGGGGSDIQMTQSPSSLS
ASVGDRVTITCSASSSVSYMNWYQQTPGKAPKR
WIYDTSKLASGVPSRFSGSGSGTDYTFTISSLQPED
IATYYCQQWSSNPFTFGQGTKLQITRTPLGDTTHT
SG*MVSKLSQLQTELLAALLESGLSKEALIQALGE*GSG
GAP

3LHBTv5(D32H, G54I)-HDD
(SEQ ID NO: 22)

EIVMTQTPATLSVSAGERVTITCRASQSVSNHVTW
YQQKPGQAPRLLIYSASNRYTGIPARFSGSGYGTE
FTFTISSVQSEDFAVYFCQQDYSSFGQGTKLEIKRG
GGGSGGGGSGGGGSQVQLVESGPGVVQPGRSLR
LSCAVSGFSVTNYGVHWVRQPPGKGLEWLGVIW
AIGITNYNSSVKGRLTISKDNSKNTVYLQMNSLRA
EDTAVYYCASRGGHYGYALDYWGQGTLVTVSSA
STKGPGGGGSGGGGSGGGGSQVQLVQSGGGVVQ
PGRSLRLSCKASGYTFTRYTMHWVRQAPGKGLE
WIGYINPSRGYTNYNQKFKDRFTISRDNSKNTAFL
QMDSLRPEDTGVYFCARYYDDHYCLDYWGQTP
VTVSSGGGGSGGGGSGGGGSDIQMTQSPSSLSAS
VGDRVTITCSASSSVSYMNWYQQTPGKAPKRWIY
DTSKLASGVPSRFSGSGSGTDYTFTISSLQPEDIAT
YYCQQWSSNPFTFGQGTKLQITRTPLGDTTHTSG
*MVSKLSQLQTELLAALLESGLSKEALIQALGE*GSGGA
P

3LHBTv5(E1K, G54I)-HDD
(SEQ ID NO: 23)

KIVMTQTPATLSVSAGERVTITCRASQSVSNDVT
WYQQKPGQAPRLLIYSASNRYTGIPARFSGSGYGT
EFTFTISSVQSEDFAVYFCQQDYSSFGQGTKLEIKR
GGGGSGGGGSGGGGSQVQLVESGPGVVQPGRSL
RLSCAVSGFSVTNYGVHWVRQPPGKGLEWLGVI
WAIGITNYNSSVKGRLTISKDNSKNTVYLQMNSL
RAEDTAVYYCASRGGHYGYALDYWGQGTLVTV

TABLE 4-continued

```
SSASTKGPGGGGSGGGGSGGGGSQVQLVQSGGG
VVQPGRSLRLSCKASGYTFTRYTMHWVRQAPGK
GLEWIGYINPSRGYTNYNQKFKDRFTISRDNSKNT
AFLQMDSLRPEDTGVYFCARYYDDHYCLDYWGQ
GTPVTVSSGGGGSGGGGSGGGGSDIQMTQSPSSLS
ASVGDRVTITCSASSSVSYMNWYQQTPGKAPKR
WIYDTSKLASGVPSRFSGSGSGTDYTFTISSLQPED
IATYYCQQWSSNPFTFGQGTKLQITRTPLGDTTHT
SGMVSKLSQLQTELLAALLESGLSKEALIQALGEGSG
GAP
```

In various embodiments, bispecific binding agents according to the present invention are composed of a first binding component and a second binding component and a dimerization component. In many embodiments, first and second binding components of a bispecific binding agent as described herein are each composed of antibody components characterized by different specificities. In many embodiments, antibody components are selected from Table 4.

In various embodiments, bispecific binding agents according to the present invention comprise a first binding component, a second binding component and a dimerization component that is connected to the second binding component. In various embodiments, bispecific binding agents according to the present invention comprise a first binding component, a second binding component and a dimerization component that is connected to connected to the first binding component. In various embodiments, bispecific binding agents according to the present invention comprise a first binding component, a second binding component and a dimerization component that is connected to both the first and second binding component (e.g., positioned between the first and second binding components).

In some certain embodiments, bispecific binding agents according to the present invention comprises, from 5' to 3', a first binding component, a second binding component and a dimerization component. In some certain embodiments, bispecific binding agents according to the present invention comprise, from 5' to 3', a dimerization component, a first binding component and a second binding component. In some certain embodiments, bispecific binding agents according to the present invention comprise, from 5' to 3', a first binding component, a dimerization component and a second binding component.

In various embodiments, first and/or second binding components as described herein comprise or are antibody components. In various embodiments, first and/or second binding components as described herein comprise a linker sequence.

In some embodiments, a bispecific binding agent of the present invention has a sequence at least about 50% (e.g., at least about 55%, 60%, 65%, 70%, 75%, 80%, 85%, 90%, 95%, 96%, 97%, 98%, or 99%) identical to a sequence that appears in Table 4.

In some embodiments, a bispecific binding agent of the present invention has a sequence that is substantially identical to a sequence that appears in Table 4.

In some embodiments, a bispecific binding agent of the present invention has a sequence that is identical to a sequence that appears in Table 4.

In some embodiments, a bispecific binding agent of the present invention is selected from a sequence that appears in Table 4.

In various embodiments, a first binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 4.

In various embodiments, a first binding component of a bispecific binding agent as described herein comprises an antibody component having a sequence that is identical to an antibody component that appears in Table 4.

In various embodiments, a second binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 4.

In various embodiments, a second binding component of a bispecific binding agent as described herein comprises an antibody component having a sequence that is identical to an antibody component that appears in Table 4.

In various embodiments, a bispecific binding agent of the present invention has a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to a bispecific binding agent that appears in Table 4.

In various embodiments, a bispecific binding agent of the present invention has a sequence that is identical to a bispecific binding agent that appears in Table 4.

Targets

Among other things, the present invention encompasses the recognition that dimerization of multispecific binding agents, and particularly of bispecific binding agents such as bispecific antibodies, is particularly useful and/or effective to facilitate cell killing. In particular, the present demonstrates that activity of multivalent binding agents that bind specifically to both a target-cell-associated epitope and a lymphocyte-associated epitope can be dramatically increased by introduction of a dimerization domain.

For example, in some embodiments of the present invention, a multivalent binding agent binds specifically to a tumor-cell-associated epitope and a T-cell epitope. In accordance with such embodiments, inclusion of a dimerization domain in the multivalent binding agent can facilitate binding of the agent to one or both of its target epitopes and/or can enhance killing of the target tumor cell as mediated by the target T cell.

In some embodiments, target cells to be killed include, for example, virus-infected cells (e.g., HCV-infected cells, HIV-infected CD4$^+$ T cells, HPV-infected keratinocytes), cells infected with intracellular bacteria or protozoa, and cancer cells. Those of ordinary skill in the art will be aware of appropriate target epitopes on such cells to which multivalent binding agents as described herein desirably bind. Representative such epitopes can be found on antigens such as, for example, envelope proteins, proteases, reverse transcriptase proteins, integrase proteins, etc.

In some embodiments, lymphocyte cells that can mediate killing of target cells as described herein include T cells (e.g., CD8⁺ T cells), natural killer (NK) cells, macrophages, granulocytes and antibody-dependent cytotoxic cells. Those of ordinary skill in the art will be aware of appropriate target epitopes on such lymphocytes to which multivalent binding agents as described herein desirably bind. Representative such epitopes can be found on antigens such as, for example, Fc receptor of IgG (e.g., FcγRIIB), CD1d, CD3, CD4, CD7, CD8, CD13, CD14, CD16, CD31, CD38, CD56, CD68, MAC-1/MAC-3, IL-2Rα, OX40, Ly49, and CD94.

Nucleic Acid Construction and Expression

Multispecific binding agents including dimerization components as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs include regions which encode multispecific binding proteins generated from antibodies and/or antibody components. Typically, such multispecific binding proteins will be generated from $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, humanized or chimeric antibodies.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS or CHO cell). Host cells transformed with an expression vector are grown under conditions permitting production of a fusion protein of the present invention followed by recovery of a multispecific binding agent formed from the fusion proteins.

Multispecific binding agents of the present invention may be purified by any technique, which allows for the subsequent formation of a stable dimer. For example, not wishing to be bound by theory, multispecific binding agents may be recovered from cells either as soluble polypeptides or as inclusion bodies, from which they may be extracted quantitatively by 8M guanidinium hydrochloride and dialysis. In order to further purify multispecific binding agents of the present invention, conventional ion exchange chromatography, hydrophobic interaction chromatography, reverse phase chromatography or gel filtration may be used. Multispecific binding agents of the present invention may also be recovered from conditioned media following secretion from eukaryotic or prokaryotic cells.

Screening and Detection Methods

Multispecific binding agents of the present invention may also be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a multispecific binding agent which is bound to a target molecule (e.g., cell surface antigen). Detectable labels may be used in conjunction with assays using multispecific binding agents of the present invention.

Therapeutic Methods

The ability of the multispecific binding agents of the present invention to exhibit high affinity binding for one of the target antigens makes them therapeutically useful for efficiently targeting cells expressing the target antigen. Thus, it some embodiments, it may be desirable to increase the affinity of a multispecific binding agent for one target antigen and not the other target antigen that is also bound by the multispecific binding agent. For example, in the context of tumor killing, certain conditions may benefit from an increase in affinity to a tumor antigen but not to an antigen on the surface of a cell capable of mediating killing of the tumor (e.g., a T cell). Thus, it may be beneficial to increase the binding affinity of a multispecific binding agent to a tumor antigen in patient having a tumor that expresses the tumor antigen through the use of a multispecific binding agent as described herein.

The present invention provides a multispecific binding agent as described herein as a therapeutic for the treatment of patients having a tumor that expresses an antigen that is capable of being bound by such a multispecific binding agent. Such multispecific binding agents may be used in a method of treatment of the human or animal body, or in a method of diagnosis.

Administration

The present invention provides methods of administering an effective amount of a therapeutic active described herein (e.g., multispecific binding agent) to a subject in need of treatment.

Multispecific binding agents as described herein may be administered through various methods known in the art for the therapeutic delivery of agents, such as proteins or nucleic acids can be used for the therapeutic delivery of an multispecific binding agent or a nucleic acid encoding a multispecific binding agent of the present invention for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a multispecific binding agent of the present invention.

Various delivery systems are known and can be used to administer a multispecific binding agent of the present invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, multispecific binding agent of the present invention are administered intravenously. In some embodiments, multispecific binding agents of the present invention are administered subcutaneously. In some embodiments, multispecific binding agents are administered together with other biologically active agents.

Pharmaceutical Compositions

The present invention further provides pharmaceutical compositions comprising multispecific binding agents of the present invention and a pharmaceutically acceptable carrier or excipient. The composition, if desired, can also contain one or more additional therapeutically active substances.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference).

Kits

The present invention further provides a pharmaceutical pack or kit comprising one or more containers filled with at least one multispecific binding agent as described herein. Kits may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXAMPLES

The invention will be further illustrated by the following non-limiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight,

Example 1. Design and Construction of Bispecific Fusion Proteins with a Dimerization Component The present Example describes production of a multispecific binding agent that is specifically engineered to be capable of dimerization as a strategy to enhance its tumor killing potency. This strategy was tested on a bispecific binding protein that can mediate T cell killing of GD2 positive tumor cells. Disialoganglioside GD2 is highly expressed on tumors of both pediatric and adult cancers, including neuroblastoma, retinoblastoma, melanoma, brain tumors, sarcomas and small cell lung cancer (Modak et al., 2007, Cancer Invest. 25:67-77). The present Example specifically illustrates construction of a dimerization-capable fusion protein, termed GD2×CD3-HDD, that is comprised of scFv polypeptides from anti-GD2 and anti-GD3 antibodies, linked to one another by an HNF-1α dimerization component, and that targets GD2 and CD3. Although HNF-1α was known to dimerize itself, it was not clear whether the dimerization component of HNF-1α could be employed to dimerize other proteins to which it could be attached, in particular, antibodies or components thereof. For example, the inventors have determined when attached to antibody components, human peptide hormone endotelin-1 (ET1), which is known to dimerize on its own, was unable to dimerize.

Additional Examples presented herein demonstrate the successful dimerization of this fusion protein, as assayed by dynamic light scattering, increased the functional affinity to GD2, enhanced T cell mediated killing of tumor cells in vitro, and inhibition of tumor growth in mice implanted with tumors. These Examples demonstrate the potential of the present strategy to increase the potency of T cell-engaging antibodies for cancer immunotherapy.

Molecular Cloning

Anti-GD2×anti-CD3 tandem scFv (GD2×CD3) bispecific binding proteins were constructed from single polypeptide chains containing the scFv of anti-GD2 monoclonal antibody 5F11 (Hu et al., 2009, J. Immunol. 183:5748-5755; Cheung et al., 2004, J. Nucl. Med. 45:867-877) and the humanized scFv of anti-CD3 OKT3 (Woodle et al., 1992, J. Immunol. 148:2756-2763) without and with a HNF-1α dimerization component (termed GD2×CD3 and GD2×CD3-HDD). The HDD component was placed distal to the anti-GD2 scFv, and proximal to the anti-CD3 ScFv. Without wishing to be bound by any particular theory, this placement was selected to maximize the potential enhancement of functional affinity to the distal antigen (GD2) and not the proximal antigen (CD3), which would be geometrically restricted. Enhancement of GD2 binding would presumably enhance tumor killing, whereas enhancement of CD3 binding could lead to enhanced cytokine storm, a known side effect of T cell engaging bispecific antibodies (Choi et al., 2011, Expert Opin. Biol. Ther. 11:843-853). Additionally, dimerization of tandem scFv bispecific binding proteins (MW ~55-60 kDa) have the potential to enhance the serum half-life since the homodimeric tandem scFv bispecific binding proteins could escape renal clearance pathway, to which proteins less than 60 kDa are subject Briefly, variable regions of the anti-GD2 antibody 5F11 and the humanized anti-CD3 OKT3 (derived from mouse OKT3 antibody) antibodies have been previously described. Single chain variable fragments (scFvs) of the 5F11 and humanized OKT3 (hOKT3) antibodies were genetically assembled in different orientations using a 15 amino acid linker $((G_4S)_3)$ and synthesized separately (Genescript, Piscataway, N.J.). $V_H V_L$ or $V_L V_H$ orientations were constructed using the variable regions of the 5F11 antibody and a $V_H V_L$ orientation was constructed using the variable regions of the anti-CD3 hOKT3 antibody. The specific identity of antibody components utilized in the present invention is not critical to the provided insight that adding a dimerization component improves activity of a multispecific binding agent comprised of antibody components targeting two antigens.

Single chain variable fragments constructed from the 5F11 antibody were digested with NheI and ApaI and the scFv constructed from the hOKT3 antibody was digested with ApaI and BamHI. The digested fragments were sequentially ligated into a Glutathione synthesis (GS) vector (Invitrogen) to make the bispecific binding proteins 5HLBT and 5LHBT.

Stabilizing mutations were made to two cysteine residues of the 5F11 scFv (heavy chain S44C, light chain A100C) by mutagenesis according to manufacturer's specifications (Stratagene, Calif.) to yield 5HLDSBT and 5LHDSBT. A linker sequence of either 15 $((G_4S)_3)$ or five $(G_4S)$ amino acids in length was cloned between the 5F11 scFv and hOKT3 scFv as well as 5HLDSBT and 5LHDSBT for comparison. In a similar fashion, stabilizing cysteine mutations were also introduced into the OKT3 scFv to yield 5HLDS-DSBT. Additionally, two affinity maturation mutations (P104Y and E31Q; Hu et al., 2009, J Immunol 183: 5748-5755) were separately introduced into 5HLDSBT to yield Y-BT and Q-BT, respectively.

Using the methods described above, other anti-GD2×anti-CD3 tandem scFv (GD2×CD3) bispecific binding proteins were constructed based on the humanized anti-GD2 antibody 3F8 (Cheung et al, 2012, OncoImmunol. 1:4, 477-486) and the humanized anti-CD3 OKT3 (Woodle et al., supra) with a HNF-1α dimerization component; and anti-GD3×anti-CD3 tandem scFv (GD3×CD3) bispecific binding proteins based on the monoclonal anti-GD3 antibody KM641 (Ohta et al., 1993, Cancer Immunol. Immunother. 36(4): 260-266) and the humanized anti-CD3 OKT3 (Woodle et al., supra) with a HNF-1α dimerization component. The dimerization component was fused to the C-terminus of the anti-CD3 antibody component using a portion of human IgG3 hinge (TPLGDTTHTSG). Exemplary fusion proteins as described above are shown in Table 5.

TABLE 5

| Name | Description |
| --- | --- |
| 5HLBT | $VHVL_{5F11}$-$(G_4S)_3$-$VHVL_{hOKT3}$ |
| 5LHBT | $VLVH_{5F11}$-$(G_4S)_3$-$VHVL_{hOKT3}$ |
| 5HLDS$_{15}$BT | $VHVL_{5F11(S44C, A100C)}$-$(G_4S)_3$-$VHVL_{hOKT3}$ |
| 5LHDS$_{15}$BT | $VLVH_{5F11(S44C, A100C)}$-$(G_4S)_3$-$VHVL_{hOKT3}$ |
| 5HLDS$_5$BT | $VHVL_{5F11(S44C, A100C)}$-$G_4S$-$VHVL_{hOKT3}$ |
| 5LHDS$_5$BT | $VLVH_{5F11(S44C, A100C)}$-$G_4S$-$VHVL_{hOKT3}$ |

TABLE 5-continued

| Name | Description |
| --- | --- |
| Y-BT | VHVL$_{5F11(S44C, A100C, P104Y)}$-G$_4$S-VHVL$_{hOKT3}$ |
| Q-BT | VHVL$_{5F11(E31Q)}$-G$_4$S-VHVL$_{hOKT3}$ |
| 3LHBT$_{v1}$-HDD | VLVH$_{hu3F8v1}$-(G$_4$S)$_3$-VHVL$_{hOKT3}$-HDD |
| 3LHBT$_{v1(D32H)}$-HDD | VLVH$_{hu3F8v1(D32H)}$-(G$_4$S)$_3$-VHVL$_{hOKT3}$-HDD |
| 3LHBT$_{v1(E1K, D32H)}$-HDD | VLVH$_{hu3F8v1(E1K, D32H)}$-(G$_4$S)$_3$-VHVL$_{hOKT3}$-HDD |
| 3LHBT$_{v1(E1K, D32H, G54I)}$-HDD | VLVH$_{hu3F8v1(E1K, D32H, G54I)}$-(G$_4$S)$_3$-VHVL$_{hOKT3}$-HDD |
| 3LHBT$_{v1(D32H, G54I)}$-HDD | VLVH$_{hu3F8v1(D32H, G54I)}$-(G$_4$S)$_3$-VHVL$_{hOKT3}$-HDD |
| 3LHBT$_{v1(E1K, G54I)}$-HDD | VLVH$_{hu3F8v1(E1K, G54I)}$-(G$_4$S)$_3$-VHVL$_{hOKT3}$-HDD |
| 3LHBT$_{v5}$-HDD | VLVH$_{hu3F8v5}$-(G$_4$S)$_3$-VHVL$_{hOKT3}$-HDD |
| 3LHBT$_{v5(D32H)}$-HDD | VLVH$_{hu3F8v5(D32H)}$-(G$_4$S)$_3$-VHVL$_{hOKT3}$-HDD |
| 3LHBT$_{v5(E1K, D32H)}$-HDD | VLVH$_{hu3F8v5(E1K, D32H)}$-(G$_4$S)$_3$-VHVL$_{hOKT3}$-HDD |
| 3LHBT$_{v5(E1K, D32H, G54I)}$-HDD | VLVH$_{hu3F8v5(E1K, D32H, G54I)}$-(G$_4$S)$_3$-VHVL$_{hOKT3}$-HDD |
| 3LHBT$_{v5(D32H, G54I)}$-HDD | VLVH$_{hu3F8v5(D32H, G54I)}$-(G$_4$S)$_3$-VHVL$_{hOKT3}$-HDD |
| 3LHBT$_{v5(E1K, G54I)}$-HDD | VLVH$_{hu3F8v5(E1K, G54I)}$-(G$_4$S)$_3$-VHVL$_{hOKT3}$-HDD |
| 641HLBT-HDD | VHVL$_{KM641}$-(G$_4$S)$_3$-VHVL$_{hOKT3}$-HDD |

Production and Purification

Expression constructs were made using the DNA of scFv$_{5F11}$-(G$_4$S)$_3$-scFv$_{hOKT3}$ fusion protein (Y-BT, SEQ ID NO:10) both with (GD2×CD3-HDD) and without (GD2×CD3) a dimerization component containing an element (amino acids 1-32) of HNF-1α followed by a 6× histidine tag. DNA was transfected into DG44 CHO-S cells (Invitrogen) by electroporation using a nucleofector II electroporation machine (Amaxa) and nucleofection solution V. Transfected cells were subjected to drug selection with 500 µg/ml G418. After about two weeks, single cells were plated to 96-well plates by serial dilution. Irradiated CHO-S cells were used as feeder cells at a concentration of 5000 cells/per well. Supernatant from each clone was harvested by three weeks and subjected to GD2 binding assay. Clones that demonstrated highest binding to GD2 were selected for scale up to a large culture with orbital shaking at 125 rpm at 37° C. and 8% CO$_2$ when cells reach 2 million/mL and are in log phase growth. Culture supernatants were harvested when a desired antibody yield was reached or when viability dropped to <40%. Bispecific fusion proteins (GD2×CD3 and GD2×CD3-HDD) secreted into the culture supernatant were purified by Ni2+ sepharose (GE Healthcare Bio-Sciences, Sweden) and eluted with 300 mM imidazole.

Example 2. In Vitro Screening and Affinity of Bispecific Fusion Proteins

This Example illustrates the effect of dimerization of single chain bispecific fusion proteins made in accordance with Example 1 on the functional affinity to their targets. In some cases, bispecific monomers may bind to their targets for short periods of time (e.g., poor retention due to size). In this example, bispecific fusion proteins that are engineered to form homodimers demonstrate increased affinity for an antigen.

Dynamic Light Scattering

The ability of the dimerization component of HNF-1α to induce dimerization in bispecific fusion proteins was tested by dynamic light scattering. Purified bispecific fusion proteins were measured for hydrodynamic radius using dynamic light scattering on a Zetasizer Nano (Malvern Instruments, Ltd.). Table 6 sets forth exemplary measurements using bispecific fusion proteins described in Example 1. Additional samples of purified bispecific fusion proteins were also measured for hydrodynamic radius using dynamic light scattering as described above. The results are shown in Table 7.

As shown in Tables 6 and 7, GD2×CD3 (MW 55 kDa) had a hydrodymanic radius of 7.2±1.7 nm, whereas GD2×CD3-HDD (MW 59 kDa for monomer, 118 kDa for dimer) had a hydrodymanic radius of 13.6±0.7 nm (or 11.1±0.5). The increase in size as demonstrated by light scattering is indicative of a dimeric conformation for GD2×CD3-HDD.

TABLE 6

| Fusion Protein | Diameter (nm) |
| --- | --- |
| GD2xCD3 | 7.2 ± 1.7 |
| GD2xCD3-HDD | 13.6 ± 0.7 |

TABLE 7

| Fusion Protein | Diameter (nm) |
| --- | --- |
| GD2xCD3 | 7.2 ± 1.7 |
| GD2xCD3-HDD | 11.1 ± 0.5 |

ELISA Assays

Figure 2A:
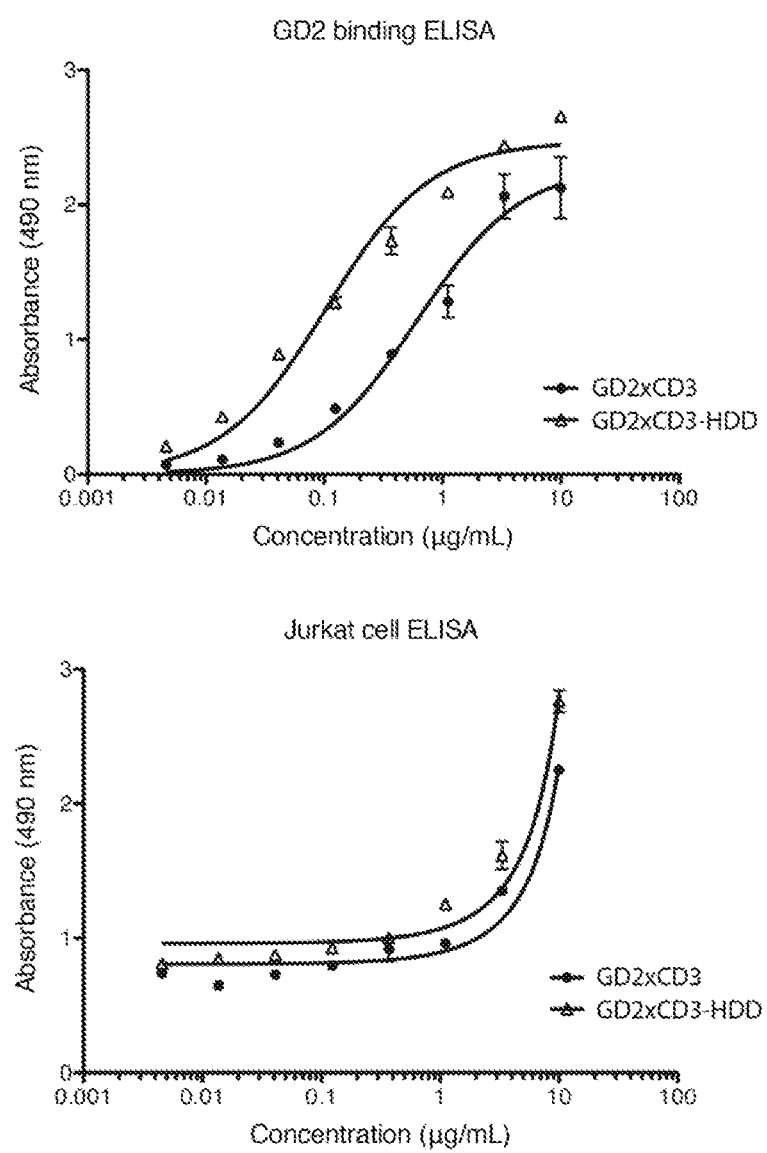
FIG. 2A shows ELISA binding curves of GD2 binding (top) and CD3 binding on Jurkat cells (bottom) for GD2×CD3 and GD2×CD3-HDD bispecific binding agents.
Figure 2B:
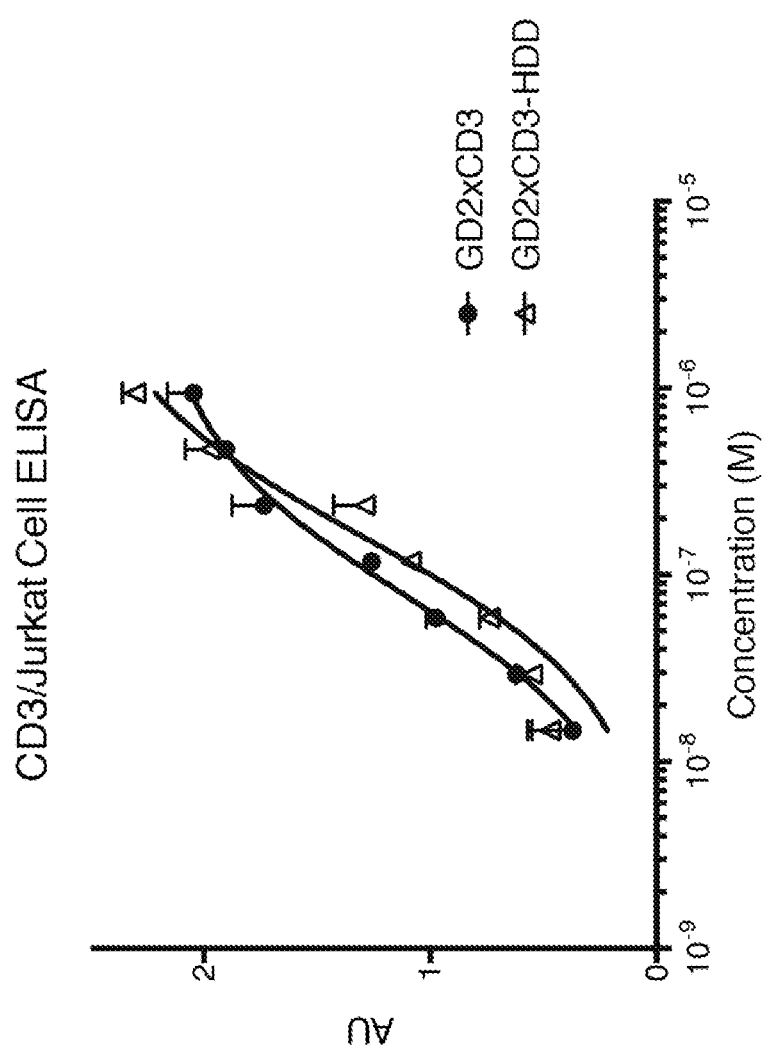
FIG. 2B shows CD3 binding on Jurkat cells for GD2×CD3 and GD2×CD3-HDD bispecific binding agents.

To determine if the HDD enhances the functional affinity to GD2 or CD3, ELISA assays were performed using purified GD2 and whole Jurkat cells (cultured T cells containing CD3). Briefly, 96-well plates were coated overnight with GD2 at 1 µg/mL per well in 90% ethanol at room temperature. The following day, plates were blocked with 150 µl/well of 0.5% BSA at room temperature for one hour. After washing, a dilution series of the bispecific antibodies were added to the plates and incubated at room temperature for two hours. The plate was subsequently washed four times with PBS and then incubated at room temperature for our hour with 100 µl/well of a mouse-anti-His-tag antibody (AbD Serotec) at 1:1000 dilution in 0.5% BSA. The plate was washed again four times with PBS and then incubated at room temperature for one hour with 100 µl/well of a goat-anti-mouse-HRP antibody (Jackson ImmunoResearch) at 1:3000 dilution in 0.5% BSA. The plate was washed again four times with PBS and developed using 150 µl/well of OPD buffer (Sigma). The reaction was stopped with 30 µl/well of 5N H$_2$SO$_4$. The plates were then read at 490 nm on a spectrophotometer. Table 8 and FIG. 2A (top panel) set forth exemplary GD2 binding of bispecific fusion proteins made according to Example 1. FIG. 2A (bottom) sets forth CD3/Jurkat cell binding of bispecific fusion proteins made according to Example 1. Additional samples of purified bispecific fusion proteins were also measured for CD3/Jurkat cell binding. The results are shown in FIG. 2B.

In vitro binding kinetics were determined using a Biacore T-100 Biosensor (GE Healthcare). A CM5 sensor chip and related reagents were purchased from Biacore USA. Gangliosides GM1 was purchased from ALEXIS Biochemicals (AXXORA L.L.C.), and GD2 from Advanced Immuno-Chemical. Briefly, gangliosides were directly immobilized onto the CM5 sensor chip via hydrophobic interaction. Reference surface was immobilized with GM1. Active surface was immobilized with GD2 and GM1 in 1:1 ratio. A diluted mixture of GD2 and GM1 (50 µg/ml) was injected (300 µl) at a flow rate of 15 µl/min over 20 minutes. Extensive washing was followed with 10 mM NaOH (typically five washes of 20 µl at a flow rate of 5 µl/min) until a stable baseline was obtained.

Figure 3A:
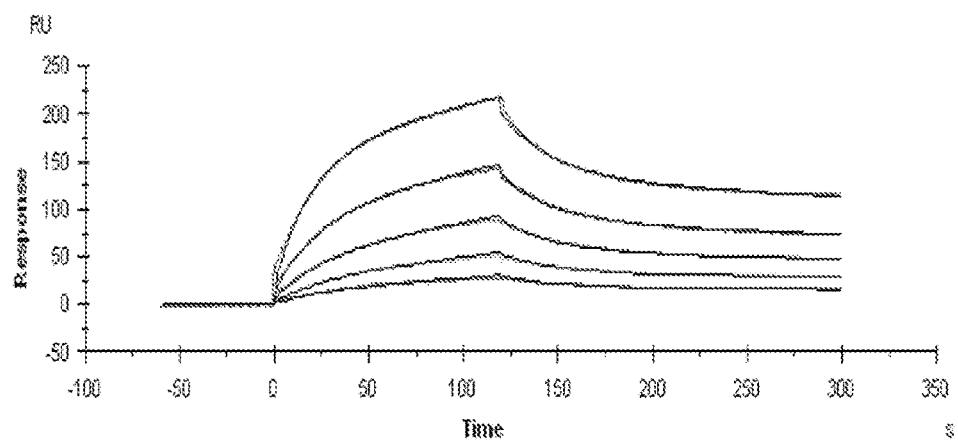
FIGS. 3A and 3B shows Biacore sensorgrams of GD2 binding for GD2×CD3 and GD2×CD3-HDD bispecific binding agents. Traces are shown at the following bispecific antibody concentrations: 62.5, 125, 250, 500, 1000, 2000 nM.
Figure 3A:
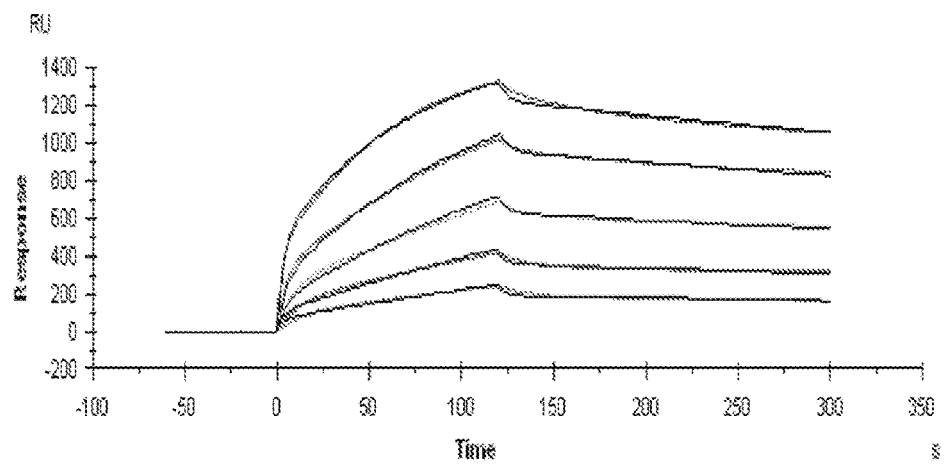
Figure 3B:
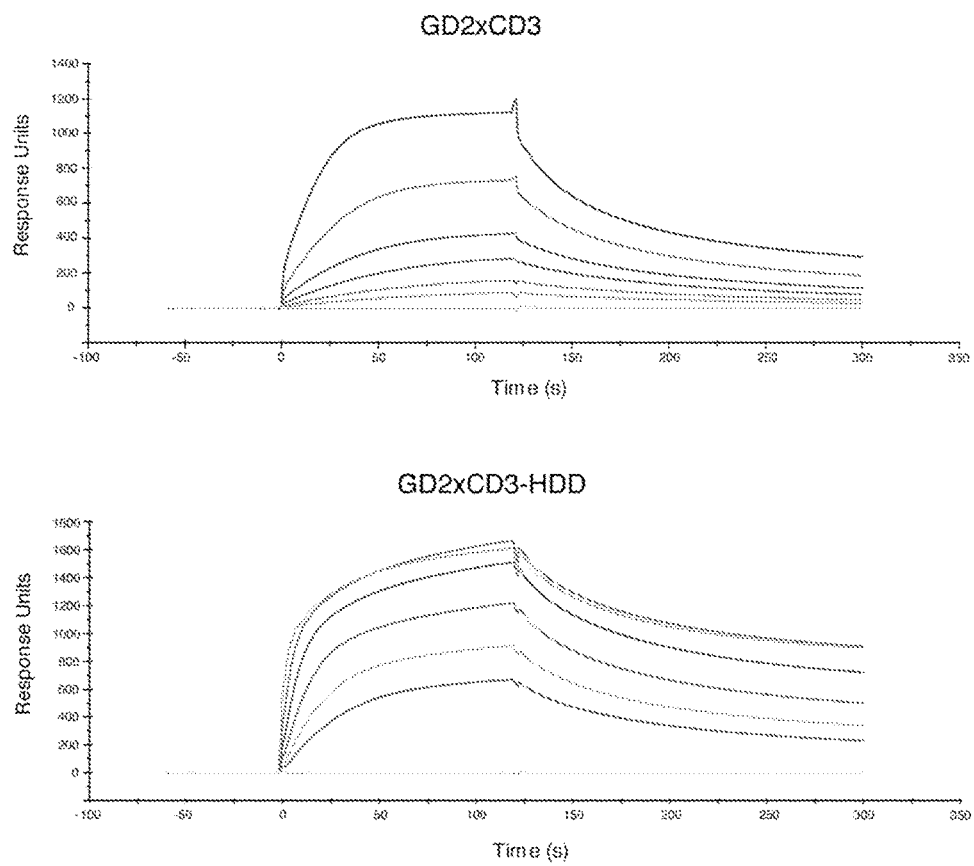

Purified anti-GD2 monoclonal antibody (5F11) was diluted in HBS-E buffer containing 250 mM NaCl at varying concentrations (50~1600 nM) prior to analysis. Samples (60 µl) were injected over the sensor surface at a flow rate of 30 µl/min over 2 minutes. Following completion of the association phase, dissociation was monitored in HBS-E buffer containing 250 mM NaCl for 300 seconds at the same flow rate. At the end of each cycle, the surface was regenerated using 50 µl 20 mM NaOH at a flow rate of 50 µl/min over one minute and 100 µl 4M $MgCl_2$ at a flow rate of 50 µl/min over two minutes. The biosensor curves obtained following injection of the samples over immobilized GD2 were subtracted with the control curves obtained with the samples injected over immobilized GM1 prior to kinetics analysis. The data were analyzed by the bivalent analyte model and default parameter setting for the rate constants using Biacore T-100 evaluation software. Association on rate constant ($k_{on}$), dissociation off rate constant ($k_{off}$) and equilibrium dissociation constant ($K_D = k_{off}/k_{on}$) were calculated. Table 9 and FIG. 3A set forth exemplary $K_D$ values sensorgrams for bispecific fusion proteins made according to Example 1. Additional samples of purified bispecific fusion proteins were also tested by Biacore. Exemplary results are shown in Table 10 and FIG. 3B.

TABLE 8

| Fusion protein | GD2 ELISA $EC_{50}$ (µg/mL) |
|---|---|
| GD2xCD3 | 0.61 ± 0.11 |
| GD2xCD3-HDD | 0.10 ± 0.02 |

TABLE 9

| Fusion protein | Biacore $K_D$ (nM) |
|---|---|
| GD2xCD3 | 105 |
| GD2xCD3-HDD | 35 |

TABLE 10

| Fusion protein | $K_{on}$ (1/Ms) | $K_{off}$ (1/s) | $K_D$ (nM) |
|---|---|---|---|
| GD2xCD3 | $9.07 \times 10^4$ | $2.27 \times 10^{-2}$ | 250 |
| GD2xCD3-HDD | $8.83 \times 10^4$ | $3.45 \times 10^{-3}$ | 39 |

As shown in Table 8, ELISA binding assays showed a 6-fold enhancement of GD2 binding for GD2xCD3-HDD relative to GD2xCD3 bispecific binding proteins (also see top panel of FIGS. 2A and 2B). Binding to Jurkat cells was not significantly different (see bottom panel of FIGS. 2A and 2B). Biacore analysis of GD2 binding (FIGS. 3A and 3B; and Tables 9 and 10) confirms the affinity enhancement to the tumor target GD2 by 3- to 6-fold.

Figure 7:
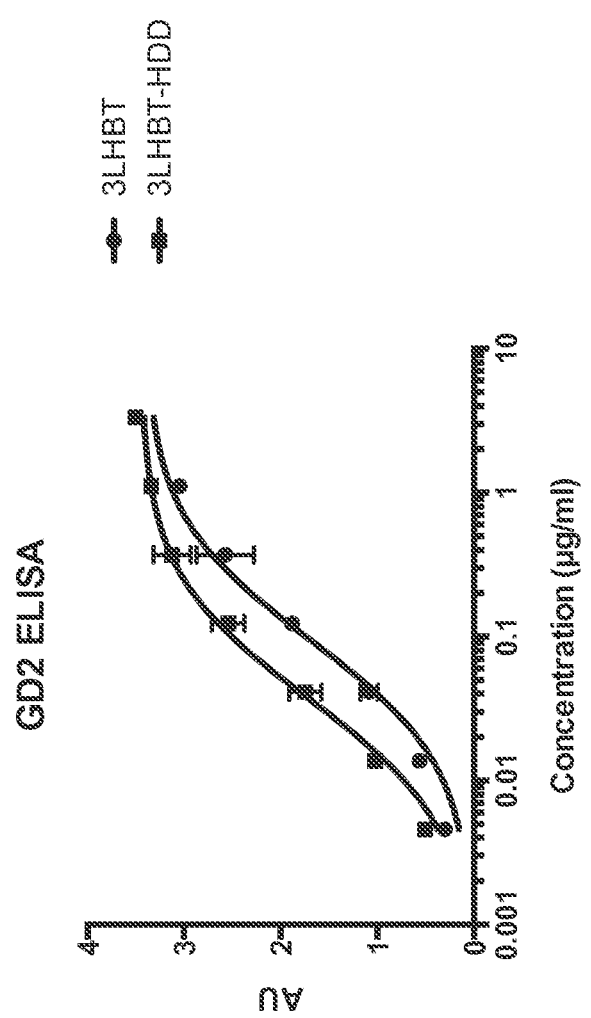
FIG. 7 shows ELISA binding curves of GD2 binding for 3LHBT and 3LHBT-HDD bispecific binding agents.

In a similar experiment, 3LHBT-HDD (SEQ ID NO:11) was tested for GD2 binding as described above. The results are shown in Table 11 and FIG. 7. The results confirm that, as described herein, 3LHBT-HDD shows better activity based on GD2 binding. Specifically, 3LHBT-HDD demonstrated an about 2.5-fold lower $EC_{50}$ than 3LHBT.

TABLE 11

| Fusion protein | ELISA $EC_{50}$ (µg/mL) |
|---|---|
| 3LHBT | 0.096 ± 0.011 |
| 3LHBT-HDD | 0.038 ± 0.003 |

Taken together, these data demonstrate that the dimerization component of human HNF-1α effectively induces dimerization of a single chain bispecific antibody to form a homodimer which and enhances the functional affinity to one of the antigens of the bispecific antibody (e.g. a tumor antigen).

Example 3. In Vitro T Cell Mediated Cell Killing of Tumor Cells

This Example demonstrates the enhanced ability of bispecific homodimers to initiate tumor cell killing mediated through T cells. Typically, bispecific binding proteins that engage T cells are able to direct T cell to a tumor site for T cell mediated killing of the tumor. In this example, exemplary bispecific homodimers are shown to effectively mediate T cell killing of tumor cells more effectively as compared to bispecific single chain proteins.

Chromium 51 ($^{51}Cr$) Release Assay

Melanoma and neuroblastoma cells (SKMEL1, NMB-7, M14, BE (1)N, HTB63, H524, SKNJC2, SKMEL28, H69, H196 and H345) were cultured in RPMI1640 (Cellgro) supplemented with 10% FBS (Life Technologies) at 37° C. in a 5% $CO_2$ humidified incubator. Neuroblastoma cell line LAN1 and melanoma M14 were obtained from University of California, Los Angeles. SKNLD was developed at Memorial Sloan Kettering Cancer Center. SKLND cell line was derived from ATCC IMR-32. Verification was performed by short tandem repeat (STR) DNA sequencing.

Adherent cells were harvested with 1×EDTA. T cells were purified from human PBMC using a Pan T cell isolation kit according to manufacturer's specifications (Miltenyi Biotec). CD3/CD28 dynabeads (Invitrogen) were used to stimulate and expand T cells according to manufacturer's specifications. Expanded T cells were cultured and maintained in RPMI supplemented with FBS and 30 U/mL interleukin-2 (IL-2). T cell populations were identified and analyzed with anti-CD3-percep cy5.5, anti-CD4-FITC, anti-CD8-APC and anti-CD56-PE antibodies (BD Biosciences) by flow cytometry using a FACSARIA™.

Target tumor cells were labeled with sodium $^{51}Cr$ chromate (Amersham, Arlington Height, Ill.) at 100 µCi/$10^6$ cells at 37° C. for one hour. Cells were washed twice. Target cells (5000 cells/well) were admixed with effecter cells and bispecific fusion proteins in 96-well polystyrene round-bottom plates (BD Biosciences) to a final volume of 250 µl/well. The plates were incubated at 37° C. for four hours and then centrifuged at 400 g for five minutes. $^{51}Cr$ release into the supernatant was counted in a gama counter (Packed Instrument, Downers Grove, Ill.). Percentage of specific release was calculated using the formula 100% (experimental cpm−background cpm)/(5% sodium dodecyl sulfate [SDS] cpm−background CPM), where cpm are counts per minute of $^{51}$Cr released. Total release was assessed by lysis with 5% SDS (Sigma, St Louis, Mo.), and background release was measured in the absence of effector cells. Exemplary results of T cell mediated tumor cell killing for bispecific fusion proteins made in accordance with Example 1 are set forth in Table 12 and FIG. 4.

TABLE 12

| Target cells | EC$_{50}$ (ng/mL) GD2xCD3 | EC$_{50}$ (ng/mL) GD2xCD3-HDD | Fold difference | Significance |
|---|---|---|---|---|
| M14 | 17.35 | 0.64 | 27x | p < 0.001 |
| LAN1 | 5.68 | 0.47 | 12x | p < 0.001 |
| SKNLD | 38.8 | 3.14 | 12x | p < 0.001 |

Figure 4:
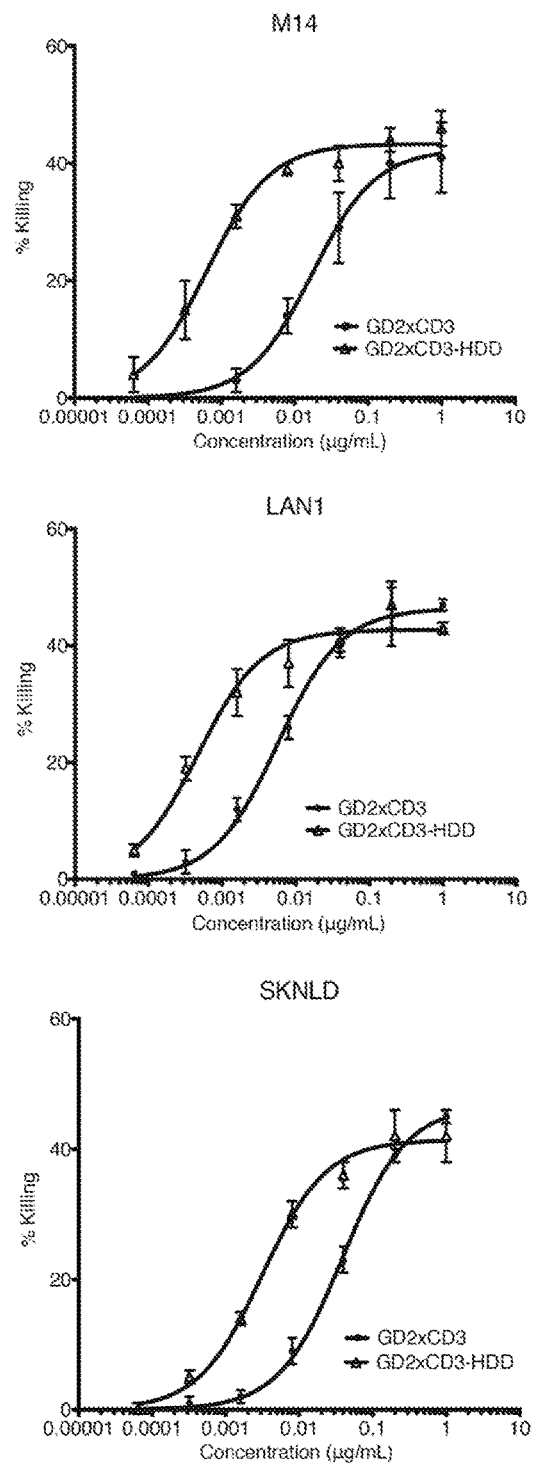
FIG. 4 shows the percentage of T-cell mediated killing of melanoma and neuroblastoma cell lines in vitro for GD2×CD3 and GD2×CD3-HDD bispecific binding agents.

As shown in Table 12 and FIG. 4, GD2xCD3 and GD2xCD3-HDD bispecific fusion proteins were able to mediated T cell killing of selected GD2-positive tumor cell lines. In particular, GD2xCD3-HDD showed a significant enhancement in the ability to direct T cell mediated killing of tumor cells versus GD2xCD3 (12-27 fold increase, p<0.001).

The present Examples just demonstrate, among other things, that dimerization of bispecific fusion proteins that bind to a tumor antigen and CD3 can effectively enhance the ability of the bispecific fusion protein to mediate T cell killing of tumor cells that express the tumor antigen.

Example 4. In Vivo Efficacy of Bispecific Fusion Protein Homodimers

Multispecific fusion proteins described in the prior Examples were tested for their in vivo efficacy.

Xenograft Mouse Model

A breeder mouse strain BALB/cA-Rag2KO/IL-2RγKO (DKO) was kindly provided by Dr. Mamoru Ito (Central Institute for Experimental Animals [CIEA], Miyamae, Kawasaki, Japan) and propagated at Memorial Sloan-Kettering Cancer Center. Animals were provided with Sulfatrim food. Care of all animals complied with the Canadian Council on Animal Care guidelines. In vivo experiments were performed when mice reached 6-week to 12-weeks of age.

Peripheral blood mononuclear cells (PBMC) of healthy donors were isolated from discarded buffy coats from healthy donors (New York Blood Center, NY). PBMC were separated using Ficoll-paque (GE Healthcare Life Sciences) and washed in PBS. Erythrocytes were depleted by incubation for 30-60 seconds with ACK Lysing buffer (GIBCO, Life Technologies Corp).

Figure 5:
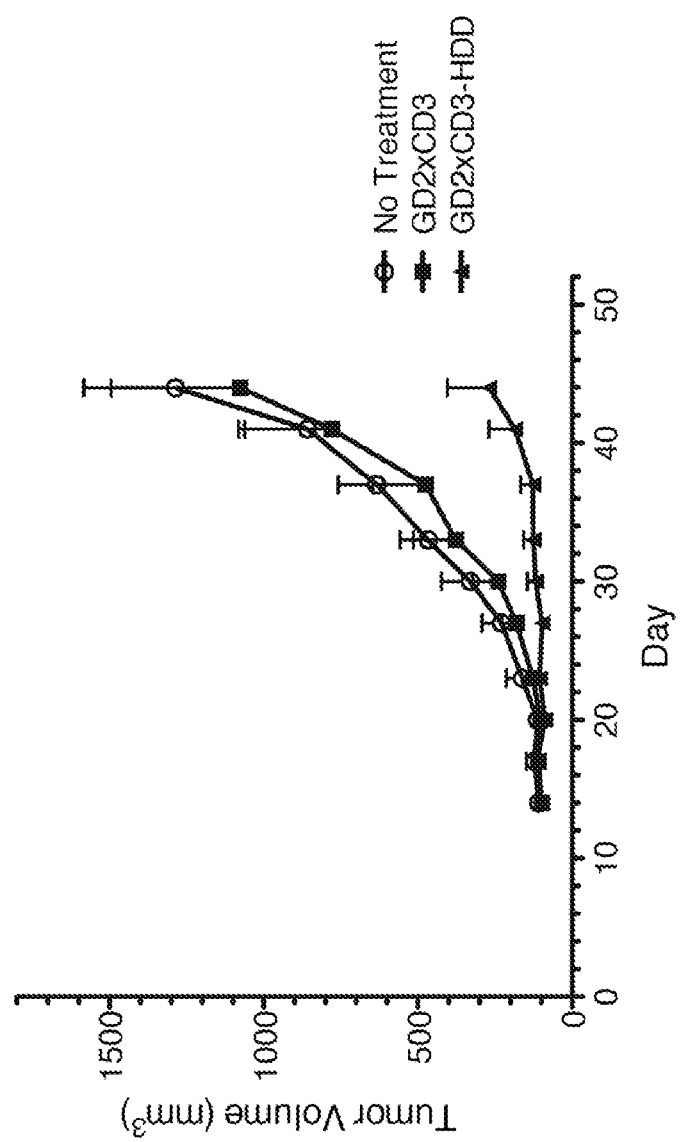
FIG. 5 shows the tumor volume (mm³) of subcutaneous SKNLD tumors implanted into BALB/cA-Rag2KO/IL-2RγKO (DKO) mice in control (no treatment), GD2×CD3, and GD2×CD3-HDD treated groups of a xenograft study model.

Purified PBMC were mixed with SKNLD cells (a fast-growing subcutaneous neuroblastoma) in a 1:1 ratio (50,000 PBMC:50,000 SKNLD cells) in Matrigel (BD Biosciences). DKO mice were implanted with the PMBC/SKNLD mixed cells. At 4 days post-implantation, five mice per group were given no treatment, intravenous injections of GD2xCD3 (five times per week for two weeks), or intravenous injections of GD2xCD3-HDD (five times per week for two weeks). Tumor size was measured by calipers twice per week from day 14 to day 44. Blood was obtained from tail vein of DKO mice over eight hours after a bolus injection of 50 μg of bispecific fusion protein. Serum levels of bispecific fusion protein were measured by double sandwich ELISA where bispecific fusion protein was captured using solid phase rat anti-5F11-idiotypic antibody, and bound bispecific fusion protein detected using biotinylated mouse-anti-His-tag antibody (AbD Serotec) followed by strepavidin-HRP (Life Technologies, Invitrogen). Exemplary measurements of tumor volume for each group is shown in FIG. 5. The area under the curve was calculated for each mouse, and the averages are shown in Table 15.

Exemplary pharmacokinetic analysis of GD2xCD3 and GD2xCD3-HDD is shown in Table 16. Additional samples of purified bispecific fusion proteins were tested for pharmacokinetic analysis (Table 17).

TABLE 15

| | No treatment | GD2xCD3 | GD2xCD3-HDD |
|---|---|---|---|
| AUC (mm$^3$ × days) | 12,346 ± 5969 | 10,165 ± 6434 | 3850 ± 1967 |
| Significance | — | p = 0.59 | p = 0.02 |

TABLE 16

| Fusion protein | Half-life (h) |
|---|---|
| GD2xCD3 | 0.78 ± 0.69 |
| GD2xCD3-HDD | 2.56 ± 0.54 |

TABLE 17

| Fusion protein | Half-life (min) |
|---|---|
| GD2xCD3 | 14.04 ± 10.42 |
| GD2xCD3-HDD | 54.68 ± 17.62 |
| Fold difference | 3.9 |
| p-value | 0.002 |

As shown in Table 15, GD2xCD3 showed a modest reduction in tumor growth (about 18% lower AUC), which was not statistically significant (p=0.59). However, GD2xCD3-HDD showed a significant reduction in tumor growth (about 69% lower AUC, p=0.02) and greater than GD2xCD3. Pharmacokinetic analysis showed a greater than 3-fold (or about 4-fold) increase in serum half-life of GD2xCD3-HDD relative to GD2xCD3 (p=0.002, see Tables 16 and 17).

Figure 6:
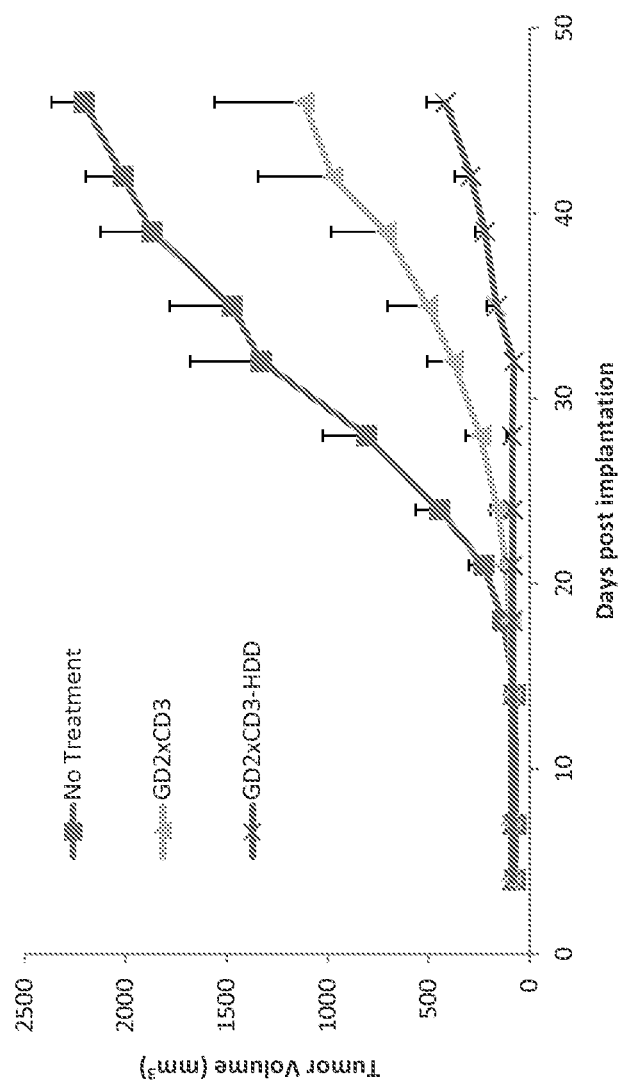
FIG. 6 shows the tumor volume (mm³) of subcutaneous M14 tumors implanted into BALB/cA-Rag2KO/IL-2RγKO (DKO) mice in control (no treatment), GD2×CD3, and GD2×CD3-HDD treated groups of a xenograft study model.

In a similar experiment, DKO mice were implanted with the PMBC/M14 mixed cells as described above. Exemplary measurements of tumor volume for each group is shown in FIG. 6.

Taken together, these data show that administration of dimeric multispecific binding proteins (in this case, homodimeric bispecific antibody proteins) that target a tumor antigen and T cells via CD3 effectively reduces tumor growth in vivo. In particular, such a reduction in tumor growth is greater as compared to the same bispecific binding protein in a single chain conformation. Further, homodimeric bispecific binding proteins demonstrate a longer half-life as compared to single chain conformations of the same bispecific binding protein.

Example 5. Cytokine Release Assay

Multispecific fusion proteins described in the prior Examples were tested to confirm that the dimerization tag (HDD, SEQ ID NO:1) would not enhance the release of cytokines resulting from increased binding to CD3.

Briefly, PBMC were isolated from the blood of healthy donors by lymphocyte separation medium centrifugation (Mediatech, Inc.). Human T cells were purified by Pan T cell isolation kit according to manufacturer specifications (Miltenyi Biotec). T cells (50,000/per well) were co-cultured with neuroblastoma SKNLD cells (10,000/per well) in 96 well plate with BsAb at 37° C. Supernatants were harvested after 24 hours. Concentration of four different cytokines (IL-2, IL-10, IFN-γ and TNF-α) was measured using an ELISA based cytokine assay kit (OptEIA™ human cytokine set, BD Biosciences) according to manufacturer specifications. Level of each cytokine was quantitated according to the standard supplied with the assay kit. Positive control samples were run using T-cells activated with CD3/CD8 immunobeads to confirm adequate cytokine detection. Table 18 sets forth exemplary cytokine release from human T cells in the presence of BsAb or parental humanized OKT3 antibody (units are in pg/mL). Table 19 sets forth exemplary cytokine release from human Tcells in the presence of BsAb and neuroblastoma SKNLD cells or parental humanized OKT3 antibody (units are in pg/mL).

TABLE 18

| Cytokine | GD2xCD3 | GD2xCD3-HDD BsAb | Humanized OKT3 IgG |
|---|---|---|---|
| TNF-α | 7.9 ± 0.04 | 7.6 ± 0.49 | 86.7 ± 0.01 |
| IFN-γ | 1.7 ± 0.00 | 2.1 ± 0.03 | 228.2 ± 10.1 |
| IL-10 | 3.6 ± 0.15 | 2.1 ± 0.06 | 29.8 ± 0.002 |
| IL-2 | 2.0 ± 0.00 | 2.2 ± 0.01 | 36.5 ± 1.18 |

TABLE 19

| Cytokine | GD2xCD3 | GD2xCD3-HDD BsAb | Humanized OKT3 IgG |
|---|---|---|---|
| TNF-α | 530 ± 7.4 | 462 ± 31 | 275.4 ± 1.0 |
| IFN-γ | 431 ± 7.3 | 590 ± 3.1 | 515.5 ± 0.7 |
| IL-10 | 24 ± 2.7 | 23 ± 0.83 | 30.5 ± 4.0 |
| IL-2 | 6.2 ± 0.03 | 9.5 ± 0.08 | 19.9 ± 0.9 |

As shown in Tables 18 and 19, no significant enhancement of cytokine release for GD2×CD3-HDD BsAb relative to GD2×CD3 in T cells with (p=0.7) or without (p=0.5) added tumor cells was observed. Taken together, these results confirm that, as described herein, the bispecific fusion proteins described in Example 1 maximize the enhancement of functional affinity to the distal antigen (GD2), and not the proximal antigen (CD3), thereby resulting in enhanced tumor killing without enhancement of cytokine release, which is a known side effect of T cell engaging bispecific antibodies.

Example 6. Characterization of Multispecific Fusion Proteins with Dimerization Components The present Example describes the further production of multispecific binding agents that are specifically engineered to be capable of dimerization by employing different dimerization components, for example, a synthetic helix-turn-helix domain ("dHLX", GELEELLKHLKELLKG-PRK-GELEELLKHLKELLK, SEQ ID NO:24; Pluckthun et al., 1997, Immunotechnology 3(2):83) and human IgG1 Fc. dHLX, like HDD, is composed of a helix-loop-helix domain that forms non-covalent dimers. In contrast, dHLX is synthetic and may be immunogenic if injected into humans.

GD2xCD3 bispecific binding agents were produced with either the HDD, dHLX domain or human IgG1 Fc at their respective C-termini (as described in Example 1) and tested for GD2 binding (as described in Example 2) and in vitro T cell mediated killing of melanoma M14 and neuroblastoma LAN-1 tumor cell lines (as described in Example 3). Table 20 and FIG. 8 sets forth exemplary GD2 binding of GD2× CD3 bispecific binding agents with different dimerization domains. Table 21 and FIG. 9 sets forth exemplary in vitro T-cell mediated killing of melanoma M14 and neuroblastoma LAN-1 tumor cell lines by GD2×CD3 bispecific binding agents with different dimerization domains.

TABLE 20

| Fusion protein | ELISA EC$_{50}$ (nM) |
|---|---|
| GD2xCD3 | 5.0 ± 1.4 |
| GD2xCD3-HDD | 0.6 ± 0.1 |
| GD2xCD3-Fc | 0.3 ± 0.1 |
| GD2xCD3-dHLX | 2.9 ± 0.6 |

TABLE 21

| | LAN-1 | | M14 | |
|---|---|---|---|---|
| Fusion protein | EC$_{50}$ (nM) | Max Killing (%) | EC$_{50}$ (nM) | Max Killing (%) |
| GD2xCD3 | 0.207 ± 0.026 | 55 ± 1 | 0.161 ± 0.013 | 59 ± 1 |
| GD2xCD3-HDD | 0.024 ± 0.003 | 56 ± 1 | 0.020 ± 0.002 | 64 ± 1 |
| GD2xCD3-Fc | 0.045 ± 0.004 | 48 ± 1 | 0.030 ± 0.005 | 50 ± 1 |
| GD2xCD3-dHLX | 0.316 ± 0.031 | 54 ± 1 | 0.248 ± 0.033 | 62 ± 2 |

Figure 8:
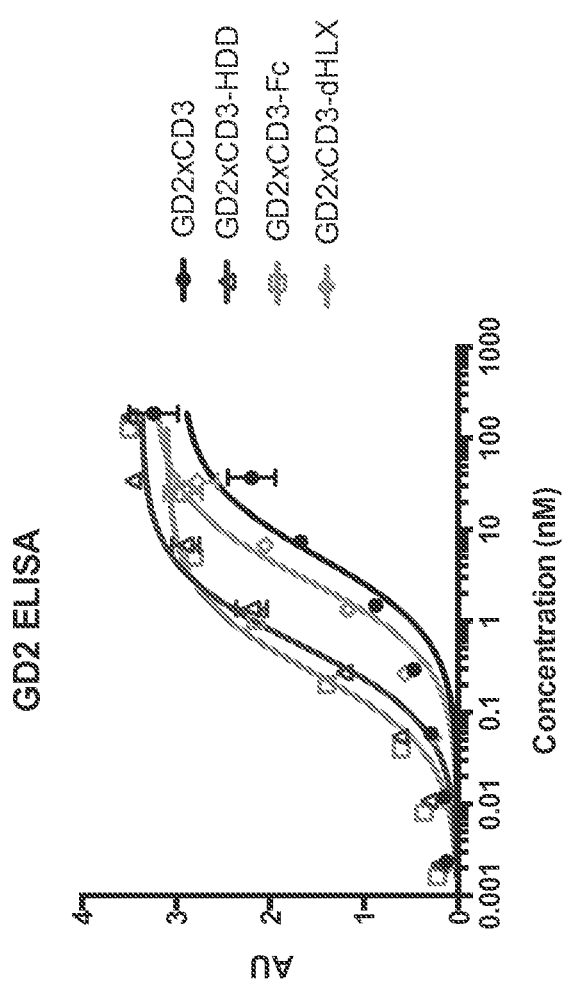
FIG. 8 shows ELISA binding curves of GD2 binding for GD2×CD3 bispecific binding agents with different dimerization domains.

As shown in Table 20 and FIG. 8, similar binding to GD2 was observed for GD2×CD3-HDD and GD2×CD3-Fc dimeric bispecific fusion proteins (0.6 nM versus 0.3 nM), which dimers result from non-covalent and covalent interactions, respectively. In contrast, the dimeric GD2×CD3-dHLX, as well as the monomeric GD2×CD3, demonstrated several fold lower binding avidity to GD2 (i.e., 2.9 nM and 5.0 nM, respectively). Further, unlike the other dimeric fusion proteins, GD2×CD3-dHLX demonstrated significant aggregation (data not shown).

Figure 9:
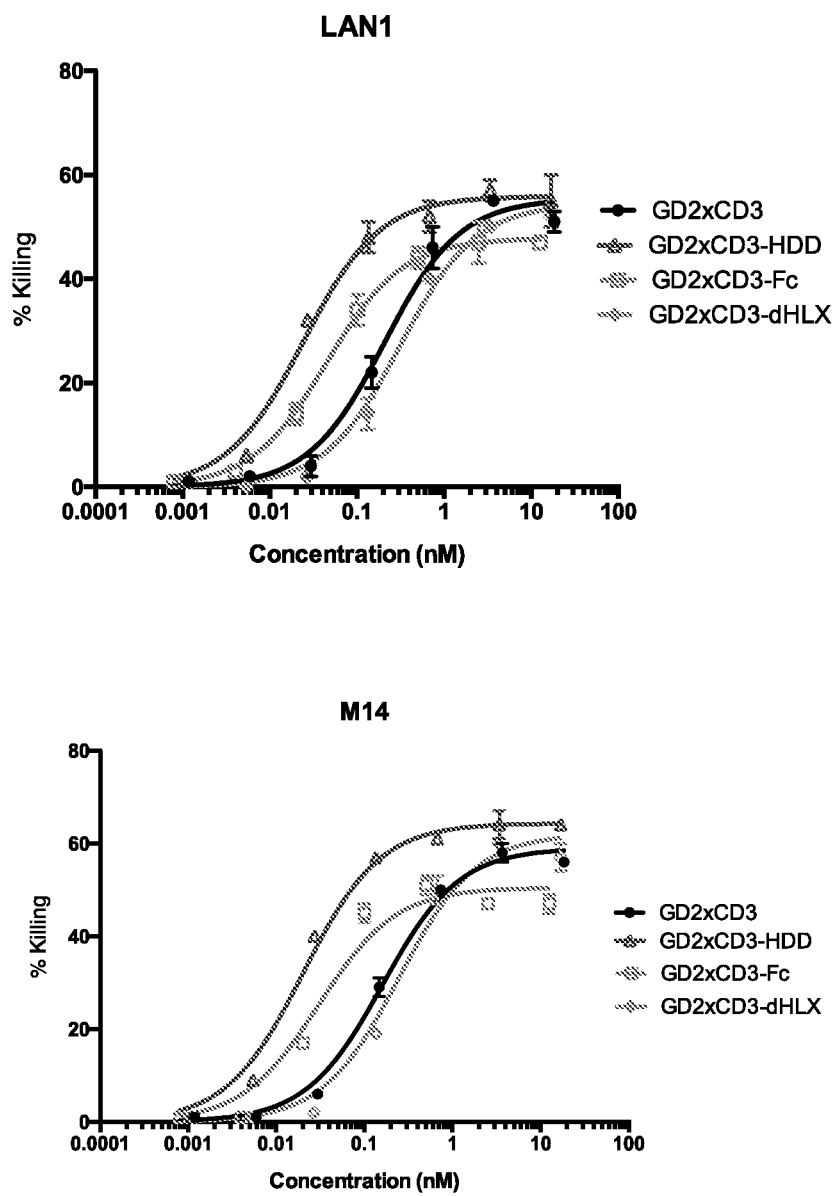
FIG. 9 shows the percentage of T-cell mediated killing of melanoma and neuroblastoma cell lines in vitro for GD2×CD3 bispecific binding agents with different dimerization domains.

As shown in Table 21 and FIG. 9, GD2×CD3-HDD demonstrated the most efficient in vitro T-cell mediated killing of melanoma M14 and neuroblastoma LAN-1 tumor cell lines. Moreover, despite having slightly higher GD2 avidity, GD2×CD3-Fc demonstrated lower in vitro tumor cell killing as measured by both EC$_{50}$ and maximum percent tumor killing than GD2×CD3-HDD. In contrast, GD2× CD3-dHLX demonstrated the lowest tumor cell killing, and noteably was lower than monomeric GD2×CD3.

Taken together, these further demonstrate that, as described herein, HDD can provide dimeric bispecific agents with enhanced tumor antigen binding avidity and similar to binding avidity achieved with covalent dimerization domains (e.g., a human IgG1 Fc). HDD provided improved T cell mediated killing as compared to that observed with other dimerization domains, confirming that the present invention provides uniquely useful dimerization component, particularly for use in T cell-engaging bispecific binding agents.

As shown in the preceding Examples, fusing a dimerization component from human HNF-1α to the carboxy-terminus of an GD2×CD3 tandem scFv promotes the formation of stable dimers and enhances the functional affinity of the distal anti-tumor antibody component of the bispecific dimer. Typically, tumors evade T cells by down regulating HLA and up regulating regulatory T cells, interfering with homing of cytolytic T cells (CTL) of generally low clonal frequency. Bispecific antibodies engaging CD3 on T cells can activate and redirect polyclonal T cells to tumors. Bispecific dimers of the present invention possess enhanced functional affinity for tumor cells expressing GD2 and lead to a significant enhancement of tumor cell killing in in vitro assays of GD2-positive tumor cell lines using activated T cells as effectors. The dimerization component of the present invention does not significantly enhance T cell binding or cytokine release, which is known to be an adverse side effect of T cell engaging bispecific antibody immunotherapy.

Moreover, the Examples demonstrate that the HDD tag is particularly useful when applied to antibody components as exemplified in the GD2×CD3 bispecific antibody (BsAb). The inventors have demonstrated a unique design for a BsAb (see FIG. 1) which can enhance avidity for a specific epitope of one binding arm of the BsAb (i.e., the distal anti-GD2 end and not the proximal anti-CD3 end). A major drawback in the development of T-cell engaging bispecific antibodies has been overstimulation of T cells resulting from CD3 engagement. Such engagement can lead to excessive release of cytokines (known as cytokine storm), which results in serious adverse effects in patients. As shown in the Examples, employing the HDD tag in a GD2×CD3 BsAb enhances binding to GD2 and not to CD3 (see FIG. 2), without causing any significant difference in cytokine release (see Tables 18 and 19 comparing monomeric GD2× CD3 and dimeric GD2×CD3-HDD). Both the GD2×CD3 and GD2×CD3-HDD antibodies demonstrated several fold less cytokine release than the bivalent anti-CD3 IgG huOKT3.

Taken together, bispecific dimer entities of the present invention have enhanced affinity and killing efficiency as compared with their non-dimerized counterparts, and, when coupled with the increased serum half-life, led to significant tumor reduction in mouse xenograft model of neuroblastoma.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A bispecific binding agent comprised of two fusion proteins, wherein each of the fusion proteins comprise from N-terminus to C-terminus:
   (i) a first antibody component that binds a tumor antigen;
   (ii) a second antibody component that binds an antigen present on an immune effector cell; and
   (iii) a dimerization component comprising a human hepatocyte nuclear factor-1 alpha (HNF-1α) element, wherein the HNF-1α element comprises a sequence that is at least 90% identical to residues 1-32 of SEQ ID NO:1, and
   wherein the fusion proteins can dimerize through the dimerization component to form a homodimer.

2. The binding agent of claim 1, wherein the tumor antigen is GD2.

3. The binding agent of claim 1, wherein the antigen present on an immune effector cell is CD3.

4. The binding agent of claim 1, wherein the dimerization component comprises amino acid residues 1-32 of SEQ ID NO:1.

5. The bispecific binding agent of claim 1, wherein the bispecific binding agent has enhanced tumor antigen binding avidity as compared to an otherwise comparable bispecific binding agent that does not comprise the dimerization component.

6. The bispecific binding agent of claim 5, wherein the bispecific binding agent does not have significantly different binding avidity to an immune effector cell as compared to an otherwise comparable bispecific binding agent that does not comprise the dimerization component.

7. A pharmaceutical composition comprising a bispecific binding agent of claim 1 and a pharmaceutically acceptable carrier.

8. A fusion protein comprising, from N-terminus to C-terminus, a first antibody component that binds to a tumor antigen, a second antibody component that binds to an antigen present on T cells, and a dimerization component comprising a human hepatocyte nuclear factor-1 alpha (HNF-1α) element, wherein the HNF-1α element comprises a sequence that is at least 90% identical to residues 1-32 of SEQ ID NO:1.

9. The fusion protein of claim 8, wherein the HNF-1α element comprises amino acid residues 1-32 of SEQ ID NO:1.

10. The fusion protein of claim 8, wherein the first and second antibody components are scFvs.

11. The fusion protein of claim 8, wherein the tumor antigen is GD2.

12. The fusion protein of claim 9, wherein the antigen present on T cells is CD3.

13. A dimeric bispecific binding agent comprised of two fusion proteins of claim 12.

14. A pharmaceutical composition comprising the dimeric bispecific binding agent of claim 13 and a pharmaceutically acceptable carrier.

15. The fusion protein of claim 8, wherein the fusion protein comprises a sequence that is at least 90% identical to any one of SEQ ID NO: 2-23.

16. The fusion protein of claim 8, wherein the fusion protein comprises a sequence that is selected from any one of SEQ ID NO: 2-23.

17. A nucleic acid sequence encoding a fusion protein of claim 8.

18. A vector comprising the nucleic acid sequence of claim 17.

19. An isolated host cell comprising the vector of claim 18.

20. The isolated host cell of claim 19, wherein the cell is selected from the group consisting of a bacterial, yeast, insect, or mammalian cell.

21. The host cell of claim 20, wherein the host cell is selected from the group consisting of *E. coli, Pichia pastoris*, Sf9, COS, HEK293 and a CHO cell.

22. A method of producing a dimeric bispecific binding agent, comprising culturing the host cell of claim 21 under conditions suitable for expression of the dimeric bispecific binding agent, and recovering the dimeric bispecific binding agent.

23. A bispecific binding agent comprised of two fusion proteins that each comprise, from N-terminus to C-terminus,
   a first antibody component that binds to a tumor antigen,
   a second antibody component that binds to CD3 on T cells, and
   a dimerization component comprising a sequence that is at least 90% identical to residues 1-32 of SEQ ID NO:1, such that the fusion proteins dimerize to form a homodimeric bispecific binding agent;
   wherein the homodimeric bispecific binding agent is characterized by a longer half-life as compared to an otherwise comparable bispecific binding agent that does not comprise the dimerization component.

24. The bispecific binding agent of claim 23, wherein the dimerization component comprises amino acid residues 1-32 of SEQ ID NO:1.

25. The bispecific binding agent of claim 23, wherein the first and second antibody components are scFvs.

26. The bispecific binding agent of claim 23, wherein the tumor antigen is GD2.

27. The bispecific binding agent of claim 23, wherein the bispecific binding agent has enhanced tumor antigen binding avidity as compared to an otherwise comparable bispecific binding agent that does not comprise the dimerization component.

28. The bispecific binding agent of claim 27, wherein the bispecific binding agent does not have significantly different binding avidity to T cells as compared to an otherwise comparable bispecific binding agent that does not comprise the dimerization component.

29. A method of killing tumor cells, the method comprising steps of
   contacting the tumor cells with a therapeutically effective amount of a bispecific binding agent, comprised of two fusion proteins that each comprise, from—N-terminus to C-terminus, a first antibody component that binds to a tumor antigen, a second antibody component that binds to CD3 on T cells, and a dimerization component comprising a human HNF-1α element, wherein the HNF-1α element comprises a sequence that is at least 90% identical to residues 1-32 of SEQ ID NO: 1, such that the bispecific binding agent is capable of dimerization to form a homodimer, the contacting being performed under conditions and for a time sufficient that T cells to which the homodimer has bound mediate killing of the tumor cells.

30. The method of claim 29, wherein the dimerization component comprises amino acid residues 1-32 of human HNF-1α.

31. The method of claim 29, wherein the first and second antibody components are scFvs.

32. The method of claim 29, wherein the tumor antigen is GD2.

33. The method of claim 29, wherein each of the fusion proteins comprise a sequence that is at least 90% identical to any one of SEQ ID NO: 2-23.

34. The method of claim 29, wherein each of the fusion proteins comprise a sequence that is selected from any one of SEQ ID NO: 2-23.

35. A method of inhibiting tumor growth, the method comprising steps of
   contacting a tumor with a therapeutically effective amount of a bispecific binding agent, comprised of two fusion proteins that each comprise, from—N-terminus to C-terminus, a first antibody component that binds to a tumor antigen, a second antibody component that binds to CD3 on T cells, and a dimerization component comprising a human HNF-1α element, wherein the HNF-1α element comprises a sequence that is at least 90% identical to residues 1-32 of SEQ ID NO: 1, such that the bispecific antibody is capable of dimerization to form a homodimer, the contacting being performed under conditions and for a time sufficient that T cells to which the homodimer has bound inhibit growth of a tumor.

36. The method of claim 35, wherein the dimerization component comprises amino acid residues 1-32 of human HNF-1α.

37. The method of claim 35, wherein the first and second antibody components are scFvs.

38. The method of claim 35, wherein the tumor antigen is GD2.

39. The method of claim 35, wherein each of the fusion proteins comprise a sequence that is at least 90% identical to any one of SEQ ID NO: 2-23.

40. The method of claim 35, wherein each of the fusion proteins comprise a sequence that is selected from any one of SEQ ID NO: 2-23.

* * * * *

UNITED STATES PATENT AND TRADEMARK OFFICE
CERTIFICATE OF CORRECTION

PATENT NO. : 9,802,995 B2
APPLICATION NO. : 14/776267
DATED : October 31, 2017
INVENTOR(S) : Mahiuddin Ahmed and Nai-Kong V. Cheung It is certified that error appears in the above-identified patent and that said Letters Patent is hereby corrected as shown below:

In the Claims

In Claim 29, Column 116, Line 8, reads "comprise, from—N-terminus" and should read "comprise, from N-terminus".

In Claim 35, Column 116, Line 38, reads "comprise, from—N-terminus" and should read "comprise, from N-terminus".

Signed and Sealed this
Eighth Day of May, 2018

Andrei Iancu
*Director of the United States Patent and Trademark Office*

SEQUENCE LISTING

<160> NUMBER OF SEQ ID NOS: 24

<210> SEQ ID NO 1
<211> LENGTH: 32
<212> TYPE: PRT
<213> ORGANISM: Artificial Sequence
<220> FEATURE:
<223> OTHER INFORMATION: Synthetic polypeptide sequence, human HNF-1
      alpha, amino acids 1-32

<400> SEQUENCE: 1

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

<210> SEQ ID NO 2
<211> LENGTH: 501
<212> TYPE: PRT
<213> ORGANISM: Artificial Sequence
<220> FEATURE:
<223> OTHER INFORMATION: Synthetic polypeptide sequence, 5HLBT:
      VHVL(5F11)-(G4S)3-VHVL(hOKT3)

<400> SEQUENCE: 2

```
Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Lys Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Thr Thr Val Pro Phe Ala Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Ser Asp Ile Glu Leu Thr Gln Ser Pro Ala Ile Met Ser
    130                 135                 140

Ala Ser Pro Gly Glu Lys Val Thr Met Thr Cys Ser Ala Ser Ser Ser
145                 150                 155                 160

Ile Ser Tyr Met His Trp Tyr Gln Gln Lys Pro Gly Thr Ser Pro Lys
                165                 170                 175

Arg Trp Ile Tyr Asp Thr Ser Lys Leu Ala Ser Gly Val Pro Ala Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Thr Tyr Tyr Cys His Gln Arg Ser Ser
    210                 215                 220

Tyr Pro Leu Thr Phe Gly Ala Gly Thr Lys Leu Glu Ile Lys Arg Ala
225                 230                 235                 240

Ser Thr Lys Gly Pro Gly Gly Gly Ser Gly Gly Gly Ser Gly
                245                 250                 255

Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
        355                 360                 365
```

```
Trp Gly Gln Gly Thr Pro Val Thr Val Ser Ser Gly Gly Gly Ser
            370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
    450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg
            500

<210> SEQ ID NO 3
<211> LENGTH: 501
<212> TYPE: PRT
<213> ORGANISM: Artificial Sequence
<220> FEATURE:
<223> OTHER INFORMATION: Synthetic polypeptide sequence, 5LHBT:
      VLVH(5F11)-(G4S)3-VHVL(hOKT3)

<400> SEQUENCE: 3

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Leu Thr
                85                  90                  95

Phe Gly Ala Gly Thr Lys Leu Glu Ile Lys Arg Gly Gly Gly Gly Ser
            100                 105                 110

Gly Gly Gly Gly Ser Gly Gly Gly Gly Ser Gln Val Gln Leu Gln Gln
            115                 120                 125

Ser Gly Pro Glu Leu Val Lys Pro Gly Ala Ser Val Lys Ile Ser Cys
    130                 135                 140

Lys Thr Ser Gly Tyr Lys Phe Thr Glu Tyr Thr Met His Trp Val Lys
145                 150                 155                 160

Gln Ser His Gly Lys Ser Leu Glu Trp Ile Gly Gly Ile Asn Pro Asn
                165                 170                 175

Asn Gly Gly Thr Asn Tyr Asn Gln Lys Phe Lys Gly Lys Ala Thr Leu
            180                 185                 190

Thr Val Asp Lys Ser Ser Thr Ala Tyr Met Glu Leu Arg Ser Leu
        195                 200                 205

Thr Ser Glu Asp Ser Ala Val Tyr Tyr Cys Ala Arg Asp Thr Thr Val
```

Pro Phe Ala Tyr Trp Gly Gln Gly Thr Thr Val Thr Val Ser Ser Ala
225                 230                 235                 240

Ser Thr Lys Gly Pro Gly Gly Gly Ser Gly Gly Gly Gly Ser Gly
            245                 250                 255

Gly Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
                355                 360                 365

Trp Gly Gln Gly Thr Pro Val Thr Val Ser Ser Gly Gly Gly Gly Ser
370                 375                 380

Gly Gly Gly Gly Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
                435                 440                 445

Ser Gly Val Pro Ser Arg Phe Ser Gly Ser Gly Ser Gly Thr Asp Tyr
                450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg
            500

<210> SEQ ID NO 4
<211> LENGTH: 501
<212> TYPE: PRT
<213> ORGANISM: Artificial Sequence
<220> FEATURE:
<223> OTHER INFORMATION: Synthetic polypeptide sequence, 5HLDS15BT:
      VHVL(5F11(S44C, A100C))-(G4S)3-VHVL(hOKT3)

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Lys Phe Thr Glu Tyr
                20                  25                  30

Thr Met His Trp Val Lys Gln Ser His Gly Lys Cys Leu Glu Trp Ile
            35                  40                  45

Gly Gly Ile Asn Pro Asn Gly Gly Thr Asn Tyr Asn Gln Lys Phe
        50                  55                  60

-continued

```
Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Asp Thr Thr Val Pro Phe Ala Tyr Trp Gly Gln Gly Thr Thr
                100                 105                 110

Val Thr Val Ser Ser Gly Gly Gly Gly Ser Gly Gly Gly Gly Ser Gly
                115                 120                 125

Gly Gly Gly Ser Asp Ile Glu Leu Thr Gln Ser Pro Ala Ile Met Ser
            130                 135                 140

Ala Ser Pro Gly Glu Lys Val Thr Met Thr Cys Ser Ala Ser Ser Ser
145                 150                 155                 160

Ile Ser Tyr Met His Trp Tyr Gln Gln Lys Pro Gly Thr Ser Pro Lys
                165                 170                 175

Arg Trp Ile Tyr Asp Thr Ser Lys Leu Ala Ser Gly Val Pro Ala Arg
                180                 185                 190

Phe Ser Gly Ser Gly Ser Gly Thr Ser Tyr Ser Leu Thr Ile Ser Ser
                195                 200                 205

Met Glu Ala Glu Asp Ala Ala Thr Tyr Tyr Cys His Gln Arg Ser Ser
210                 215                 220

Tyr Pro Leu Thr Phe Gly Cys Gly Thr Lys Leu Glu Ile Lys Arg Ala
225                 230                 235                 240

Ser Thr Lys Gly Pro Gly Gly Gly Gly Ser Gly Gly Gly Gly Ser Gly
                245                 250                 255

Gly Gly Gly Ser Gln Val Gln Leu Val Gln Ser Gly Gly Gly Val Val
            260                 265                 270

Gln Pro Gly Arg Ser Leu Arg Leu Ser Cys Lys Ala Ser Gly Tyr Thr
                275                 280                 285

Phe Thr Arg Tyr Thr Met His Trp Val Arg Gln Ala Pro Gly Lys Gly
                290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
                355                 360                 365

Trp Gly Gln Gly Thr Pro Val Thr Val Ser Ser Gly Gly Gly Gly Ser
                370                 375                 380

Gly Gly Gly Gly Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
                435                 440                 445

Ser Gly Val Pro Ser Arg Phe Ser Gly Ser Gly Ser Gly Thr Asp Tyr
                450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
```

Leu Gln Ile Thr Arg
            500

<210> SEQ ID NO 5
<211> LENGTH: 501
<212> TYPE: PRT
<213> ORGANISM: Artificial Sequence
<220> FEATURE:
<223> OTHER INFORMATION: Synthetic polypeptide sequence, 5LHDS15BT:
      VLVH(5F11(S44C, A100C))-(G4S)3-VHVL(hOKT3)

<400> SEQUENCE: 5

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Leu Thr
                85                  90                  95

Phe Gly Cys Gly Thr Lys Leu Glu Ile Lys Arg Gly Gly Gly Gly Ser
            100                 105                 110

Gly Gly Gly Gly Ser Gly Gly Gly Ser Gln Val Gln Leu Gln Gln
            115                 120                 125

Ser Gly Pro Glu Leu Val Lys Pro Gly Ala Ser Val Lys Ile Ser Cys
    130                 135                 140

Lys Thr Ser Gly Tyr Lys Phe Thr Glu Tyr Thr Met His Trp Val Lys
145                 150                 155                 160

Gln Ser His Gly Lys Cys Leu Glu Trp Ile Gly Gly Ile Asn Pro Asn
                165                 170                 175

Asn Gly Gly Thr Asn Tyr Asn Gln Lys Phe Lys Gly Lys Ala Thr Leu
            180                 185                 190

Thr Val Asp Lys Ser Ser Ser Thr Ala Tyr Met Glu Leu Arg Ser Leu
        195                 200                 205

Thr Ser Glu Asp Ser Ala Val Tyr Tyr Cys Ala Arg Asp Thr Thr Val
    210                 215                 220

Pro Phe Ala Tyr Trp Gly Gln Gly Thr Thr Val Thr Val Ser Ser Ala
225                 230                 235                 240

Ser Thr Lys Gly Pro Gly Gly Gly Ser Gly Gly Gly Gly Ser Gly
                245                 250                 255

Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

```
Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
        370                 375                 380

Gly Gly Gly Gly Ser Gly Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
        435                 440                 445

Ser Gly Val Pro Ser Arg Phe Ser Gly Ser Gly Ser Gly Thr Asp Tyr
    450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg
                500

<210> SEQ ID NO 6
<211> LENGTH: 491
<212> TYPE: PRT
<213> ORGANISM: Artificial Sequence
<220> FEATURE:
<223> OTHER INFORMATION: Synthetic polypeptide sequence, 5HLDS5BT:
      VHVL(5F11(S44C, A100C))-(G4S)-VHVL(hOKT3)

<400> SEQUENCE: 6

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Lys Phe Thr Glu Tyr
                20                  25                  30

Thr Met His Trp Val Lys Gln Ser His Gly Lys Cys Leu Glu Trp Ile
            35                  40                  45

Gly Gly Ile Asn Pro Asn Asn Gly Gly Thr Asn Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Thr Thr Val Pro Phe Ala Tyr Trp Gly Gln Gly Thr Thr
            100                 105                 110

Val Thr Val Ser Ser Gly Gly Gly Gly Ser Asp Ile Glu Leu Thr Gln
        115                 120                 125

Ser Pro Ala Ile Met Ser Ala Ser Pro Gly Glu Lys Val Thr Met Thr
    130                 135                 140

Cys Ser Ala Ser Ser Ser Ile Ser Tyr Met His Trp Tyr Gln Gln Lys
145                 150                 155                 160

Pro Gly Thr Ser Pro Lys Arg Trp Ile Tyr Asp Thr Ser Lys Leu Ala
                165                 170                 175

Ser Gly Val Pro Ala Arg Phe Ser Gly Ser Gly Ser Gly Thr Ser Tyr
            180                 185                 190
```

```
Ser Leu Thr Ile Ser Ser Met Glu Ala Glu Asp Ala Ala Thr Tyr Tyr
            195                 200                 205

Cys His Gln Arg Ser Ser Tyr Pro Leu Thr Phe Gly Cys Gly Thr Lys
    210                 215                 220

Leu Glu Ile Lys Arg Ala Ser Thr Lys Gly Pro Gly Gly Gly Ser
225                 230                 235                 240

Gly Gly Gly Gly Ser Gly Gly Gly Ser Gln Val Gln Leu Val Gln
                245                 250                 255

Ser Gly Gly Gly Val Val Gln Pro Gly Arg Ser Leu Arg Leu Ser Cys
                260                 265                 270

Lys Ala Ser Gly Tyr Thr Phe Thr Arg Tyr Thr Met His Trp Val Arg
                275                 280                 285

Gln Ala Pro Gly Lys Gly Leu Glu Trp Ile Gly Tyr Ile Asn Pro Ser
            290                 295                 300

Arg Gly Tyr Thr Asn Tyr Asn Gln Lys Phe Lys Asp Arg Phe Thr Ile
305                 310                 315                 320

Ser Arg Asp Asn Ser Lys Asn Thr Ala Phe Leu Gln Met Asp Ser Leu
                325                 330                 335

Arg Pro Glu Asp Thr Gly Val Tyr Phe Cys Ala Arg Tyr Tyr Asp Asp
            340                 345                 350

His Tyr Cys Leu Asp Tyr Trp Gly Gln Gly Thr Pro Val Thr Val Ser
            355                 360                 365

Ser Gly Gly Gly Gly Ser Gly Gly Gly Gly Ser Gly Gly Gly Gly Ser
    370                 375                 380

Asp Ile Gln Met Thr Gln Ser Pro Ser Ser Leu Ser Ala Ser Val Gly
385                 390                 395                 400

Asp Arg Val Thr Ile Thr Cys Ser Ala Ser Ser Ser Val Ser Tyr Met
                405                 410                 415

Asn Trp Tyr Gln Gln Thr Pro Gly Lys Ala Pro Lys Arg Trp Ile Tyr
            420                 425                 430

Asp Thr Ser Lys Leu Ala Ser Gly Val Pro Ser Arg Phe Ser Gly Ser
            435                 440                 445

Gly Ser Gly Thr Asp Tyr Thr Phe Thr Ile Ser Ser Leu Gln Pro Glu
    450                 455                 460

Asp Ile Ala Thr Tyr Tyr Cys Gln Gln Trp Ser Ser Asn Pro Phe Thr
465                 470                 475                 480

Phe Gly Gln Gly Thr Lys Leu Gln Ile Thr Arg
                485                 490

<210> SEQ ID NO 7
<211> LENGTH: 491
<212> TYPE: PRT
<213> ORGANISM: Artificial Sequence
<220> FEATURE:
<223> OTHER INFORMATION: Synthetic polypeptide sequence, 5LHDS5BT:
      VLVH(5F11(S44C, A100C))-(G4S)-VHVL(hOKT3)

<400> SEQUENCE: 7

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ile Ser Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
```

```
            50                  55                  60
Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Ser Ser Tyr Pro Leu Thr
                 85                  90                  95

Phe Gly Cys Gly Thr Lys Leu Glu Ile Lys Arg Gly Gly Gly Gly Ser
                100                 105                 110

Gln Val Gln Leu Gln Gln Ser Gly Pro Glu Leu Val Lys Pro Gly Ala
            115                 120                 125

Ser Val Lys Ile Ser Cys Lys Thr Ser Gly Tyr Lys Phe Thr Glu Tyr
130                 135                 140

Thr Met His Trp Val Lys Gln Ser His Gly Lys Cys Leu Glu Trp Ile
145                 150                 155                 160

Gly Gly Ile Asn Pro Asn Asn Gly Gly Thr Asn Tyr Asn Gln Lys Phe
                165                 170                 175

Lys Gly Lys Ala Thr Leu Thr Val Asp Lys Ser Ser Thr Ala Tyr
            180                 185                 190

Met Glu Leu Arg Ser Leu Thr Ser Glu Asp Ser Ala Val Tyr Tyr Cys
        195                 200                 205

Ala Arg Asp Thr Thr Val Pro Phe Ala Tyr Trp Gly Gln Gly Thr Thr
210                 215                 220

Val Thr Val Ser Ser Ala Ser Thr Lys Gly Pro Gly Gly Gly Gly Ser
225                 230                 235                 240

Gly Gly Gly Gly Ser Gly Gly Gly Ser Gln Val Gln Leu Val Gln
                245                 250                 255

Ser Gly Gly Gly Val Val Gln Pro Gly Arg Ser Leu Arg Leu Ser Cys
        260                 265                 270

Lys Ala Ser Gly Tyr Thr Phe Thr Arg Tyr Thr Met His Trp Val Arg
            275                 280                 285

Gln Ala Pro Gly Lys Gly Leu Glu Trp Ile Gly Tyr Ile Asn Pro Ser
        290                 295                 300

Arg Gly Tyr Thr Asn Tyr Asn Gln Lys Phe Lys Asp Arg Phe Thr Ile
305                 310                 315                 320

Ser Arg Asp Asn Ser Lys Asn Thr Ala Phe Leu Gln Met Asp Ser Leu
                325                 330                 335

Arg Pro Glu Asp Thr Gly Val Tyr Phe Cys Ala Arg Tyr Tyr Asp Asp
            340                 345                 350

His Tyr Cys Leu Asp Tyr Trp Gly Gln Gly Thr Pro Val Thr Val Ser
                355                 360                 365

Ser Gly Gly Gly Gly Ser Gly Gly Gly Ser Gly Gly Gly Gly Ser
370                 375                 380

Asp Ile Gln Met Thr Gln Ser Pro Ser Ser Leu Ser Ala Ser Val Gly
385                 390                 395                 400

Asp Arg Val Thr Ile Thr Cys Ser Ala Ser Ser Ser Val Ser Tyr Met
                405                 410                 415

Asn Trp Tyr Gln Gln Thr Pro Gly Lys Ala Pro Lys Arg Trp Ile Tyr
            420                 425                 430

Asp Thr Ser Lys Leu Ala Ser Gly Val Pro Ser Arg Phe Ser Gly Ser
            435                 440                 445

Gly Ser Gly Thr Asp Tyr Thr Phe Thr Ile Ser Ser Leu Gln Pro Glu
        450                 455                 460

Asp Ile Ala Thr Tyr Tyr Cys Gln Gln Trp Ser Ser Asn Pro Phe Thr
465                 470                 475                 480
```

```
Phe Gly Gln Gly Thr Lys Leu Gln Ile Thr Arg
                485                 490

<210> SEQ ID NO 8
<211> LENGTH: 501
<212> TYPE: PRT
<213> ORGANISM: Artificial Sequence
<220> FEATURE:
<223> OTHER INFORMATION: Synthetic polypeptide sequence, Y-BT:
      VHVL(5F11(S44C, A100C, P104Y))-(G4S)-VHVL(hOKT3)

<400> SEQUENCE: 8

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Lys Phe Thr Glu Tyr
            20                  25                  30

Thr Met His Trp Val Lys Gln Ser His Gly Lys Cys Leu Glu Trp Ile
        35                  40                  45

Gly Gly Ile Asn Pro Asn Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Thr Thr Val Pro Tyr Ala Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ala Ile Met Ser
    130                 135                 140

Ala Ser Pro Gly Glu Lys Val Thr Met Thr Cys Ser Ala Ser Ser Ser
145                 150                 155                 160

Ile Ser Tyr Met His Trp Tyr Gln Gln Lys Pro Gly Thr Ser Pro Lys
                165                 170                 175

Arg Trp Ile Tyr Asp Thr Ser Lys Leu Ala Ser Gly Val Pro Ala Arg
            180                 185                 190

Phe Ser Gly Ser Gly Ser Gly Thr Ser Tyr Ser Leu Thr Ile Ser Ser
        195                 200                 205

Met Glu Ala Glu Asp Ala Ala Thr Tyr Tyr Cys His Gln Arg Ser Ser
    210                 215                 220

Tyr Pro Leu Thr Phe Gly Cys Gly Thr Lys Leu Glu Ile Lys Arg Ala
225                 230                 235                 240

Ser Thr Lys Gly Pro Gly Gly Gly Gly Ser Gly Gly Gly Gly Ser Gly
                245                 250                 255

Gly Gly Gly Ser Gln Val Gln Leu Val Gln Ser Gly Gly Gly Val Val
            260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
```

```
              340             345             350
Val Tyr Phe Cys Ala Arg Tyr Tyr Asp Asp His Tyr Cys Leu Asp Tyr
            355             360             365

Trp Gly Gln Gly Thr Pro Val Thr Val Ser Ser Gly Gly Gly Ser
    370             375             380

Gly Gly Gly Ser Gly Gly Gly Ser Asp Ile Gln Met Thr Gln
385             390             395             400

Ser Pro Ser Ser Leu Ser Ala Ser Val Gly Asp Arg Val Thr Ile Thr
                405             410             415

Cys Ser Ala Ser Ser Ser Val Ser Tyr Met Asn Trp Tyr Gln Gln Thr
                420             425             430

Pro Gly Lys Ala Pro Lys Arg Trp Ile Tyr Asp Thr Ser Lys Leu Ala
            435             440             445

Ser Gly Val Pro Ser Arg Phe Ser Gly Ser Gly Ser Gly Thr Asp Tyr
            450             455             460

Thr Phe Thr Ile Ser Ser Leu Gln Pro Glu Asp Ile Ala Thr Tyr Tyr
465             470             475             480

Cys Gln Gln Trp Ser Ser Asn Pro Phe Thr Phe Gly Gln Gly Thr Lys
                485             490             495

Leu Gln Ile Thr Arg
            500

<210> SEQ ID NO 9
<211> LENGTH: 501
<212> TYPE: PRT
<213> ORGANISM: Artificial Sequence
<220> FEATURE:
<223> OTHER INFORMATION: Synthetic polypeptide sequence, Q-BT:
      VHVL(5F11(E31Q))-(G4S)-VHVL(hOKT3)

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Lys Phe Thr Gln Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Thr Thr Val Pro Phe Ala Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Ser Pro Ala Ile Met Ser
    130                 135                 140

Ala Ser Pro Gly Glu Lys Val Thr Met Thr Cys Ser Ala Ser Ser Ser
145                 150                 155                 160

Ile Ser Tyr Met His Trp Tyr Gln Gln Lys Pro Gly Thr Ser Pro Lys
                165                 170                 175

Arg Trp Ile Tyr Asp Thr Ser Lys Leu Ala Ser Gly Val Pro Ala Arg
            180                 185                 190
```

```
Phe Ser Gly Ser Gly Ser Gly Thr Ser Tyr Ser Leu Thr Ile Ser Ser
            195                 200                 205

Met Glu Ala Glu Asp Ala Ala Thr Tyr Tyr Cys His Gln Arg Ser Ser
    210                 215                 220

Tyr Pro Leu Thr Phe Gly Ala Gly Thr Lys Leu Glu Ile Lys Arg Ala
225                 230                 235                 240

Ser Thr Lys Gly Pro Gly Gly Gly Ser Gly Gly Gly Ser Gly
                245                 250                 255

Gly Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
    370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg
            500

<210> SEQ ID NO 10
<211> LENGTH: 550
<212> TYPE: PRT
<213> ORGANISM: Artificial Sequence
<220> FEATURE:
<223> OTHER INFORMATION: Synthetic polypeptide sequence, Y-BT-HDD: Y-BT
      with a HNF-1 alpha dimerization domain (HDD)

<400> SEQUENCE: 10

Gln Val Gln Leu Gln Gln Ser Gly Pro Glu Leu Val Lys Pro Gly Ala
1               5                   10                  15

Ser Val Lys Ile Ser Cys L

```
Gly Gly Ile Asn Pro Asn Asn Gly Gly Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Thr Thr Val Pro Tyr Ala Tyr Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Gly Ser Asp Ile Glu Leu Thr Gln Ser Pro Ala Ile Met Ser
130                 135                 140

Ala Ser Pro Gly Glu Lys Val Thr Met Thr Cys Ser Ala Ser Ser Ser
145                 150                 155                 160

Ile Ser Tyr Met His Trp Tyr Gln Gln Lys Pro Gly Thr Ser Pro Lys
                165                 170                 175

Arg Trp Ile Tyr Asp Thr Ser Lys Leu Ala Ser Gly Val Pro Ala Arg
                180                 185                 190

Phe Ser Gly Ser Gly Ser Gly Thr Ser Tyr Ser Leu Thr Ile Ser Ser
            195                 200                 205

Met Glu Ala Glu Asp Ala Ala Thr Tyr Tyr Cys His Gln Arg Ser Ser
    210                 215                 220

Tyr Pro Leu Thr Phe Gly Cys Gly Thr Lys Leu Glu Ile Lys Arg Ala
225                 230                 235                 240

Ser Thr Lys Gly Pro Gly Gly Gly Ser Gly Gly Gly Gly Ser Gly
                245                 250                 255

Gly Gly Ser Gln Val Gln Leu Val Gln Ser Gly Gly Gly Val Val
            260                 265                 270

Gln Pro Gly Arg Ser Leu Arg Leu Ser Cys Lys Ala Ser Gly Tyr Thr
                275                 280                 285

Phe Thr Arg Tyr Thr Met His Trp Val Arg Gln Ala Pro Gly Lys Gly
                290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
    370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
                435                 440                 445

Ser Gly Val Pro Ser Arg Phe Ser Gly Ser Gly Ser Gly Thr Asp Tyr
            450                 455                 460
```

-continued

```
Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
            485                 490                 495

Leu Gln Ile Thr Arg Thr Pro Leu Gly Asp Thr Thr His Thr Ser Gly
        500                 505                 510

Met Val Ser Lys Leu Ser Gln Leu Gln Thr Glu Leu Leu Ala Ala Leu
    515                 520                 525

Leu Glu Ser Gly Leu Ser Lys Glu Ala Leu Ile Gln Ala Leu Gly Glu
    530                 535                 540

Gly Ser Gly Gly Ala Pro
545                 550

<210> SEQ ID NO 11
<211> LENGTH: 550
<212> TYPE: PRT
<213> ORGANISM: Artificial Sequence
<220> FEATURE:
<223> OTHER INFORMATION: Synthetic polypeptide sequence, 3LHBT-HDD:
      VLVH(hu3F8v1)-(G4S)3-VHVL(hOKT3)-HDD

<400> SEQUENCE: 11

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Gly Ser Gly
                245                 250                 255

Gly Gly Gly Ser Gln Val Gln Leu Val Gln Ser Gly Gly Gly Val Val
            260                 265                 270
```

```
Gln Pro Gly Arg Ser Leu Arg Leu Ser Cys Lys Ala Ser Gly Tyr Thr
            275                 280                 285
Phe Thr Arg Tyr Thr Met His Trp Val Arg Gln Ala Pro Gly Lys Gly
        290                 295                 300
Leu Glu Trp Ile Gly Tyr Ile Asn Pro Ser Arg Gly Tyr Thr Asn Tyr
305                 310                 315                 320
Asn Gln Lys Phe Lys Asp Arg Phe Thr Ile Ser Arg Asp Asn Ser Lys
                325                 330                 335
Asn Thr Ala Phe Leu Gln Met Asp Ser Leu Arg Pro Glu Asp Thr Gly
            340                 345                 350
Val Tyr Phe Cys Ala Arg Tyr Tyr Asp Asp His Tyr Cys Leu Asp Tyr
        355                 360                 365
Trp Gly Gln Gly Thr Pro Val Thr Val Ser Ser Gly Gly Gly Gly Ser
370                 375                 380
Gly Gly Gly Gly Ser Gly Gly Gly Ser Asp Ile Gln Met Thr Gln
385                 390                 395                 400
Ser Pro Ser Ser Leu Ser Ala Ser Val Gly Asp Arg Val Thr Ile Thr
                405                 410                 415
Cys Ser Ala Ser Ser Val Ser Tyr Met Asn Trp Tyr Gln Gln Thr
            420                 425                 430
Pro Gly Lys Ala Pro Lys Arg Trp Ile Tyr Asp Thr Ser Lys Leu Ala
        435                 440                 445
Ser Gly Val Pro Ser Arg Phe Ser Gly Ser Gly Ser Gly Thr Asp Tyr
450                 455                 460
Thr Phe Thr Ile Ser Ser Leu Gln Pro Glu Asp Ile Ala Thr Tyr Tyr
465                 470                 475                 480
Cys Gln Gln Trp Ser Ser Asn Pro Phe Thr Phe Gly Gln Gly Thr Lys
                485                 490                 495
Leu Gln Ile Thr Arg Thr Pro Leu Gly Asp Thr Thr His Thr Ser Gly
            500                 505                 510
Met Val Ser Lys Leu Ser Gln Leu Gln Thr Glu Leu Leu Ala Ala Leu
        515                 520                 525
Leu Glu Ser Gly Leu Ser Lys Glu Ala Leu Ile Gln Ala Leu Gly Glu
530                 535                 540
Gly Ser Gly Gly Ala Pro
545                 550

<210> SEQ ID NO 12
<211> LENGTH: 550
<212> TYPE: PRT
<213> ORGANISM: Artificial Sequence
<220> FEATURE:
<223> OTHER INFORMATION: Synthetic polypeptide sequence,
      3LHBT(D32H)-HDD: VLVH(hu3F8v1(D32H))-(G4S)3-VHVL(hOKT3)-HDD

<400> SEQUENCE: 12

Glu Ile Val Met Thr Gln Thr Pro Ala Thr Leu Ser Val Ser Ala Gly
1               5                   10                  15
Glu Arg Val Thr Ile Thr Cys Lys Ala Ser Gln Ser Val Ser Asn His
            20                  25                  30
Val Thr Trp Tyr Gln Gln Lys Pro Gly Gln Ala Pro Arg Leu Leu Ile
        35                  40                  45
Tyr Ser Ala Ser Asn Arg Tyr Ser Gly Val Pro Ala Arg Phe Ser Gly
    50                  55                  60
Ser Gly Tyr Gly Thr Glu Phe Thr Phe Thr Ile Ser Ser Val Gln Ser
```

```
                65                  70                  75                  80
            Glu Asp Phe Ala Val Tyr Phe Cys Gln Gln Asp Tyr Ser Ser Phe Gly
                                85                  90                  95
            Gln Gly Thr Lys Leu Glu Ile Lys Arg Gly Gly Gly Ser Gly Gly
                        100                 105                 110
            Gly Gly Ser Gly Gly Gly Ser Gln Val Gln Leu Val Glu Ser Gly
                        115                 120                 125
            Pro Gly Val Val Gln Pro Gly Arg Ser Leu Arg Ile Ser Cys Ala Val
                        130                 135                 140
            Ser Gly Phe Ser Val Thr Asn Tyr Gly Val His Trp Val Arg Gln Pro
            145                 150                 155                 160
            Pro Gly Lys Gly Leu Glu Trp Leu Gly Val Ile Trp Ala Gly Gly Ile
                        165                 170                 175
            Thr Asn Tyr Asn Ser Ala Phe Met Ser Arg Leu Thr Ile Ser Lys Asp
                        180                 185                 190
            Asn Ser Lys Asn Thr Val Tyr Leu Gln Met Asn Ser Leu Arg Ala Glu
                        195                 200                 205
            Asp Thr Ala Met Tyr Tyr Cys Ala Ser Arg Gly Gly His Tyr Gly Tyr
                        210                 215                 220
            Ala Leu Asp Tyr Trp Gly Gln Gly Thr Leu Val Thr Val Ser Ser Ala
            225                 230                 235                 240
            Ser Thr Lys Gly Pro Gly Gly Gly Ser Gly Gly Gly Ser
                        245                 250                 255
            Gly Gly Gly Ser Gln Val Gln Leu Val Gln Ser Gly Gly Val Val
                        260                 265                 270
            Gln Pro Gly Arg Ser Leu Arg Leu Ser Cys Lys Ala Ser Gly Tyr Thr
                        275                 280                 285
            Phe Thr Arg Tyr Thr Met His Trp Val Arg Gln Ala Pro Gly Lys Gly
                        290                 295                 300
            Leu Glu Trp Ile Gly Tyr Ile Asn Pro Ser Arg Gly Tyr Thr Asn Tyr
            305                 310                 315                 320
            Asn Gln Lys Phe Lys Asp Arg Phe Thr Ile Ser Arg Asp Asn Ser Lys
                        325                 330                 335
            Asn Thr Ala Phe Leu Gln Met Asp Ser Leu Arg Pro Glu Asp Thr Gly
                        340                 345                 350
            Val Tyr Phe Cys Ala Arg Tyr Tyr Asp Asp His Tyr Cys Leu Asp Tyr
                        355                 360                 365
            Trp Gly Gln Gly Thr Pro Val Thr Val Ser Ser Gly Gly Gly Ser
            370                 375                 380
            Gly Gly Gly Gly Ser Gly Gly Gly Ser Asp Ile Gln Met Thr Gln
            385                 390                 395                 400
            Ser Pro Ser Ser Leu Ser Ala Ser Val Gly Asp Arg Val Thr Ile Thr
                        405                 410                 415
            Cys Ser Ala Ser Ser Ser Val Ser Tyr Met Asn Trp Tyr Gln Gln Thr
                        420                 425                 430
            Pro Gly Lys Ala Pro Lys Arg Trp Ile Tyr Asp Thr Ser Lys Leu Ala
                        435                 440                 445
            Ser Gly Val Pro Ser Arg Phe Ser Gly Ser Gly Ser Gly Thr Asp Tyr
                        450                 455                 460
            Thr Phe Thr Ile Ser Ser Leu Gln Pro Glu Asp Ile Ala Thr Tyr Tyr
            465                 470                 475                 480
            Cys Gln Gln Trp Ser Ser Asn Pro Phe Thr Phe Gly Gln Gly Thr Lys
                        485                 490                 495
```

```
Leu Gln Ile Thr Arg Thr Pro Leu Gly Asp Thr Thr His Thr Ser Gly
                500                 505                 510

Met Val Ser Lys Leu Ser Gln Leu Gln Thr Glu Leu Ala Ala Leu
            515                 520                 525

Leu Glu Ser Gly Leu Ser Lys Glu Ala Leu Ile Gln Ala Leu Gly Glu
        530                 535                 540

Gly Ser Gly Gly Ala Pro
545                 550

<210> SEQ ID NO 13
<211> LENGTH: 550
<212> TYPE: PRT
<213> ORGANISM: Artificial Sequence
<220> FEATURE:
<223> OTHER INFORMATION: Synthetic polypeptide sequence,
      3LHBT(E1K,D32H)-HDD: VLVH(hu3F8v1(E1K,D32H))-(G4S)3-
      VHVL(hOKT3)-HDD

<400> SEQUENCE: 13

Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
    130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Gly Ser Gly Gly Gly Gly Ser Gly
                245                 250                 255

Gly Gly Gly Ser Gln Val Gln Leu Val Gln Ser Gly Gly Gly Val Val
            260                 265                 270

Gln Pro Gly Arg Ser Leu Arg Leu Ser Cys Lys Ala Ser Gly Tyr Thr
        275                 280                 285
```

```
Phe Thr Arg Tyr Thr Met His Trp Val Arg Gln Ala Pro Gly Lys Gly
    290                 295                 300
Leu Glu Trp Ile Gly Tyr Ile Asn Pro Ser Arg Gly Tyr Thr Asn Tyr
305                 310                 315                 320
Asn Gln Lys Phe Lys Asp Arg Phe Thr Ile Ser Arg Asp Asn Ser Lys
                325                 330                 335
Asn Thr Ala Phe Leu Gln Met Asp Ser Leu Arg Pro Glu Asp Thr Gly
                340                 345                 350
Val Tyr Phe Cys Ala Arg Tyr Tyr Asp Asp His Tyr Cys Leu Asp Tyr
            355                 360                 365
Trp Gly Gln Gly Thr Pro Val Thr Val Ser Ser Gly Gly Gly Gly Ser
370                 375                 380
Gly Gly Gly Gly Ser Gly Gly Gly Gly Ser Asp Ile Gln Met Thr Gln
385                 390                 395                 400
Ser Pro Ser Ser Leu Ser Ala Ser Val Gly Asp Arg Val Thr Ile Thr
                405                 410                 415
Cys Ser Ala Ser Ser Ser Val Ser Tyr Met Asn Trp Tyr Gln Gln Thr
            420                 425                 430
Pro Gly Lys Ala Pro Lys Arg Trp Ile Tyr Asp Thr Ser Lys Leu Ala
                435                 440                 445
Ser Gly Val Pro Ser Arg Phe Ser Gly Ser Gly Ser Gly Thr Asp Tyr
450                 455                 460
Thr Phe Thr Ile Ser Ser Leu Gln Pro Glu Asp Ile Ala Thr Tyr Tyr
465                 470                 475                 480
Cys Gln Gln Trp Ser Ser Asn Pro Phe Thr Phe Gly Gln Gly Thr Lys
                485                 490                 495
Leu Gln Ile Thr Arg Thr Pro Leu Gly Asp Thr Thr His Thr Ser Gly
            500                 505                 510
Met Val Ser Lys Leu Ser Gln Leu Gln Thr Glu Leu Leu Ala Ala Leu
                515                 520                 525
Leu Glu Ser Gly Leu Ser Lys Glu Ala Leu Ile Gln Ala Leu Gly Glu
            530                 535                 540
Gly Ser Gly Gly Ala Pro
545                 550

<210> SEQ ID NO 14
<211> LENGTH: 550
<212> TYPE: PRT
<213> ORGANISM: Artificial Sequence
<220> FEATURE:
<223> OTHER INFORMATION: Synthetic polypeptide sequence,
      3LHBT(E1K,D32H,G54I)-HDD: VLVH(hu3F8v1(E1K,D32H,G54I))-
      (G4S)3-VHVL(hOKT3)-HDD

<400> SEQUENCE: 14

Lys Ile Val Met Thr Gln Thr Pro Ala Thr Leu Ser Val Ser Ala Gly
1                5                  10                  15
Glu Arg Val Thr Ile Thr Cys Lys Ala Ser Gln Ser Val Ser Asn His
                20                  25                  30
Val Thr Trp Tyr Gln Gln Lys Pro Gly Gln Ala Pro Arg Leu Leu Ile
            35                  40                  45
Tyr Ser Ala Ser Asn Arg Tyr Ser Gly Val Pro Ala Arg Phe Ser Gly
        50                  55                  60
Ser Gly Tyr Gly Thr Glu Phe Thr Phe Thr Ile Ser Ser Val Gln Ser
65                  70                  75                  80
Glu Asp Phe Ala Val Tyr Phe Cys Gln Gln Asp Tyr Ser Ser Phe Gly
```

```
            85                  90                  95
Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
            130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Met Tyr Tyr Cys Ala Ser Arg Gly Gly His Tyr Gly Tyr
            210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Gly Ser Gly Gly Gly Gly Ser Gly
                245                 250                 255

Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
            290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
            325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
            370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
            405                 410                 415

Cys Ser Ala Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
            450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
            485                 490                 495

Leu Gln Ile Thr Arg Thr Pro Leu Gly Asp Thr Thr His Thr Ser Gly
            500                 505                 510
```

```
Met Val Ser Lys Leu Ser Gln Leu Gln Thr Glu Leu Leu Ala Ala Leu
            515                 520                 525

Leu Glu Ser Gly Leu Ser Lys Glu Ala Leu Ile Gln Ala Leu Gly Glu
            530                 535                 540

Gly Ser Gly Gly Ala Pro
545                 550

<210> SEQ ID NO 15
<211> LENGTH: 550
<212> TYPE: PRT
<213> ORGANISM: Artificial Sequence
<220> FEATURE:
<223> OTHER INFORMATION: Synthetic polypeptide sequence, 3LHBTv5-HDD:
      VLVH(hu3F8v5)-(G4S)3-VHVL(hOKT3)-HDD

<400> SEQUENCE: 15

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly Gly
            100                 105                 110

Gly Gly Ser Gly Gly Gly Ser Gln Val Gln Leu Val Glu Ser Gly
        115                 120                 125

Pro Gly Val Val Gln Pro Gly Arg Ser Leu Arg Leu Ser Cys Ala Val
            130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Gly Ser Gly
                245                 250                 255

Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
```

```
                305                 310                 315                 320
Asn Gln Lys Phe Lys Asp Arg Phe Thr Ile Ser Arg Asp Asn Ser Lys
                    325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
        370                 375                 380

Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
        450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg Thr Pro Leu Gly Asp Thr Thr His Thr Ser Gly
                500                 505                 510

Met Val Ser Lys Leu Ser Gln Leu Gln Thr Glu Leu Leu Ala Ala Leu
            515                 520                 525

Leu Glu Ser Gly Leu Ser Lys Glu Ala Leu Ile Gln Ala Leu Gly Glu
        530                 535                 540

Gly Ser Gly Gly Ala Pro
545                 550

<210> SEQ ID NO 16
<211> LENGTH: 550
<212> TYPE: PRT
<213> ORGANISM: Artificial Sequence
<220> FEATURE:
<223> OTHER INFORMATION: Synthetic polypeptide sequence,
     3LHBTv5(D32H)-HDD: VLVH(hu3F8v5(D32H))-(G4S)3-VHVL(hOKT3)-HDD

<400> SEQUENCE: 16

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
                100                 105                 110
```

-continued

```
Gly Gly Ser Gly Gly Gly Ser Gln Val Gln Leu Val Glu Ser Gly
            115                 120                 125
Pro Gly Val Val Gln Pro Gly Arg Ser Leu Arg Leu Ser Cys Ala Val
130                 135                 140
Ser Gly Phe Ser Val Thr Asn Tyr Gly Val His Trp Val Arg Gln Pro
145                 150                 155                 160
Pro Gly Lys Gly Leu Glu Trp Leu Gly Val Ile Trp Ala Gly Gly Ile
                165                 170                 175
Thr Asn Tyr Asn Ser Ser Val Lys Gly Arg Leu Thr Ile Ser Lys Asp
            180                 185                 190
Asn Ser Lys Asn Thr Val Tyr Leu Gln Met Asn Ser Leu Arg Ala Glu
        195                 200                 205
Asp Thr Ala Val Tyr Tyr Cys Ala Ser Arg Gly Gly His Tyr Gly Tyr
    210                 215                 220
Ala Leu Asp Tyr Trp Gly Gln Gly Thr Leu Val Thr Val Ser Ser Ala
225                 230                 235                 240
Ser Thr Lys Gly Pro Gly Gly Gly Ser Gly Gly Gly Ser Gly
                245                 250                 255
Gly Gly Gly Ser Gln Val Gln Leu Val Gln Ser Gly Gly Val Val
            260                 265                 270
Gln Pro Gly Arg Ser Leu Arg Leu Ser Cys Lys Ala Ser Gly Tyr Thr
    275                 280                 285
Phe Thr Arg Tyr Thr Met His Trp Val Arg Gln Ala Pro Gly Lys Gly
290                 295                 300
Leu Glu Trp Ile Gly Tyr Ile Asn Pro Ser Arg Gly Tyr Thr Asn Tyr
305                 310                 315                 320
Asn Gln Lys Phe Lys Asp Arg Phe Thr Ile Ser Arg Asp Asn Ser Lys
                325                 330                 335
Asn Thr Ala Phe Leu Gln Met Asp Ser Leu Arg Pro Glu Asp Thr Gly
            340                 345                 350
Val Tyr Phe Cys Ala Arg Tyr Tyr Asp Asp His Tyr Cys Leu Asp Tyr
        355                 360                 365
Trp Gly Gln Gly Thr Pro Val Thr Val Ser Ser Gly Gly Gly Gly Ser
    370                 375                 380
Gly Gly Gly Gly Ser Gly Gly Gly Ser Asp Ile Gln Met Thr Gln
385                 390                 395                 400
Ser Pro Ser Ser Leu Ser Ala Ser Val Gly Asp Arg Val Thr Ile Thr
                405                 410                 415
Cys Ser Ala Ser Ser Val Ser Tyr Met Asn Trp Tyr Gln Gln Thr
            420                 425                 430
Pro Gly Lys Ala Pro Lys Arg Trp Ile Tyr Asp Thr Ser Lys Leu Ala
        435                 440                 445
Ser Gly Val Pro Ser Arg Phe Ser Gly Ser Gly Ser Gly Thr Asp Tyr
    450                 455                 460
Thr Phe Thr Ile Ser Ser Leu Gln Pro Glu Asp Ile Ala Thr Tyr Tyr
465                 470                 475                 480
Cys Gln Gln Trp Ser Ser Asn Pro Phe Thr Phe Gly Gln Gly Thr Lys
                485                 490                 495
Leu Gln Ile Thr Arg Thr Pro Leu Gly Asp Thr Thr His Thr Ser Gly
            500                 505                 510
Met Val Ser Lys Leu Ser Gln Leu Gln Thr Glu Leu Leu Ala Ala Leu
        515                 520                 525
Leu Glu Ser Gly Leu Ser Lys Glu Ala Leu Ile Gln Ala Leu Gly Glu
```

```
                   530                 535                 540
Gly Ser Gly Gly Ala Pro
545                 550

<210> SEQ ID NO 17
<211> LENGTH: 550
<212> TYPE: PRT
<213> ORGANISM: Artificial Sequence
<220> FEATURE:
<223> OTHER INFORMATION: Synthetic polypeptide sequence,
      3LHBTv5(E1K,D32H)-HDD: VLVH(hu3F8v5(E1K,D32H))-(G4S)3-
      VHVL(hOKT3)-HDD

<400> SEQUENCE: 17

Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly Gly
            100                 105                 110

Gly Gly Ser Gly Gly Gly Ser Gln Val Gln Leu Val Glu Ser Gly
        115                 120                 125

Pro Gly Val Val Gln Pro Gly Arg Ser Leu Arg Leu Ser Cys Ala Val
        130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Gly Gly Ile
                165                 170                 175

Thr Asn Tyr Asn Ser Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Gly Ser Gly
                245                 250                 255

Gly Gly Gly Ser Gln Val Gln Leu Val Gln Ser Gly Gly Val Val
        260                 265                 270

Gln Pro Gly Arg Ser Leu Arg Leu Ser Cys Lys Ala Ser Gly Tyr Thr
    275                 280                 285

Phe Thr Arg Tyr Thr Met His Trp Val Arg Gln Ala Pro Gly Lys Gly
        290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
            325                 330                 335
```

```
Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
            450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg Thr Pro Leu Gly Asp Thr Thr His Thr Ser Gly
            500                 505                 510

Met Val Ser Lys Leu Ser Gln Leu Gln Thr Glu Leu Leu Ala Ala Leu
            515                 520                 525

Leu Glu Ser Gly Leu Ser Lys Glu Ala Leu Ile Gln Ala Leu Gly Glu
            530                 535                 540

Gly Ser Gly Gly Ala Pro
545                 550

<210> SEQ ID NO 18
<211> LENGTH: 550
<212> TYPE: PRT
<213> ORGANISM: Artificial Sequence
<220> FEATURE:
<223> OTHER INFORMATION: Synthetic polypeptide sequence,
      3LHBTv5(E1K,D32H,G54I)-HDD: VLVH(hu3F8v5(E1K,D32H,G54I))-(G4S)3-
      VHVL(hOKT3)-HDD

<400> SEQUENCE: 18

Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Thr Gly Ile Pro Ala Arg Phe Ser Gly
            50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
                100                 105                 110

Gly Gly Ser Gly Gly Gly Ser Gln Val Gln Leu Val Glu Ser Gly
            115                 120                 125
```

```
Pro Gly Val Val Gln Pro Gly Arg Ser Leu Arg Leu Ser Cys Ala Val
130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
            165                 170                 175

Thr Asn Tyr Asn Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Val Tyr Tyr Cys Ala Ser Arg Gly Gly His Tyr Gly Tyr
210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Ser Gly
                245                 250                 255

Gly Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
    275                 280                 285

Phe Thr Arg Tyr Thr Met His Trp Val Arg Gln Ala Pro Gly Lys Gly
290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
        355                 360                 365

Trp Gly Gln Gly Thr Pro Val Thr Val Ser Ser Gly Gly Gly Gly Ser
    370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
        435                 440                 445

Ser Gly Val Pro Ser Arg Phe Ser Gly Ser Gly Ser Gly Thr Asp Tyr
    450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg Thr Pro Leu Gly Asp Thr Thr His Thr Ser Gly
            500                 505                 510

Met Val Ser Lys Leu Ser Gln Leu Gln Thr Glu Leu Leu Ala Ala Leu
        515                 520                 525

Leu Glu Ser Gly Leu Ser Lys Glu Ala Leu Ile Gln Ala Leu Gly Glu
530                 535                 540

Gly Ser Gly Gly Ala Pro
```

<210> SEQ ID NO 19
<211> LENGTH: 553
<212> TYPE: PRT
<213> ORGANISM: Artificial Sequence
<220> FEATURE:
<223> OTHER INFORMATION: Synthetic polypeptide sequence, 641HLBT-HDD:
      VHVL(KM641)-(G4S)3-VHVL(hOKT3)-HDD

<400> SEQUENCE: 19

```
Glu Val Thr Leu Val Glu Ser Gly Gly Asp Phe Val Lys Pro Gly
1               5                   10                  15

Ser Leu Lys Val Ser Cys Ala Ala Ser Gly Phe Ala Phe Ser His Tyr
            20                  25                  30

Ala Met Ser Trp Val Arg Gln Thr Pro Ala Lys Arg Leu Glu Trp Val
        35                  40                  45

Ala Tyr Ile Ser Ser Gly Gly Ser Gly Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Arg Ser Leu Arg Ser Glu Asp Ser Ala Met Tyr Phe Cys
                85                  90                  95

Thr Arg Val Lys Leu Gly Thr Tyr Tyr Phe Asp Ser Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Met Thr Gln Thr Ala Ser Ser
    130                 135                 140

Leu Pro Ala Ser Leu Gly Asp Arg Val Thr Ile Ser Cys Ser Ala Ser
145                 150                 155                 160

Gln Asp Ile Ser Asn Tyr Leu Asn Trp Tyr Gln Gln Lys Pro Asp Gly
                165                 170                 175

Thr Val Lys Leu Leu Ile Phe Tyr Ser Ser Asn Leu His Ser Gly Val
            180                 185                 190

Pro Ser Arg Phe Ser Gly Gly Ser Gly Thr Asp Tyr Ser Leu Thr
        195                 200                 205

Ile Ser Asn Leu Glu Pro Glu Asp Ile Ala Thr Tyr Phe Cys His Gln
    210                 215                 220

Tyr Ser Lys Leu Pro Trp Thr Phe Gly Gly Gly Thr Lys Leu Glu Ile
225                 230                 235                 240

Lys Arg Ala Ser Thr Lys Gly Pro Gly Gly Gly Ser Gly Gly Gly
                245                 250                 255

Gly Ser Gly Gly Gly Gly Ser Gln Val Gln Leu Val Gln Ser Gly Gly
            260                 265                 270

Gly Val Val Gln Pro Gly Arg Ser Leu Arg Leu Ser Cys Lys Ala Ser
        275                 280                 285

Gly Tyr Thr Phe Thr Arg Tyr Thr Met His Trp Val Arg Gln Ala Pro
    290                 295                 300

Gly Lys Gly Leu Glu Trp Ile Gly Tyr Ile Asn Pro Ser Arg Gly Tyr
305                 310                 315                 320

Thr Asn Tyr Asn Gln Lys Phe Lys Asp Arg Phe Thr Ile Ser Arg Asp
                325                 330                 335

Asn Ser Lys Asn Thr Ala Phe Leu Gln Met Asp Ser Leu Arg Pro Glu
            340                 345                 350
```

```
Asp Thr Gly Val Tyr Phe Cys Ala Arg Tyr Tyr Asp His Tyr Cys
            355                 360                 365

Leu Asp Tyr Trp Gly Gln Gly Thr Pro Val Thr Val Ser Ser Gly Gly
    370                 375                 380

Gly Gly Ser Gly Gly Gly Gly Ser Gly Gly Gly Ser Asp Ile Gln
385                 390                 395                 400

Met Thr Gln Ser Pro Ser Ser Leu Ser Ala Ser Val Gly Asp Arg Val
                405                 410                 415

Thr Ile Thr Cys Ser Ala Ser Ser Val Ser Tyr Met Asn Trp Tyr
            420                 425                 430

Gln Gln Thr Pro Gly Lys Ala Pro Lys Arg Trp Ile Tyr Asp Thr Ser
            435                 440                 445

Lys Leu Ala Ser Gly Val Pro Ser Arg Phe Ser Gly Ser Gly Ser Gly
    450                 455                 460

Thr Asp Tyr Thr Phe Thr Ile Ser Ser Leu Gln Pro Glu Asp Ile Ala
465                 470                 475                 480

Thr Tyr Tyr Cys Gln Gln Trp Ser Ser Asn Pro Phe Thr Phe Gly Gln
                485                 490                 495

Gly Thr Lys Leu Gln Ile Thr Arg Thr Pro Leu Gly Asp Thr Thr His
            500                 505                 510

Thr Ser Gly Met Val Ser Lys Leu Ser Gln Leu Gln Thr Glu Leu Leu
            515                 520                 525

Ala Ala Leu Leu Glu Ser Gly Leu Ser Lys Glu Ala Leu Ile Gln Ala
            530                 535                 540

Leu Gly Glu Gly Ser Gly Gly Ala Pro
545                 550

<210> SEQ ID NO 20
<211> LENGTH: 550
<212> TYPE: PRT
<213> ORGANISM: Artificial Sequence
<220> FEATURE:
<223> OTHER INFORMATION: Synthetic polypeptide sequence,
      3LHBT(D32H,G54I)-HDD: VLVH(hu3F8v1(D32H,G54I))-(G4S)3-
      VHVL(hOKT3)-HDD

<400> SEQUENCE: 20

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn His
                20                  25                  30

Val Thr Trp Tyr Gln Gln Lys Pro Gly Gln Ala Pro Arg Leu Leu Ile
            35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Gly Ser Gln Val Gln Leu Val Glu Ser Gly
            115                 120                 125

Pro Gly Val Val Gln Pro Gly Arg Ser Leu Arg Ile Ser Cys Ala Val
            130                 135                 140

Ser Gly Phe Ser Val Thr Asn Tyr Gly Val His Trp Val Arg Gln Pro
```

```
            145                 150                 155                 160
Pro Gly Lys Gly Leu Glu Trp Leu Gly Val Ile Trp Ala Ile Gly Ile
                165                 170                 175

Thr Asn Tyr Asn Ser Ala Phe Met Ser Arg Leu Thr Ile Ser Lys Asp
                180                 185                 190

Asn Ser Lys Asn Thr Val Tyr Leu Gln Met Asn Ser Leu Arg Ala Glu
            195                 200                 205

Asp Thr Ala Met Tyr Tyr Cys Ala Ser Arg Gly Gly His Tyr Gly Tyr
        210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Ser Gly
                245                 250                 255

Gly Gly Gly Ser Gln Val Gln Leu Val Gln Ser Gly Gly Val Val
                260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
        290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
                340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
        370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
        450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg Thr Pro Leu Gly Asp Thr Thr His Thr Ser Gly
            500                 505                 510

Met Val Ser Lys Leu Ser Gln Leu Gln Thr Glu Leu Leu Ala Ala Leu
        515                 520                 525

Leu Glu Ser Gly Leu Ser Lys Glu Ala Leu Ile Gln Ala Leu Gly Glu
        530                 535                 540

Gly Ser Gly Gly Ala Pro
545                 550

<210> SEQ ID NO 21
```

<211> LENGTH: 550
<212> TYPE: PRT
<213> ORGANISM: Artificial Sequence
<220> FEATURE:
<223> OTHER INFORMATION: Synthetic polypeptide sequence,
      3LHBT(E1K,G54I)-HDD: VLVH(hu3F8v1(E1K,G54I))-(G4S)3-
      VHVL(hOKT3)-HDD

<400> SEQUENCE: 21

```
Lys Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Gly Ser Gly Gly
            100                 105                 110

Gly Gly Ser Gly Gly Gly Gly Ser Gln Val Gln Leu Val Glu Ser Gly
        115                 120                 125

Pro Gly Val Val Gln Pro Gly Arg Ser Leu Arg Ile Ser Cys Ala Val
130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
                165                 170                 175

Thr Asn Tyr Asn Ser Ala Phe Met Ser Arg Leu Thr Ile Ser Lys Asp
            180                 185                 190

Asn Ser Lys Asn Thr Val Tyr Leu Gln Met Asn Ser Leu Arg Ala Glu
        195                 200                 205

Asp Thr Ala Met Tyr Tyr Cys Ala Ser Arg Gly Gly His Tyr Gly Tyr
    210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Gly Ser Gly Gly
                245                 250                 255

Gly Gly Gly Ser Gln Val Gln Leu Val Gln Ser Gly Gly Gly Val Val
            260                 265                 270

Gln Pro Gly Arg Ser Leu Arg Leu Ser Cys Lys Ala Ser Gly Tyr Thr
        275                 280                 285

Phe Thr Arg Tyr Thr Met His Trp Val Arg Gln Ala Pro Gly Lys Gly
    290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
                325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
        355                 360                 365
```

```
Trp Gly Gln Gly Thr Pro Val Thr Val Ser Ser Gly Gly Gly Ser
370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
                405                 410                 415

Cys Ser Ala Ser Ser Val Ser Tyr Met Asn Trp Tyr Gln Gln Thr
                420                 425                 430

Pro Gly Lys Ala Pro Lys Arg Trp Ile Tyr Asp Thr Ser Lys Leu Ala
                435                 440                 445

Ser Gly Val Pro Ser Arg Phe Ser Gly Ser Gly Ser Gly Thr Asp Tyr
450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
                485                 490                 495

Leu Gln Ile Thr Arg Thr Pro Leu Gly Asp Thr Thr His Thr Ser Gly
                500                 505                 510

Met Val Ser Lys Leu Ser Gln Leu Gln Thr Glu Leu Leu Ala Ala Leu
                515                 520                 525

Leu Glu Ser Gly Leu Ser Lys Glu Ala Leu Ile Gln Ala Leu Gly Glu
530                 535                 540

Gly Ser Gly Gly Ala Pro
545                 550

<210> SEQ ID NO 22
<211> LENGTH: 550
<212> TYPE: PRT
<213> ORGANISM: Artificial Sequence
<220> FEATURE:
<223> OTHER INFORMATION: Synthetic polypeptide sequence,
      3LHBTv5(D32H,G54I)-HDD: VLVH(hu3F8v5(D32H,G54I))-(G4S)3-
      VHVL(hOKT3)-HDD

<400> SEQUENCE: 22

Glu Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn His
                20                  25                  30

Val Thr Trp Tyr Gln Gln Lys Pro Gly Gln Ala Pro Arg Leu Leu Ile
                35                  40                  45

Tyr Ser Ala Ser Asn Arg Tyr Thr Gly Ile Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
                100                 105                 110

Gly Gly Ser Gly Gly Gly Gly Ser Gln Val Gln Leu Val Glu Ser Gly
                115                 120                 125

Pro Gly Val Val Gln Pro Gly Arg Ser Leu Arg Leu Ser Cys Ala Val
                130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
```

```
            165                 170                 175
Thr Asn Tyr Asn Ser Val Lys Gly Arg Leu Thr Ile Ser Lys Asp
            180                 185                 190

Asn Ser Lys Asn Thr Val Tyr Leu Gln Met Asn Ser Leu Arg Ala Glu
            195                 200                 205

Asp Thr Ala Val Tyr Tyr Cys Ala Ser Arg Gly Gly His Tyr Gly Tyr
            210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Ser Gly
                245                 250                 255

Gly Gly Gly Ser Gln Val Gln Leu Val Gln Ser Gly Gly Val Val
            260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
            290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
            325                 330                 335

Asn Thr Ala Phe Leu Gln Met Asp Ser Leu Arg Pro Glu Asp Thr Gly
            340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Gly Ser
            370                 375                 380

Gly Gly Gly Gly Ser Gly Gly Gly Ser Asp Ile Gln Met Thr Gln
385                 390                 395                 400

Ser Pro Ser Ser Leu Ser Ala Ser Val Gly Asp Arg Val Thr Ile Thr
            405                 410                 415

Cys Ser Ala Ser Ser Ser Val Ser Tyr Met Asn Trp Tyr Gln Gln Thr
            420                 425                 430

Pro Gly Lys Ala Pro Lys Arg Trp Ile Tyr Asp Thr Ser Lys Leu Ala
            435                 440                 445

Ser Gly Val Pro Ser Arg Phe Ser Gly Ser Gly Ser Gly Thr Asp Tyr
            450                 455                 460

Thr Phe Thr Ile Ser Ser Leu Gln Pro Glu Asp Ile Ala Thr Tyr Tyr
465                 470                 475                 480

Cys Gln Gln Trp Ser Ser Asn Pro Phe Thr Phe Gly Gln Gly Thr Lys
            485                 490                 495

Leu Gln Ile Thr Arg Thr Pro Leu Gly Asp Thr Thr His Thr Ser Gly
            500                 505                 510

Met Val Ser Lys Leu Ser Gln Leu Gln Thr Glu Leu Leu Ala Ala Leu
            515                 520                 525

Leu Glu Ser Gly Leu Ser Lys Glu Ala Leu Ile Gln Ala Leu Gly Glu
            530                 535                 540

Gly Ser Gly Gly Ala Pro
545                 550

<210> SEQ ID NO 23
<211> LENGTH: 550
<212> TYPE: PRT
<213> ORGANISM: Artificial Sequence
```

<220> FEATURE:
<223> OTHER INFORMATION: Synthetic polypeptide sequence,
      3LHBTv5(E1K,G54I)-HDD: VLVH(hu3F8v5(E1K,G54I))-(G4S)3-
      VHVL(hOKT3)-HDD

<400> SEQUENCE: 23

```
Lys Ile Val Met Thr Gln Thr Pro Ala Thr Leu Ser Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Gly Gly Gly Ser Gly Gly
            100                 105                 110

Gly Gly Ser Gly Gly Gly Ser Gln Val Gln Leu Val Glu Ser Gly
        115                 120                 125

Pro Gly Val Val Gln Pro Gly Arg Ser Leu Arg Leu Ser Cys Ala Val
130                 135                 140

Ser Gly Phe Ser Val Thr Asn Tyr Gly Val His Trp Val Arg Gln Pro
145                 150                 155                 160

Pro Gly Lys Gly Leu Glu Trp Leu Gly Val Ile Trp Ala Ile Gly Ile
            165                 170                 175

Thr Asn Tyr Asn Ser Val Lys Gly Arg Leu Thr Ile Ser Lys Asp
        180                 185                 190

Asn Ser Lys Asn Thr Val Tyr Leu Gln Met Asn Ser Leu Arg Ala Glu
            195                 200                 205

Asp Thr Ala Val Tyr Tyr Cys Ala Ser Arg Gly Gly His Tyr Gly Tyr
        210                 215                 220

Ala Leu Asp Tyr Trp Gly Gln Gly Thr Leu Val Thr Val Ser Ser Ala
225                 230                 235                 240

Ser Thr Lys Gly Pro Gly Gly Gly Ser Gly Gly Gly Ser Gly
            245                 250                 255

Gly Gly Ser Gln Val Gln Leu Val Gln Ser Gly Gly Val Val
        260                 265                 270

Gln Pro Gly Arg Ser Leu Arg Leu Ser Cys Lys Ala Ser Gly Tyr Thr
            275                 280                 285

Phe Thr Arg Tyr Thr Met His Trp Val Arg Gln Ala Pro Gly Lys Gly
290                 295                 300

Leu Glu Trp Ile Gly Tyr Ile Asn Pro Ser Arg Gly Tyr Thr Asn Tyr
305                 310                 315                 320

Asn Gln Lys Phe Lys Asp Arg Phe Thr Ile Ser Arg Asp Asn Ser Lys
            325                 330                 335

Asn Thr Ala Phe Leu Gln Met Asp Ser Leu Arg Pro Glu Asp Thr Gly
        340                 345                 350

Val Tyr Phe Cys Ala Arg Tyr Tyr Asp Asp His Tyr Cys Leu Asp Tyr
            355                 360                 365

Trp Gly Gln Gly Thr Pro Val Thr Val Ser Ser Gly Gly Gly Ser
370                 375                 380
```

```
Gly Gly Gly Gly Ser Gly Gly Gly Ser Asp Ile Gln Met Thr Gln
385             390             395             400

Ser Pro Ser Ser Leu Ser Ala Ser Val Gly Asp Arg Val Thr Ile Thr
                405             410                 415

Cys Ser Ala Ser Ser Ser Val Ser Tyr Met Asn Trp Tyr Gln Gln Thr
                420             425                 430

Pro Gly Lys Ala Pro Lys Arg Trp Ile Tyr Asp Thr Ser Lys Leu Ala
        435             440             445

Ser Gly Val Pro Ser Arg Phe Ser Gly Ser Gly Ser Gly Thr Asp Tyr
    450             455             460

Thr Phe Thr Ile Ser Ser Leu Gln Pro Glu Asp Ile Ala Thr Tyr Tyr
465             470             475             480

Cys Gln Gln Trp Ser Ser Asn Pro Phe Thr Phe Gly Gln Gly Thr Lys
            485             490             495

Leu Gln Ile Thr Arg Thr Pro Leu Gly Asp Thr Thr His Thr Ser Gly
            500             505             510

Met Val Ser Lys Leu Ser Gln Leu Gln Thr Glu Leu Leu Ala Ala Leu
        515             520             525

Leu Glu Ser Gly Leu Ser Lys Glu Ala Leu Ile Gln Ala Leu Gly Glu
    530             535             540

Gly Ser Gly Gly Ala Pro
545             550

<210> SEQ ID NO 24
<211> LENGTH: 34
<212> TYPE: PRT
<213> ORGANISM: Artificial Sequence
<220> FEATURE:
<223> OTHER INFORMATION: Synthetic polypeptide sequence, helix-turn-
      helix domain

<400> SEQUENCE: 24

Gly Glu Leu Glu Glu Leu Leu Lys His Leu Lys Glu Leu Leu Lys Gly
1               5                   10                  15

Pro Arg Lys Gly Glu Leu Glu Glu Leu Leu Lys His Leu Lys Glu Leu
                20                  25                  30

Leu Lys
```